US007543549B2

(12) United States Patent
Valencia et al.

(10) Patent No.: US 7,543,549 B2
(45) Date of Patent: Jun. 9, 2009

(54) CATTLE MANAGEMENT SYSTEM AND METHOD

(75) Inventors: Neal Valencia, Eaton, CO (US); Michael A. Ackerman, Windsor, CO (US); Jim Carisch, Denver, CO (US)

(73) Assignee: Lextron, Inc., Greeley, CO (US)

( * ) Notice: Subject to any disclaimer, the term of this patent is extended or adjusted under 35 U.S.C. 154(b) by 503 days.

(21) Appl. No.: 11/228,020

(22) Filed: Sep. 14, 2005

(65) Prior Publication Data

US 2006/0054092 A1    Mar. 16, 2006

Related U.S. Application Data

(60) Provisional application No. 60/609,914, filed on Sep. 14, 2004.

(51) Int. Cl.
*A01K 29/00* (2006.01)
*G01F 17/00* (2006.01)

(52) U.S. Cl. .......................... 119/174; 700/90
(58) Field of Classification Search .............. 119/14.02, 119/174; 700/90
See application file for complete search history.

(56) References Cited

U.S. PATENT DOCUMENTS

| 3,191,807 | A | 6/1965 | Rodrigues, Jr. | 222/49 |
| 3,437,075 | A | 4/1969 | Hawes, Jr. et al. | 119/51 |
| 3,498,311 | A | 3/1970 | Hawes, Jr. | 137/101.25 |
| 3,670,923 | A | 6/1972 | Hawes, Jr. et al. | 222/2 |
| 3,741,440 | A | 6/1973 | Sanders, Jr. | 222/132 |
| 3,804,303 | A | 4/1974 | Fassauer | 222/193 |
| 3,806,001 | A | 4/1974 | Pratt | 222/132 |
| 3,822,056 | A | 7/1974 | Hawes, Jr. et al. | 259/25 |
| 3,881,688 | A | 5/1975 | Senn | 366/173.2 |
| 3,981,417 | A | 9/1976 | Fassauer | 222/193 |
| 4,086,663 | A | 4/1978 | Croft | 366/173.2 |
| 4,288,856 | A | 9/1981 | Linseth | |
| 4,395,131 | A | 7/1983 | Barlow | 366/141 |
| 4,430,001 | A | 2/1984 | Schurr | 366/163.1 |
| 4,733,971 | A | 3/1988 | Pratt | 366/141 |
| 4,801,210 | A | 1/1989 | Gian | 366/156 |
| 4,815,042 | A | 3/1989 | Pratt | 366/141 |
| 4,889,433 | A | 12/1989 | Pratt | 366/141 |

(Continued)

OTHER PUBLICATIONS

International Search Report for International (PCT) Patent Application No. PCT/US2005/032964, mailed Nov. 8, 2007.

(Continued)

*Primary Examiner*—Rob Swiatek
(74) *Attorney, Agent, or Firm*—Sheridan Ross P.C.

(57) ABSTRACT

A cattle management system and method are provided for managing numerous routine and non-routine management activities. The system and method incorporate a data processing system wherein comprehensive data is gathered and maintained on each individual animal as well as on selected groups of animals. Preferably, a central database is used which allows enhanced functionality with respect to not only data entry and data transfer, but also with respect to providing system generated management recommendations. Some significant functionality of the present invention includes the ability to track the location of each individual animal by utilizing unique identification data for each animal, recording all monitored events that take place at each location during the animal's production cycle, and reporting the events and locations as required to government entities, financial institutions, and other entities within the cattle industry.

11 Claims, 137 Drawing Sheets

U.S. PATENT DOCUMENTS

| | | | | |
|---|---|---|---|---|
| 4,910,024 | A | 3/1990 | Pratt | 426/2 |
| 5,008,821 | A | 4/1991 | Pratt et al. | |
| 5,219,224 | A | 6/1993 | Pratt | 366/141 |
| 5,240,324 | A | 8/1993 | Phillips et al. | 366/141 |
| 5,280,859 | A | 1/1994 | Rust et al. | 241/101.6 |
| 5,284,388 | A | 2/1994 | Volk et al. | 366/141 |
| 5,303,998 | A | 4/1994 | Whitlatch et al. | 366/101 |
| 5,315,505 | A | 5/1994 | Pratt et al. | |
| 5,340,211 | A | 8/1994 | Pratt | 366/141 |
| 5,350,257 | A | 9/1994 | Newbolt et al. | 406/75 |
| 5,369,032 | A | 11/1994 | Pratt | 435/290 |
| 5,401,501 | A | 3/1995 | Pratt | 424/93.45 |
| 5,423,456 | A | 6/1995 | Arendonk et al. | 222/54 |
| 5,457,627 | A | 10/1995 | Cureton et al. | |
| 5,487,603 | A | 1/1996 | Hoff et al. | 366/141 |
| 5,573,002 | A | 11/1996 | Pratt | |
| 5,634,713 | A | 6/1997 | Abe | 366/156.1 |
| 5,634,716 | A | 6/1997 | Westall et al. | 366/141 |
| 5,636,118 | A | 6/1997 | Brewster et al. | |
| 5,673,647 | A | 10/1997 | Pratt | 119/51.02 |
| 5,718,507 | A | 2/1998 | Gian | 366/131 |
| 5,803,906 | A | 9/1998 | Pratt et al. | |
| 5,836,880 | A | 11/1998 | Pratt | |
| 5,853,244 | A | 12/1998 | Hoff et al. | 366/141 |
| 5,867,820 | A | 2/1999 | Cureton et al. | |
| 5,878,402 | A | 3/1999 | Brewster et al. | |
| 5,899,561 | A | 5/1999 | Gian | 366/141 |
| 5,984,875 | A * | 11/1999 | Brune | 600/549 |
| 6,000,361 | A | 12/1999 | Pratt | |
| 6,032,084 | A | 2/2000 | Anderson et al. | |
| 6,131,744 | A | 10/2000 | Pratt | |
| 6,135,055 | A | 10/2000 | Pratt | |
| 6,200,210 | B1 | 3/2001 | Pratt | |
| 6,203,184 | B1 | 3/2001 | O'Callaghan | 366/141 |
| 6,216,053 | B1 | 4/2001 | Cureton et al. | |
| 6,250,793 | B1 | 6/2001 | Gian | 366/131 |
| 6,318,289 | B1 | 11/2001 | Pratt | |
| 6,329,001 | B1 | 12/2001 | Ivey et al. | 426/2 |
| 6,516,270 | B2 | 2/2003 | Pavlak et al. | |
| 6,516,746 | B2 | 2/2003 | Pratt | |
| 6,537,213 | B2 | 3/2003 | Dodds | |
| 6,547,726 | B2 | 4/2003 | Pratt et al. | |
| 6,579,236 | B2 | 6/2003 | Pratt | |
| 6,592,517 | B2 | 7/2003 | Pratt et al. | |
| 6,736,272 | B2 | 5/2004 | Pratt | |
| 6,745,126 | B1 | 6/2004 | Pavlak et al. | |
| 6,805,075 | B2 | 10/2004 | Pratt | |
| 6,901,369 | B2 | 5/2005 | Cureton et al. | |
| 6,932,024 | B2 | 8/2005 | Da et al. | |
| 2001/0016681 | A1 | 8/2001 | Pratt et al. | |
| 2001/0044579 | A1 | 11/2001 | Pratt | |
| 2002/0050248 | A1 | 5/2002 | Pratt | |
| 2002/0056669 | A1 | 5/2002 | Pratt | |
| 2002/0115915 | A1 | 8/2002 | Pratt et al. | |
| 2003/0188689 | A1 | 10/2003 | Pratt | |
| 2005/0000458 | A1 | 1/2005 | Pratt | |
| 2006/0201432 | A1 | 9/2006 | Pratt | |

OTHER PUBLICATIONS

Written Opinion for International (PCT) Patent Application No. PCT/US2005/032964, mailed Nov. 8, 2007.

International Preliminary Report on Patentability for International (PCT) Patent Application No. PCT/US2005/032964, mailed Dec. 21, 2007.

\* cited by examiner

Pre-Assigned Criteria

| | |
|---|---|
| Average Daily Gain | Owner |
| Assigned Ration | Percent Deads |
| Class Code | Pen Number |
| Consumption by Body Weight | Pen Type |
| Consumption Per Head | Repeat Days |
| Condition Code | Repull Count |
| Current Animal Weight | Retreat Count |
| Current Group Weight | Risk Factor |
| Buyer Code | Ration Dry Matter |
| Breed Code | User Code 1 |
| Days on Feed | User Code 2 |
| Days on Ration | User Code 3 |
| Days Until Projected Ship | Load ID |
| Days Since Last Treatment | Ration Group |
| Diagnosis | Severity Level |
| Diagnosis (Previous) | Severity Level (Previous) |
| Dry Consumption Per Head | Sex |
| Feed Call Priority | Slick Time |
| Custom Formula | Temperature |
| Hospital Head Count | Treatment Count |
| In Date | Yesterday's Call |
| In Weight | Yesterday's Hospital Head Count |
| Last Ration Assigned | Total Digestible Nutrients |
| Origin | Net Energy For Gain |
| Target Consumption | Net Energy for Maintenance |
| Premise Code | USDA Tag |

| Drug Name | Drug Long Name |
|---|---|
| ☐ 7 WAY | 7 WAY |
| ☐ 7WAY S | 7 WAY/SOMNUS |
| ☐ A180 | A180 |
| ☐ ADSPEC | ADSPEC |
| ☐ AGRI B | SULFADIMETHIZINE |
| ☐ ALBONB | ALBON-SR BOLUS |
| ☐ ALBONI | SULFADIMETHOXINE |
| ☐ B COMP | VITAMIN B COMPLEX |
| ☐ B1 | VIT B1 |
| ☐ B100 | BAYTRIL 100 |
| ☐ B12 | CYANOCOBALAZIN |
| ☐ B4L5 | VAC 4 + LEPTO 5 |
| ☐ BANAMI | BANAMINE |
| ☐ BANDS | BANDING LOOPS |
| ☐ BATTLE | BATTLE DRENCH |
| ☐ BLUE | BLUE LYTE |
| ☐ BO4 | BRSV VAC 4 |

☐ Treatments Only
☐ Processing Only

OK    Cancel

LEXTRON

Processing/Mass Treatment Work Orders

7/26/2004 - 10:14 am

Lot: 440
Ren: 513

Head Count: 61
Average Wt: 900.0

Date: 07/26/2004
Type: Processing

| Drug | Head Cnt | Dose | Usage | Serial Numbers of Drug |
|------|----------|------|-------|------------------------|
| EAR | | 1.0 EA | | |
| IVERPO | | 40.5 CC | | |
| PYR-5 | | 1.0 CC | | |
| COMPEH | | 1.0 DS | | |
| COMPES | | 1.0 DS | | |
| COMPTH | | 1.0 DS | | |

| Diagnoses | | | |
|---|---|---|---|
| Code | Description | Dtb.Equiv. | Diagnosis Class Code |
| A | ACUTE PNEUMONIA | | OTHER |
| B | CHRONIC PNEUMONIA | | OTHER |
| C | FROTHY PNEUMONIA | | OTHER |
| D | MISCELLANIOUS | | OTHER |
| E | DIPTHERIA/HONKER | | OTHER |
| F | HONKER | | OTHER |
| G | DIGESTIVE | | OTHER |
| H | BLOAT | | OTHER |
| I | ACIDOSIS | | OTHER |
| J | COCCIDIOSIS | | OTHER |
| K | BOWEL OBSTRUCTION | | OTHER |
| L | FOOTROT | | OTHER |
| M | ACUTE PNEWUMONIA 2 | | OTHER |
| N | VAGINAL PROLAPSE | | OTHER |
| O | CALVER/ABORTION | | OTHER |

| | Quantity | Cost | Unit Cost |
|---|---|---|---|
| Inventory Inquiry | | | |
| Drug ID | 7 WAY | | |
| Name | 7 WAY | | |
| Unit of Measure | Dose | | |
| Beginning Period | 4/24/2004 | | |
| Beginning Balance | 0.00 | $0.00 | $0.0000 |
| To Date Usage | 838.00 | $0.00 | $0.0000 |
| To Date Receipts | 1,000.00 | $345.50 | $0.3455 |
| To Date Adjustments | 50.00 | $17.28 | $0.3455 |
| Inventory Balance | 212.00 | $362.78 | $1.7112 |

| Breed Codes | | |
|---|---|---|
| Code | BreedName | |
| AN | Angus | |
| AR | Red Angus | |
| BN | Brangus | |
| BR | Brahman | |
| BV | Braunvieh | |
| CG | Chianina | |
| CH | Charolais | |
| GV | Gelbvieh | |
| HH | Hereford (horned) | |
| HP | Hereford (polled) | |
| IB | Irish Black | |
| LM | Limousin | |
| MA | Maine-Anjou | |
| SH | Shorthorns | |
| SL | Saler | |
| SM | Simmental | |

[ Save ] [ Report ] [ Exit ]

| Lot | Home Pen | From Pen | Tag Number | Alt. Tag | Head Cnt |
|---|---|---|---|---|---|
| 20 | 311 | 416 | 209363 | | 1 |
| 322S | 403 | 416 | 322343 | | 1 |
| 322S | 403 | 416 | 322343 | | 1 |
| 322S | 403 | 416 | 322382 | | 1 |
| 322S | 403 | 416 | 322382 | | 1 |
| 40 | 202 | 416 | 401 | | 1 |
| 40 | 202 | 416 | 402 | | 1 |
| 403 | 129 | 416 | 403725 | | 1 |
| 403 | 129 | 416 | 403731 | | 1 |
| 403 | 129 | 416 | 403747 | | 1 |
| 403 | 129 | 416 | 403787 | | 1 |
| 430 | 410 | 416 | 430933 | | 1 |
| 430 | 410 | 416 | 430939 | | 1 |
| 432 | 130 | 416 | 432800 | | 1 |
| 432 | 130 | 416 | 432804 | | 1 |
| 432 | 130 | 416 | 432813 | | 1 |
| 441 | 412 | 416 | 441315 | | 1 |
| 443 | 127 | 416 | 44366 | | 1 |
| 443 | 127 | 416 | 44377 | | 1 |
| 444 | 503 | 416 | 444703 | | 1 |

Report 1.1                                   User: LEX

FIGURE 93

| Hospital Pen | Lot | Pen | Tag Number | Date of Last Treatment |
|---|---|---|---|---|
| H1 | 10 | 307 | 101449 | 08/08/2004 |
|  | 428 | 613 | 428970 | 08/10/2004 |
|  | 440 | 513 | 440118 | 05/07/2004 |
|  | 442 | 502 | 442261 | 08/09/2004 |
|  | 443 | 127 | 4436 | 08/09/2004 |
|  | 458 | 122 | 458983 | 07/04/2004 |
|  | 460 | 204 | 460786 | 06/29/2004 |
|  |  |  | 460915 | 08/09/2004 |
|  |  | 310 | 460787 | 06/29/2004 |
|  | 461N | 507 | 461278 | 08/10/2004 |
|  |  |  | 461420 | 08/09/2004 |
|  |  |  | 461435 | 08/10/2004 |
|  | 466N | 417 | 466574 | 08/10/2004 |
|  |  |  | 466584 | 08/09/2004 |
|  |  |  | 466591 | 08/09/2004 |
|  |  |  | 466646 | 08/09/2004 |
|  |  |  | 466647 | 08/10/2004 |
|  | 70 | 124 | 701127 | 08/09/2004 |
|  | 80 | 512 | 1409801409 | 07/09/2004 |
|  |  |  | 801458 | 07/10/2004 |
|  |  |  | Pen Total: | 20 |
| H3 | 422 | 111 | 422633 | 06/29/2004 |
|  | 445 | 504 | 44553 | 08/10/2004 |
|  | 456 | 509 | 456285 | 07/31/2004 |
|  | 457 | 103 | 457246 | 06/03/2004 |
|  | 80 | 201 | 801251 | 07/30/2004 |
|  | 90 | 612 | 908914 | 08/10/2004 |
|  |  |  | Pen Total: | 6 |

*Hospital Total: 26

Report 1.2     User: LEX

FIGURE 94

| Lot | Pen | ID Tag | Date Last Treated |
|---|---|---|---|
| 10 | 307 | 101518 | 08/03/2004 |
| 11 | 304 | 11357 | |
| | | 11365 | |
| 391S | 501 | 391165 | 06/20/2004 |
| 40 | 202 | 404 | 08/10/2004 |
| 403 | 129 | 403169 | 08/03/2004 |
| | | 403180 | 08/05/2004 |
| | | 403182 | 08/05/2004 |
| 425 | RYE | 425153 | 05/12/2004 |
| 427 | 308 | 427821 | 08/07/2004 |
| 431 | 110 | 431103 | 07/25/2004 |
| 432 | 130 | 432760 | 08/06/2004 |
| 438 | 128 | 43877 | 08/09/2004 |
| 442 | 502 | 442175 | 08/08/2004 |
| | | 442284 | 08/10/2004 |
| 443 | 127 | 44332 | |
| 445 | 504 | 44596 | 08/09/2004 |
| 447 | 123 | 447171 | 08/10/2004 |
| | | 447210 | 08/09/2004 |

Pen Total: 19

Report 1.4    User: LEX

FIGURE 95

Regular Pen Movements

| Head | Description | Tag # | From Lot | From Pen | To Lot | To Pen |
|---|---|---|---|---|---|---|
| 34 | CATTLE MOVEMENT | | 10 | N1 | 10 | 307 |
| 34 | Total Head Moved in Regular Pens | | | | | |

Hospital/Special Pen Movements Detail

| Lot | Home Pen | Head | Tag # | From Pen | To Pen |
|---|---|---|---|---|---|
| 11 | 304 | 1 | 11365 | 304 | H1 |
| 11 | 304 | 1 | 11357 | 304 | H1 |
| 20 | 311 | 1 | 209363 | 416 | 311 |
| 322S | 403 | 1 | 322343 | 416 | 403 |
| 322S | 403 | 1 | 322382 | 416 | 403 |
| 40 | 202 | 1 | 401 | 416 | 202 |
| 40 | 202 | 1 | 402 | 416 | 202 |
| 403 | 129 | 1 | 403731 | 416 | 129 |
| 403 | 129 | 1 | 403725 | 416 | 129 |
| 403 | 129 | 1 | 403787 | 416 | 129 |
| 403 | 129 | 1 | 403747 | 416 | 129 |
| 416 | 112 | 1 | 416793 | 416 | 300 |
| 430 | 410 | 1 | 430933 | 416 | 410 |

Report 3.0  User: LEX

FIGURE 96

Hospital/Special Pen Movements Detail

| Lot | Home Pen | Head | Tag # | From Pen | To Pen |
|---|---|---|---|---|---|
| 462N | 106 | 1 | 4623 | 416 | 106 |
| 462N | 106 | 1 | 4622 | 106 | H1 |
| 462N | 106 | 1 | 4624 | 416 | H1 |
| 463N | 418 | 1 | 463400 | 416 | 418 |
| 464 | 208 | 1 | 464384 | 416 | 208 |
| 464 | 208 | 1 | 464378 | 416 | 208 |
| 50 | 511 | 1 | 505161 | 416 | 511 |
| 50 | 125 | 1 | 501087 | 416 | 125 |
| 70 | 124 | 1 | 701196 | 416 | 124 |
| 70 | 124 | 1 | 701255 | 416 | 124 |

Total Movements: 59

Hospital/Special Pen Movements Summary

| Lot | Home Pen | Home In/Out | Hospital In/Out | Buller In/Out | Railer In/Out | Recovery In/Out | Chronic In/Out | Hosp Dead | Shipped Railers |
|---|---|---|---|---|---|---|---|---|---|
| 11 | 304 | 0/2 | 2/0 | 0/0 | 0/0 | 0/0 | 0/0 | 0 | 0 |
| 20 | 311 | 1/0 | 0/0 | 0/0 | 0/0 | 0/1 | 0/0 | 0 | 0 |
| 322S | 403 | 2/0 | 0/0 | 0/0 | 0/0 | 0/2 | 0/0 | 0 | 0 |
| 40 | 202 | 2/0 | 0/0 | 0/0 | 0/0 | 0/2 | 0/0 | 0 | 0 |
| 403 | 129 | 4/0 | 0/0 | 0/0 | 0/0 | 0/4 | 0/0 | 0 | 0 |
| 416 | 112 | 0/0 | 0/0 | 1/0 | 0/0 | 0/1 | 0/0 | 0 | 0 |
| 430 | 410 | 2/0 | 0/0 | 0/0 | 0/0 | 0/2 | 0/0 | 0 | 0 |
| 432 | 130 | 3/0 | 0/0 | 0/0 | 0/0 | 0/3 | 0/0 | 0 | 0 |
| 437 | 301 | 0/0 | 0/0 | 1/0 | 0/0 | 0/1 | 0/0 | 0 | 0 |
| 441 | 412 | 1/0 | 0/0 | 0/0 | 0/0 | 0/1 | 0/0 | 0 | 0 |
| 442 | 502 | 0/0 | 0/0 | 1/0 | 0/0 | 0/1 | 0/0 | 0 | 0 |
| 443 | 127 | 2/0 | 0/0 | 0/0 | 0/0 | 0/2 | 0/0 | 0 | 0 |
| 444 | 503 | 1/0 | 0/1 | 0/0 | 0/0 | 1/1 | 0/0 | 0 | 0 |
| 446 | 126 | 1/0 | 0/0 | 0/0 | 0/0 | 0/1 | 0/0 | 0 | 0 |
| 448 | 602 | 1/0 | 0/0 | 0/0 | 0/0 | 0/1 | 0/0 | 0 | 0 |
| 449 | 515 | 1/0 | 0/0 | 0/0 | 0/0 | 0/1 | 0/0 | 0 | 0 |

Report 3.0    User: LEX

FIGURE 97

| | | | | | | | | | |
|---|---|---|---|---|---|---|---|---|---|
| 463N | 418 | 1/0 | 0/0 | 0/0 | 0/0 | 0/1 | 0/0 | 0 | 0 |
| 464 | 208 | 2/0 | 0/0 | 0/0 | 0/0 | 0/2 | 0/0 | 0 | 0 |
| 50 | 125 | 1/0 | 0/0 | 0/0 | 0/0 | 0/1 | 0/0 | 0 | 0 |
| 50 | 511 | 1/0 | 0/0 | 0/0 | 0/0 | 0/1 | 0/0 | 0 | 0 |
| 70 | 124 | 6/0 | 0/0 | 0/0 | 0/0 | 0/6 | 0/0 | 0 | 0 |
| 80 | 201 | 0/0 | 1/1 | 0/0 | 0/0 | 0/0 | 0/0 | 0 | 0 |
| 80 | 512 | 3/0 | 0/0 | 0/0 | 0/0 | 0/3 | 0/0 | 0 | 0 |
| 90 | 612 | 1/0 | 0/0 | 0/0 | 0/0 | 0/1 | 0/0 | 0 | 0 |
| Yard Totals: | | 46/4 | 7/4 | 4/0 | 0/0 | 2/51 | 0/0 | 0 | 0 |

Summary of First Day Pulls to Hospital

| Lot | Home Pen | Tag # | Diagnosis | Treatment | Tempe | Pen Rider | Hosp Pen |
|---|---|---|---|---|---|---|---|
| 11 | 304 | 11365 | OBSERVE | OB1 | 101.7 | | H1 |
| 11 | 304 | 11357 | OBSERVE | OB1 | 101.0 | | H1 |
| 457 | 103 | 457421 | FOOTROT | L3 | 103.0 | | H1 |
| 462N | 106 | 4622 | PINKEYE | U1 | 103.5 | | H1 |

Total Animals pulled to hospitals: 4

Report 3.0     User: LEX

FIGURE 98

| | Number of Animals | | % of Total | Average Days Treated | Average Days On Feed |
|---|---|---|---|---|---|
| Treatments | | | | | |
| | 4 | Animals Treated | 100.0% | 3 | 66 |
| | 3 | First Time Treats | 75.0% | 1 | 53 |
| | 1 | Retreats | 25.0% | 7 | 106 |
| | 1 | Treated More Than 3 days | 25.0% | 7 | 106 |

Report 4.1  User: LEX

| Lot Number 10 | | | | | |
|---|---|---|---|---|---|
| Pen Number | Head Rcvd | In Date | DOF | Shipped | |
| 307 | 34 | 07/08/2004 | 42 | | |
| Total Lot Head Rcvd | | 34 | | | |

| Treatment Analysis Summary | | | Cost Analysis Summary | | |
|---|---|---|---|---|---|
| | | | | Per Total Head | Per Head Trt/Proc |
| Animals Treated | 2 | 5.88% | Total Price | | |
| FirstTimeTreats | 2 | 5.88% | | | |
| Retreats | 0 | 0.00% | Treatments $19.30 | $0.57 | $9.65 |
| Deads | 1 | 2.94% | Mass/Process $0.00 | $0.00 | $0.00 |

| Lot Number 11 | | | | | |
|---|---|---|---|---|---|
| Pen Number | Head Rcvd | In Date | DOF | Shipped | |
| 304 | 73 | 07/20/2004 | 30 | | |
| Total Lot Head Rcvd | | 73 | | | |

| Treatment Analysis Summary | | | Cost Analysis Summary | | |
|---|---|---|---|---|---|
| | | | | Per Total Head | Per Head Trt/Proc |
| Animals Treated | 0 | 0.00% | Total Price | | |
| FirstTimeTreats | 0 | 0.00% | | | |
| Retreats | 0 | 0.00% | Treatments | | |
| Deads | 0 | 0.00% | Mass/Process | | |

Report 4.3　　　　　　　　　　　　　　User: LEX

FIGURE 101

Lot Summary

| Pen Number | Head Rcvd | In Date | In Weight | DOF | Shipped |
|---|---|---|---|---|---|
| 307 | 34 | 07/08/2004 | 335 | 42 | |
| Total Hd Cnt and Averages | 34 | 07/08/2004 | 335 | 42 | |

Current Head Counts

| Home Per | Hospital | Recovery | Chronic | Buller | Railer | Deads | Shipped |
|---|---|---|---|---|---|---|---|
| 31 | 1 | 1 | 0 | 0 | 0 | 1 | 0 |

Treatments Summary

Number of animals treated: 2  Average number of treatments
Total number of treatments: 2  for each treated animal: 1.0

| Diagnosis | Head Count | # Treatments | % Of Lot | % Of Treated |
|---|---|---|---|---|
| ACUTE PNEUMONIA | 2 | 2 | 5.9% | 100.0 |

Death Summary

Number of animals that have died in lot: 1

| Diagnosis | Head Count | % Of Lot | % Of Treated |
|---|---|---|---|
| CHRONIC PNEUMONIA | 1 | 2.9 | 50.0 |

Price Summary

| | | | |
|---|---|---|---|
| Total Price of Processing: | $0.00 | *Price per Head for Processing: | $0.00 |
| Total Price of Mass Treatment: | $0.00 | *Price per Head for Mass Treat: | $0.00 |
| Total Price of Treatments: | $19.30 | *Price per Head for Treatments: | $0.57 |
| Average Price per Treatment: | $9.65 | **Price per Head Treated: | $9.65 |

\* Based on total head count
\*\* Based on number of animals treated

Report 4.4                                  User: LEX

FIGURE 102

|  | Disease | 1st Time Treat | Retreats | Head Count Treated | Percent of Treatments |  |
|---|---|---|---|---|---|---|
| Lot: 456 |  |  |  |  |  |  |
| Pen: 509 |  |  |  |  |  |  |
|  | FOOTROT | 1 |  | 1 | 100.0 | % |
|  | Total Treated for Lot 456 |  |  | 1 | 2.6 | %Lot |
| Lot: 457 |  |  |  |  |  |  |
| Pen: 103 |  |  |  |  |  |  |
|  | FOOTROT | 1 |  | 1 | 100.0 | % |
|  | Total Treated for Lot 457 |  |  | 1 | 1.1 | %Lot |
| Lot: 462N |  |  |  |  |  |  |
| Pen: 106 |  |  |  |  |  |  |
|  | PINKEYE | 1 |  | 1 | 100.0 | % |
|  | Total Treated for Lot 462N |  |  | 1 | 0.7 | %Lot |
| Lot: 80 |  |  |  |  |  |  |
| Pen: 201 |  |  |  |  |  |  |
|  | CHRONIC PNEUMONIA |  | 1 | 1 | 100.0 | % |
|  | Total Treated for Lot 80 |  |  | 1 | 1.7 | %Lot |
|  | Total Treated for Day |  |  | 4 | 0.1 | %Yard |

Report 4.2  User: LEX

FIGURE 103

Manager's Lot Summary Report
For 08/01/2004 to 08/18/2004

| Lot | Date In | Head In | Animals Pulled | 1st Treat | 1st ReTrt | 2nd ReTrt | 3rd ReTrt | 4/More ReTrts | Morbidity Deads | | |
|-----|---------|---------|---------|-------|-------|-------|-------|--------|-------|-------|------|
| | | | | | | | | | Total | %Pull | %Lot |
| 10  | 07/08/2004 | 34  | 2 | 2 | 0 | 0 | 0 | 0 | 0 | 0.00 | 0.00 |
| 40  | 05/19/2004 | 130 | 1 | 1 | 0 | 0 | 0 | 0 | 0 | 0.00 | 0.00 |
| 403 | 03/16/2004 | 126 | 3 | 3 | 0 | 0 | 0 | 0 | 0 | 0.00 | 0.00 |
| 427 | 05/10/2004 | 185 | 1 | 0 | 1 | 0 | 0 | 0 | 0 | 0.00 | 0.00 |
| 428 | 03/09/2004 | 143 | 1 | 0 | 0 | 1 | 0 | 0 | 0 | 0.00 | 0.00 |
| 432 | 03/17/2004 | 196 | 1 | 1 | 0 | 0 | 0 | 0 | 0 | 0.00 | 0.00 |
| 438 | 03/24/2004 | 87  | 1 | 1 | 0 | 0 | 0 | 0 | 0 | 0.00 | 0.00 |
| 442 | 04/27/2004 | 117 | 3 | 3 | 0 | 0 | 0 | 0 | 0 | 0.00 | 0.00 |
| 445 | 05/04/2004 | 125 | 2 | 2 | 0 | 0 | 0 | 0 | 0 | 0.00 | 0.00 |
| 447 | 05/12/2004 | 228 | 2 | 1 | 1 | 0 | 0 | 0 | 0 | 0.00 | 0.00 |

Report 4.5

User: LEX

FIGURE 104

* Feedlot Summary *

* Head Count: 444 *

Health Related Deaths
*Selected Lots*

| Description | Head Count | % | # Of Lots | Average | Low | High |
|---|---|---|---|---|---|---|
| CHRONIC PNEUMONIA | 2 | 0.450% | 2 | 1.783% | 0.625% | 2.941% |
| Total Deaths: | 2 | 0.450% | 2 | 1.783% | 0.625% | 2.941% |

Health Occurences
*Selected Lots*

| Description | Head Count | % | # Of Lots | Average | Low | High |
|---|---|---|---|---|---|---|
| ACUTE PNEUMONIA | 11 | 2.477% | 2 | 5.754% | 5.625% | 5.882% |
| CHRONIC PNEUMONIA | 2 | 0.450% | 2 | 0.513% | 0.400% | 0.625% |
| FROTHY PNEUMONIA | 1 | 0.225% | 1 | 0.625% | 0.625% | 0.625% |

* Lot #: 10 *

* Head Count: 34 *

Health Related Deaths
* This Lot *

| Description | Head Count | % of Lot | # Of Lots | Average | Low | High |
|---|---|---|---|---|---|---|
| CHRONIC PNEUMONIA | 1 | 2.941% | 2 | 1.783% | 0.625% | 2.941% |
| Total Deaths: | 1 | 2.941% | 2 | 1.783% | 0.625% | 2.941% |

Health Occurences
* This Lot *

| Description | Head Count | % of Lot | # Of Lots | Average | Low | High |
|---|---|---|---|---|---|---|
| ACUTE PNEUMONIA | 2 | 5.882% | 2 | 5.754% | 5.625% | 5.882% |

Report 4.6          User: LEX

FIGURE 105

Lot Analysis by Owner Report
For Date Range: 07/01/2004 to 08/18/2004

| Lot | Pen | Head Count | In Date | In Weight | # Head Treated | Retreats # | Retreats % | Avg Price | Deads # | Deads % |
|---|---|---|---|---|---|---|---|---|---|---|
| | | | **** Any Feedyard **** | | | | | | | |
| 0 | 606 | 48 | 10/02/2003 | 497 | 0 | 0 | 0.00 | 0.00 | 0 | 0.00 |
| 10 | 307 | 34 | 07/08/2004 | 335 | 2 | 0 | 0.00 | 0.57 | 1 | 2.94 |
| 11 | 304 | 73 | 07/20/2004 | 772 | 0 | 0 | 0.00 | 0.00 | 0 | 0.00 |
| 13 | 601 | 39 | 07/30/2004 | 1234 | 0 | 0 | 0.00 | 0.00 | 0 | 0.00 |
| 20 | 312 | 35 | 08/07/2003 | 340 | 0 | 0 | 0.00 | 0.00 | 1 | 2.86 |
| | 511 | 12 | 08/07/2003 | 340 | 0 | 0 | 0.00 | 0.00 | 0 | 0.00 |
| 322S | 403 | 143 | 01/16/2004 | 571 | 2 | 1 | 0.70 | 0.48 | 1 | 0.70 |
| 388 | 606 | 3 | 10/02/2003 | 412 | 0 | 0 | 0.00 | 0.00 | 0 | 0.00 |
| 389 | 606 | 2 | 10/02/2003 | 496 | 0 | 0 | 0.00 | 0.00 | 0 | 0.00 |
| ** Owner Total | | 389 | | | 4 | 1 | 0.26 | 0.23 | 3 | 0.77 |

Report 4.7      User: LEX

FIGURE 106

Pen Rider Analysis Report
For: 07/01/2004 to 08/18/2004
For Pen Rider: All

| Lot | Pen | TagID | Diagnosis | Death Date | Death Location | 1st Time Pull |
|---|---|---|---|---|---|---|
| | | | Pen Rider: LAST, ADAM | | | |
| 322S | 403 | 322416 | ACUTE PNEUMONIA | 07/12/2004 | Hospital | N |
| 449 | 515 | 449365 | ACUTE PNEUMONIA | 07/01/2004 | Home Pen | Y |
| 450 | 610 | 450231 | ACUTE PNEUMONIA | 07/23/2004 | Home Pen | Y |
| 459N | 105 | 459362 | ACUTE PNEUMONIA | 07/16/2004 | Hospital | N |
| 461N | 507 | 461423 | ACUTE PNEUMONIA | 07/23/2004 | Hospital | Y |
| 461N | 507 | 461297 | ACUTE PNEUMONIA | 07/23/2004 | Hospital | Y |
| 50 | 125 | 505289 | ACUTE PNEUMONIA | 07/22/2004 | Hospital | N |
| 70 | 124 | 701126 | ACUTE PNEUMONIA | 07/17/2004 | Hospital | Y |

Report 4.8                    User: LEX

FIGURE 107

Lot Analysis Report
For 08/18/2004

| Lot | In Wt | DOF | Hd Cnt | Pulled Days Ago | | | | | | | Current Hosp HD | | To Date Hosp HD | | Total Deads | Cost/Hd | |
|---|---|---|---|---|---|---|---|---|---|---|---|---|---|---|---|---|---|
| | | | | 7 | 6 | 5 | 4 | 3 | 2 | 1 | | | | | | Med | Proc |
| 0 | 497 | 322 | 48 | 0 | 0 | 0 | 0 | 0 | 0 | 0 | 0 | 0.0% | 0 | 0.0% | 1 | 0.00 | 0.00 |
| 10 | 335 | 42 | 34 | 0 | 0 | 0 | 0 | 0 | 0 | 0 | 2 | 5.9% | 2 | 5.9% | 1 | 0.00 | 0.00 |
| 11 | 772 | 30 | 73 | 0 | 0 | 0 | 0 | 0 | 0 | 0 | 2 | 2.7% | 2 | 2.7% | 0 | 0.00 | 0.00 |
| 13 | 1234 | 20 | 39 | 0 | 0 | 0 | 0 | 0 | 0 | 0 | 0 | 0.0% | 0 | 0.0% | 0 | 0.00 | 0.00 |
| 20 | 340 | 376 | 174 | 0 | 0 | 0 | 0 | 0 | 0 | 0 | 2 | 1.1% | 6 | 3.4% | 1 | 0.00 | 0.00 |
| 322S | 571 | 216 | 143 | 0 | 0 | 0 | 0 | 0 | 0 | 0 | 2 | 1.4% | 7 | 4.9% | 3 | 0.00 | 0.00 |
| 388 | 412 | 322 | 11 | 0 | 0 | 0 | 0 | 0 | 0 | 0 | 0 | 0.0% | 1 | 9.1% | 0 | 0.00 | 0.00 |
| 389 | 496 | 322 | 2 | 0 | 0 | 0 | 0 | 0 | 0 | 0 | 0 | 0.0% | 1 | 50.0% | 0 | 0.00 | 0.00 |
| 390 | 459 | 321 | 13 | 0 | 0 | 0 | 0 | 0 | 0 | 0 | 0 | 0.0% | 0 | 0.0% | 0 | 0.00 | 0.00 |
| 391S | 638 | 216 | 103 | 0 | 0 | 0 | 0 | 0 | 0 | 0 | 1 | 1.0% | 2 | 1.9% | 0 | 0.00 | 0.00 |
| 40 | 568 | 92 | 130 | 0 | 0 | 0 | 0 | 0 | 0 | 0 | 2 | 1.5% | 4 | 3.1% | 0 | 0.00 | 0.00 |
| 403 | 693 | 156 | 126 | 0 | 0 | 0 | 0 | 0 | 0 | 0 | 5 | 4.0% | 10 | 7.9% | 0 | 0.00 | 0.00 |
| 416 | 542 | 244 | 112 | 0 | 0 | 0 | 0 | 0 | 0 | 0 | 4 | 3.6% | 9 | 8.0% | 3 | 0.00 | 0.00 |
| 420 | 677 | 205 | 77 | 0 | 0 | 0 | 0 | 0 | 0 | 0 | 1 | 1.3% | 4 | 5.2% | 1 | 0.00 | 0.00 |
| 422 | 708 | 188 | 136 | 0 | 0 | 0 | 0 | 0 | 0 | 0 | 2 | 1.5% | 5 | 3.7% | 0 | 0.00 | 0.00 |
| 424 | 594 | 183 | 86 | 0 | 0 | 0 | 0 | 0 | 0 | 0 | 0 | 0.0% | 0 | 0.0% | 0 | 0.00 | 0.00 |
| 425 | 502 | 183 | 1 | 0 | 0 | 0 | 0 | 0 | 0 | 0 | 2 | 100.0% | 3 | 100.0% | 0 | 0.00 | 0.00 |

Report 4.9                                                                                   User: LEX

FIGURE 108

Detail Treatment History By Drug Report
For Lot: 464
As Of: 08/18/2004
Days of History To Display: 90

| **** Processing/Mass Treats **** | | Processing | Days | Drug |
|---|---|---|---|---|
| Lot | Pen | Date | Since Proc | Name |
| 464 | 208 | 08/05/2004 | 13 | COMPEH |
| 464 | 208 | 08/05/2004 | 13 | COMPTH |
| 464 | 208 | 08/05/2004 | 13 | EAR |
| 464 | 208 | 08/05/2004 | 13 | IVERPO |
| 464 | 208 | 08/05/2004 | 13 | PYR 5 |

| **** Individual Treatments **** | | | Treatment | Days | Drug |
|---|---|---|---|---|---|
| Tag ID | Lot | Pen | Date | Since Trtd | Name |
| 464379 | 464 | 208 | 07/19/2004 | 30 | ALBONB |
| 464378 | 464 | 208 | 07/19/2004 | 30 | ALBONB |
| 464407 | 464 | 208 | 08/05/2004 | 13 | BANAMI |
| 464379 | 464 | 208 | 07/19/2004 | 30 | BANAMI |
| 464378 | 464 | 208 | 07/19/2004 | 30 | BANAMI |
| 464379 | 464 | 208 | 07/19/2004 | 30 | LA200 |
| 464378 | 464 | 208 | 07/19/2004 | 30 | LA200 |
| 464407 | 464 | 208 | 08/07/2004 | 11 | NUFLOR |
| 464407 | 464 | 208 | 08/05/2004 | 13 | NUFLOR |
| 464384 | 464 | 208 | 07/28/2004 | 21 | NUFLOR |
| 464384 | 464 | 208 | 07/26/2004 | 23 | NUFLOR |

Report 4.15

User: LEX

FIGURE 109

Manager's Lot Summary Report

| Lot | Date In | Head In | Animals Pulled | 1st Treat | 1st ReTrt | 2nd ReTrt | 3rd ReTrt | 4/More ReTrts | Morbidity Deads | | |
|---|---|---|---|---|---|---|---|---|---|---|---|
| | | | | | | | | | Total | %Pull | %Lot |
| 0 | 10/02/2003 | 48 | 0 | 0 | 0 | 0 | 0 | 0 | 0 | 0.00 | 0.00 |
| 10 | 07/08/2004 | 34 | 2 | 2 | 0 | 0 | 0 | 0 | 0 | 0.00 | 0.00 |
| 11 | 07/20/2004 | 73 | 0 | 0 | 0 | 0 | 0 | 0 | 0 | 0.00 | 0.00 |
| 13 | 07/30/2004 | 39 | 0 | 0 | 0 | 0 | 0 | 0 | 0 | 0.00 | 0.00 |
| 20 | 08/07/2003 | 174 | 3 | 2 | 1 | 0 | 0 | 0 | 0 | 0.00 | 0.00 |
| 322S | 01/16/2004 | 143 | 3 | 2 | 0 | 0 | 1 | 0 | 2 | 66.67 | 1.40 |
| 388 | 10/02/2003 | 11 | 1 | 1 | 0 | 0 | 0 | 0 | 0 | 0.00 | 0.00 |
| 389 | 10/02/2003 | 2 | 0 | 0 | 0 | 0 | 0 | 0 | 0 | 0.00 | 0.00 |
| 390 | 10/03/2003 | 13 | 0 | 0 | 0 | 0 | 0 | 0 | 0 | 0.00 | 0.00 |
| 391S | 01/16/2004 | 103 | 2 | 1 | 1 | 0 | 0 | 0 | 0 | 0.00 | 0.00 |
| 40 | 05/19/2004 | 130 | 4 | 4 | 0 | 0 | 0 | 0 | 0 | 0.00 | 0.00 |
| 403 | 03/16/2004 | 126 | 8 | 8 | 0 | 0 | 0 | 0 | 0 | 0.00 | 0.00 |
| 416 | 12/19/2003 | 112 | 6 | 5 | 1 | 0 | 0 | 0 | 1 | 16.67 | 0.89 |
| 420 | 01/27/2004 | 77 | 2 | 2 | 0 | 0 | 0 | 0 | 1 | 50.00 | 1.30 |
| 422 | 02/13/2004 | 136 | 4 | 2 | 2 | 0 | 0 | 0 | 0 | 0.00 | 0.00 |
| 424 | 02/18/2004 | 86 | 0 | 0 | 0 | 0 | 0 | 0 | 0 | 0.00 | 0.00 |
| 425 | 02/18/2004 | 1 | 2 | 2 | 0 | 0 | 0 | 0 | 0 | 0.00 | 0.00 |
| 425P | 03/22/2004 | 129 | 0 | 0 | 0 | 0 | 0 | 0 | 0 | 0.00 | 0.00 |

Report 4.16      User: LEX

FIGURE 110

| Lot | Pen | Tag | Date/<br>Drug | Weight | Temp/<br>Dosag | Diag | Sev | Treatment | Seq |
|---|---|---|---|---|---|---|---|---|---|
| 10 | | | | | | | | | |
| | 307 | | | | | | | | |
| | | 101449 | | | | | | | |
| | | | 08/08/2004<br>BANAMINE | 385 | 105.5<br>6.0 CC | A<br>Drug Added | | A1 | 1 |
| | | 101518 | | | | | | | |
| | | | 08/01/2004<br>BANAMINE | 335 | 104.5<br>6.0 CC | A<br>Drug Added | | A1 | 1 |
| 40 | | | | | | | | | |
| | 202 | | | | | | | | |
| | | 404 | | | | | | | |
| | | | 08/08/2004<br>BANAMINE | 740 | 105.3<br>12.0 CC | B<br>Drug Added | | B1 | 1 |
| 403 | | | | | | | | | |
| | 129 | | | | | | | | |
| | | 403169 | | | | | | | |
| | | | 08/03/2004<br>ALBON-SR BOLUS | 1,010 | 103.5<br>3.5 Bolus | L<br>Dosage Change | | L3 | 1 |
| | | | 08/03/2004<br>BANAMINE | 1,010 | 103.5<br>16.0 CC | L<br>Drug Added | | L3 | 1 |
| | | 403180 | | | | | | | |
| | | | 08/05/2004<br>SULFADIMETHIZINE | 1,160 | 102.9<br>5.0 Each | L<br>Dosage Change | | L1 | 2 |
| | | 403182 | | | | | | | |
| | | | 08/05/2004<br>SULFADIMETHIZINE | 1,035 | 102.0<br>5.0 Each | L<br>Dosage Change | | L1 | 2 |

Report 5.0                                                     User: LEX

FIGURE 111

Inventory Variance

| Name/<br>Unit | Beginning<br>Units/Value | Received<br>Units/Value | Usage<br>Units/Value | Adjustments<br>Units/Value | Ending<br>Units/Value | Physical<br>Count | Variance |
|---|---|---|---|---|---|---|---|
| 7 WAY<br>Dose | 162.0<br>$3.73 | 0.0<br>$0.00 | 0.0<br>$0.00 | 0.0<br>$0.00 | 162.0<br>$3.73 | 165.0<br>$3.80 | 3.0<br>$0.07 |
| A180<br>CC | 381.0<br>$340.54 | 0.0<br>$0.00 | 0.0<br>$0.00 | 0.0<br>$0.00 | 381.0<br>$340.54 | 370.0<br>$330.71 | ▓▓▓<br>▓▓▓ |
| SULFADIMETHIZINE<br>Each | 9.0<br>$11.85 | 0.0<br>$0.00 | 0.0<br>$0.00 | 0.0<br>$0.00 | 9.0<br>$11.85 | 9.5<br>$12.51 | 0.5<br>$0.66 |
| Report Totals: | $356.12 | $0.00 | $0.00 | $0.00 | $356.12 | $347.01 | ▓▓▓ |

Report 6.0　　　　　　　　　　　　　　　　　　User: LEX

FIGURE 112

Detail Billing Report
For Lot # ALL
For 8/1/2004 to 8/18/2004
Active Lots

Processing/Mass Treatments

| Fin Equiv | Drug Name | Units | Head Count | Total Units | Total Price |
|---|---|---|---|---|---|
| Original Lot: 464 | | | | | |
| Original Pen: 208 | | | | | |
| C EH | COMPONENT E-H | 1.0 DS | 101 | 101.0 | 130.0375 |
| C TH | COMPONENT T-H | 1.0 DS | 101 | 101.0 | 102.9897 |
| EAR | EAR TAG | 1.0 EA | 101 | 101.0 | 36.4105 |
| I PO | IVERMECTIN POUR ON | 38.1 CC | 101 | 3,850.1 | 221.7669 |
| PYR5 | PYRAMID 5 | 1.0 CC | 101 | 101.0 | 124.4017 |
| Animals currently in - lot 464 pen(s): 208 | | | | | |
| | | | | Pen Total | 615.6063 |
| | | | | Lot Total | 615.6063 |
| | | Total cost of processing for date range: | | | 615.6063 |
| | | Total head processed for date range: | | | 101 |
| | | Average cost of processing per head: | | | $6.10 |

Report 7.1  User: LEX

FIGURE 113

INDIVIDUAL TREATMENTS

| Date | Fin Equiv | Drug Name | Units | Price |
|---|---|---|---|---|
| Lot: 10 | | | | |
| Pen: 307 | | | | |
| Tag: 101449 | | | | |
| 08/08/2004 | A180 | A180 | 6.0 CC | 5.3628 |
| | BANA | BANAMINE | 6.0 CC | 1.6056 |
| Tag: 101518 | | | | |
| 08/01/2004 | A180 | A180 | 6.0 CC | 5.3628 |
| | BANA | BANAMINE | 6.0 CC | 1.6056 |
| 08/03/2004 | A180 | A180 | 6.0 CC | 5.3628 |
| | | | Pen Total | 19.2996 |
| | | | Lot Total | 19.2996 |
| Lot: 40 | | | | |
| Pen: 202 | | | | |
| Tag: 404 | | | | |
| 08/08/2004 | BANA | BANAMINE | 12.0 CC | 3.2112 |
| | NUFL | NUFLOR | 23.0 CC | 10.9158 |
| 08/10/2004 | NUFL | NUFLOR | 22.0 CC | 10.4412 |
| | | | Pen Total | 24.5682 |
| | | | Lot Total | 24.5682 |

Report 7.1

FIGURE 114

Quality Assurance Report
All Transactions for Lot 464
Date Closed 08/18/2004

Processing/Mass Treatments

| Date | Drug Name | Head | Dosage | Total Amount |
|---|---|---|---|---|
| 08/05/2004 | COMPONENT E-H | 101 | 1.0 Dose | 101.0 Dose |
| | COMPONENT T-H | 101 | 1.0 Dose | 101.0 Dose |
| | EAR TAG | 101 | 1.0 Each | 101.0 Each |
| | IVERMECTIN POUR ON | 101 | 38.1 CC | 3,850.1 CC |
| | PYRAMID 5 | 101 | 1.0 CC | 101.0 CC |

Animals were processed in Lot 464 Pen 208
Animals currently in - lot 464 pen(s): 208

Individual Treatments
Pen: 208

| Tag # | Date | Drug Name | Amount | |
|---|---|---|---|---|
| 464378 | 07/19/2004 | LIQUAMYCIN | 35.0 | CC |
| | | ALBON-SR BOLUS | 3.0 | Bolus |
| | | BANAMINE | 11.0 | CC |
| 464379 | 07/19/2004 | LIQUAMYCIN | 40.0 | CC |
| | | ALBON-SR BOLUS | 4.0 | Bolus |
| | | BANAMINE | 12.0 | CC |
| 464384 | 07/26/2004 | NUFLOR | 26.0 | CC |
| | 07/28/2004 | NUFLOR | 27.0 | CC |
| 464407 | 08/05/2004 | NUFLOR | 25.0 | CC |
| | | BANAMINE | 13.0 | CC |
| | 08/07/2004 | NUFLOR | 24.0 | CC |

Report 8.0                                     User: LEX

FIGURE 115

Morbidity Report
Summary of Treatments, Diagnoses, Deads and Movements
For Treatment Date Range: 7/30/2004 to 8/7/2004
Active Lots

| | Number of Animals | % of Total | Average Days Treated | Average Days on Feed |
|---|---|---|---|---|
| Treatments | | | | |
| | 27 Animals Treated | | 2 | 90 |
| | 21 First Time Treats | | 2 | 92 |
| | 6 Retreats | | 4 | 82 |
| | 3 Treated More Than 3 Days | | 5 | 119 |
| Diagnosis Breakdown | | | | |
| | 1 BLOAT | 3.4% | 1 | 34 |
| | 1 C-SECTION | 3.4% | 1 | 160 |
| | 1 PINKEYE | 3.4% | 1 | 30 |
| | 2 ACUTE PNEUMONIA | 6.9% | 1 | 23 |
| | 4 FROTHY PNEUMONIA | 13.8% | 1 | 89 |
| | 5 FOOTROT | 17.2% | 1 | 119 |
| | 15 CHRONIC PNEUMONIA | 51.7% | 1 | 79 |
| Deads | | | | |
| | 2 Home Pen | 40.0% | 0 | 23 |
| | 2 Hospital | 40.0% | 2 | 98 |
| | 1 Recovery | 20.0% | 1 | 231 |

Movements

| From: \ To: | Buller | Chronic | Hospital | Pasture | Railer | Recovery | Regular |
|---|---|---|---|---|---|---|---|
| Buller | ■ | | | | | | |
| Chronic | | ■ | | | | | |
| Hospital | | | ■ | | | 26 | |
| Pasture | | | | ■ | | | |
| Railer | | | | | ■ | | |
| Recovery | 4 | | 1 | | | ■ | 46 |
| Regular | | | 27 | | | | ■ |

Report 10.1                                    User: LEX

FIGURE 116

Morbidity Report
Disease/Treatments Summary
For Treatment Date Range: 7/30/2004 to 8/18/2004
Active Lots

| Diagnosis | Treatment | Day | Number of Treatments | Average Weight | Average Temp | Average Cost |
|---|---|---|---|---|---|---|
| ACUTE PNEUMONIA | A1 | 1 | 12 | 530 | 104.6 | $ 0.00 |
|  |  | 3 | 6 | 540 | 101.8 | $ 0.00 |
| BLOAT | H | 1 | 1 | 690 | 102.2 | $ 0.00 |
| CHRONIC PNEUMONIA | B1 | 1 | 19 | 823 | 104.5 | $ 0.00 |
|  |  | 3 | 18 | 741 | 101.4 | $ 0.00 |
| C-SECTION | Q1 | 1 | 1 | 345 | 102.5 | $ 0.00 |
| FOOTROT | L1 | 1 | 2 | 1,083 | 102.9 | $ 0.00 |
|  |  | 2 | 3 | 1,092 | 102.0 | $ 0.00 |
|  | L3 | 1 | 2 | 833 | 103.3 | $ 0.00 |
| FROTHY PNEUMONIA | C1 | 1 | 3 | 1,017 | 102.6 | $ 0.00 |
|  | C2 | 1 | 6 | 956 | 103.0 | $ 0.00 |

Report 10.2  User: LEX

FIGURE 117

Morbidity Report
Treatment Detail for Date by Origin
From 8/1/2004 to 8/18/2004
Lot # ALL
Active Lots

|  | Diagnosis/Treatment | Sev | Seq | Weight | Temp | Pen Rider |
|---|---|---|---|---|---|---|
| Origin: | | | | | | |
| Lot: 10 | | | | | | |
| Pen: 307 | | | | | | |
| Tag: 101449 | | | | | | |
| | ACUTE PNEUMONIA | | 1 | 385 | 105.5 | |
| 8/8/2004 | A1 | A180 | | | | 6.0 CC |
| | | BANAMINE | | | | 6.0 CC |
| Tag: 101518 | | | | | | |
| | ACUTE PNEUMONIA | | 1 | 335 | 104.5 | |
| 8/1/2004 | A1 | A180 | | | | 6.0 CC |
| | | BANAMINE | | | | 6.0 CC |
| | ACUTE PNEUMONIA | | 3 | 345 | 101.0 | |
| 8/3/2004 | A1 | A180 | | | | 6.0 CC |
| Lot: 40 | | | | | | |
| Pen: 202 | | | | | | |
| Tag: 404 | | | | | | |
| | CHRONIC PNEUMONIA | | 1 | 740 | 105.3 | |
| 8/8/2004 | B1 | NUFLOR | | | | 23.0 CC |
| | | BANAMINE | | | | 12.0 CC |
| | CHRONIC PNEUMONIA | | 3 | 730 | 102.3 | |
| 8/10/2004 | B1 | NUFLOR | | | | 22.0 CC |

Report 10.7      User: LEX

FIGURE 118

Mortality Summary Report
From 08/01/2004 to 08/18/2004
Active Lots
Lot # ALL

| Number of Animals | Average Days Treated | Average Days On Feed | Percentages |
|---|---|---|---|
| 5 Animals Dead for Period | 1 | 94 | 0.08% of 6,250 |
| 2 Deads in Home Pen | 0 | 23 | 40.00% of Deads |
| 2 Deads in Hospital | 2 | 98 | 40.00% of Deads |
| 1 Deads in Recovery | 1 | 231 | 20.00% of Deads |
| 0 Deads in pens treated previously | | | |
| Diagnosis Breakdown | | | |
| 1 BULLER | 1 | 231 | 0.00% in Hospital |
| | | | 0.00% in Home Pen |
| | | | 100.00% in Other |
| 3 CHRONIC PNEUMONIA | 0 | 26 | 33.33% in Hospital |
| | | | 66.67% in Home Pen |
| | | | 0.00% in Other |
| 1 FROTHY PNEUMONIA | 4 | 162 | 100.00% in Hospital |
| | | | 0.00% in Home Pen |
| | | | 0.00% in Other |

Report 11.1               User: LEX

FIGURE 119

Lot: 10
   Pen: 307
      Tag: 101546

| Date | Diagnosis | Weight | Temp | Sev | Pen Rider | Origin | To Pen |
|---|---|---|---|---|---|---|---|
| | ** | | | | | | |

Died 08/04/2004 of CHRONIC PNEUMONIA in Home Pen
Days on feed: 28
Total price of treatments:

Lot: 416
   Pen: 112
      Tag: 41616

| Date | Diagnosis | Weight | Temp | Sev | Pen Rider | Origin | To Pen |
|---|---|---|---|---|---|---|---|
| 07/31/2004 | FROTHY PNEUMONIA | 908 | 103.2 | | | | H3 |
| | CEFTIOFUR SODIUM | | | | 14.0 CC | | |

Died 08/05/2004 of BULLER in Recovery
Days on feed: 231
Total price of treatments: $7.63

Comments: WATER BELLY??

Report 11.5        User: LEX

FIGURE 120

Home Lot #: 462N        Home Pen #: 106

Tag Number: 4627

Date of Death: Monday, August 2, 2004

Reason for Death: CHRONIC PNEUMONIA

Location of Death: Hospital

Remarks
BLOAT

| Signature of Feedlot Official | |
|---|---|

FIGURE 121

Drugs
Active Items

| Short Name | Name | Type | Trans | Dose/ 100 Wt | Std Dose | Max Dose | Units | Round to Nearest |
|---|---|---|---|---|---|---|---|---|
| 7WAY | 7WAY | P | | 0.0 | 2.0 | | DS | 1.0 |
| 7WAY S | 7WAY/SOMNUS | P | | | 5.0 | | DS | 1.0 |
| A180 | A180 | T | | 1.5 | | | CC | 1.0 |
| ADSPEC | ADSPEC | T | | 5.5 | | | CC | 1.0 |
| AGRI B | SULFADIMETHIZINE | T | | | 1.0 | | EA | 1.0 |
| ALBONB | ALBON-SR BOLUS | T | | 0.5 | 0.0 | 6.0 | BOL | 1.0 |
| ALBONI | SULFADIMETHOXINE | T | | 6.2 | | | CC | 1.0 |
| B COMP | VITAMIN B COMPLEX | T | | 2.0 | | | CC | 1.0 |
| B1 | VIT B1 | T | | 2.0 | | | CC | 1.0 |
| B100 | BAYTRIL 100 | T | | 4.0 | | | CC | 1.0 |
| B12 | CYANOCOBALAZIN | T | | | 5.0 | | DS | 1.0 |
| B4L5 | VAC 4 + LEPTO 5 | P | | | 2.0 | | DS | 1.0 |
| BANAMI | BANAMINE | T | | 1.5 | | | CC | 1.0 |
| BANDS | BANDING LOOPS | T | | | 1.0 | | EA | 1.0 |
| BATTLE | BATTLE DRENCH | T | | 1.0 | | | OZ | 1.0 |
| BLUE | BLUE LYTE | T | | | 1.0 | | EA | 1.0 |

User: LEX

T - Treatment Drug
P - Processing Drug
B - Treatment/Processing Drug

FIGURE 122

| In Date | DOF | Proj. Ship | Customer Name | Sex | In Wt. | Head Count | Deads |
|---|---|---|---|---|---|---|---|
| Lot: 0 | | | | | | | |
| Pen: 606 | | | | | | | |
| 10/02/2003 | 322 | | SUE FRANK JOHN CUSTOMER 10 | M | 497 | 45 | 1 |
| | | | Total for lot 0 | | | 45 | 1 |
| Lot: 10 | | | | | | | |
| Pen: 307 | | | | | | | |
| 07/08/2004 | 42 | | JIM SMITH | H | 335 | 33 | 1 |
| | | | Total for lot 10 | | | 33 | 1 |
| Lot: 11 | | | | | | | |
| Pen: 304 | | | | | | | |
| 07/20/2004 | 30 | | SPEEDY | H | 772 | 73 | 0 |
| | | | Total for lot 11 | | | 73 | 0 |
| Lot: 13 | | | | | | | |
| Pen: 601 | | | | | | | |
| 07/30/2004 | 20 | | FEEDYARD 1 | C | 1,234 | 39 | 0 |
| | | | Total for lot 13 | | | 39 | 0 |
| Lot: 20 | | | | | | | |
| Pen: 309 | | | | | | | |
| 08/14/2003 | 371 | | JIM SMITH | H | 340 | 0 | 0 |
| Pen: 311 | | | | | | | |
| 08/07/2003 | 378 | | JIM SMITH | H | 340 | 22 | 0 |
| Pen: 312 | | | | | | | |
| 08/07/2003 | 378 | | JIM SMITH | H | 340 | 34 | 1 |
| Pen: 413 | | | | | | | |
| 08/07/2003 | 378 | | JIM SMITH | H | 340 | 27 | 0 |
| Pen: 511 | | | | | | | |
| 08/07/2003 | 378 | | JIM SMITH | H | 340 | 12 | 0 |
| Pen: 514 | | | | | | | |
| 08/07/2003 | 378 | | JIM SMITH | H | 340 | 2 | 0 |
| Pen: 612 | | | | | | | |
| 08/07/2003 | 378 | | JIM SMITH | H | 340 | 5 | 0 |
| | | | Total for lot 20 | | | 102 | 1 |

Report 12.3  User: LEX

FIGURE 123

|  | Drug | Dosage/100 | Std Dosage | Units |
|---|---|---|---|---|
| Diagnosis: A ACUTE PNEUMONIA | | | | |
| Treatment: A0 | | | | |
| Day 1 | OBSRV | 0.00 | 0.00 | Each |
| Treatment: A1 | | | | |
| Day 1 | A180 | 1.50 | 0.00 | CC |
| Day 3 | A180 | 1.50 | 0.00 | CC |
| Treatment: A2 | | | | |
| Day 1 | ALBONI | 6.20 | 0.00 | CC |
|  | TYLAN | 4.00 | 0.00 | CC |
| Treatment: A3 | | | | |
| Day 1 | NAX | 1.50 | 0.00 | CC |
| Day 2 | NAX | 1.50 | 0.00 | CC |
| Day 3 | NAX | 1.50 | 0.00 | CC |
| Treatment: A4 | | | | |
| Day 1 | MIC | 2.00 | 0.00 | CC |
| Treatment: A5 | | | | |
| Day 1 | ADSPEC | 5.50 | 0.00 | CC |
| Treatment: A6 | | | | |
| Day 1 | NAX | 1.50 | 0.00 | CC |
|  | POLY | 2.00 | 0.00 | CC |
| Treatment: A7 | | | | |
| Day 1 | BANAMI | 1.50 | 0.00 | CC |
| Diagnosis: B CHRONIC PNEUMONIA | | | | |
| Treatment: B0 | | | | |
| Day 1 | OBSRV | 0.00 | 0.00 | Each |
| Treatment: B1 | | | | |
| Day 1 | NUFLOR | 3.00 | 0.00 | CC |
| Day 3 | NUFLOR | 3.00 | 0.00 | CC |
| Treatment: B2 | | | | |
| Day 1 | BLUE | 0.00 | 1.00 | Each |
|  | NAX | 1.50 | 0.00 | CC |
|  | POLY | 2.00 | 0.00 | CC |
| Treatment: B3 | | | | |
| Day 1 | NAX | 1.50 | 0.00 | CC |
| Day 2 | NAX | 1.50 | 0.00 | CC |
| Day 3 | NAX | 1.50 | 0.00 | CC |

Report 12.4    User: LEX

FIGURE 124

| Due Date | Lot # Pen # | Type Pen Count | Out Date | Lot Count | DOF | Sex | Customer Name |
|---|---|---|---|---|---|---|---|
| 08/23/2004 | 447 123 | PROC1 114 | 12/1/04 | 114 | 104 | H | ANY FEEDYARD |
| 08/23/2004 | 448 602 | PROC1 37 | 12/1/04 | 37 | 104 | H | ANY FEEDYARD |
| 08/25/2004 | 40 202 | PROC1 130 | 1/16/05 | 130 | 99 | H | LEXTRON FEEDYARD |
| Comments: Established via Bunk Reader | | | | | | | |

Report 12.6    User: LEX

FIGURE 125

| Orig Lot: 426 | Orig Pen: 203 | | Sex: H | DOF: 79 |
|---|---|---|---|---|
| In Date: 05/12/2004 | Out Date: 11/05/2004 | | Treat Date: 07/29/2004 | Average Weight: 965 |
| Customer: CUSTOMER 8 | | | | |
| Drug | | Head Cnt | Dosage | Usage Serial Number |
| COMPONENT E-H | | 81 | 1.0 Dose | 81.0 |
| COMPONENT T-H | | 81 | 1.0 Dose | 81.0 |
| Animals currently in - lot 426 pen(s): 203 | | | | |
| Lot Comments: | | | | |
| Orig Lot: 427 | Orig Pen: 308 | | Sex: M | DOF: 78 |
| In Date: 05/10/2004 | Out Date: 11/01/2004 | | Treat Date: 07/26/2004 | Average Weight: 919 |
| Customer: SIFI | | | | |
| Drug | | Head Cnt | Dosage | Usage Serial Number |
| COMPONENT E-H | | 68 | 1.0 Dose | 68.0 |
| COMPONENT T-H | | 68 | 1.0 Dose | 68.0 |
| IVERMECTIN POUR ON | | 68 | 0.0 CC | 0.0 |
| Animals currently in - lot 427 pen(s): 308 | | | | |
| Lot Comments: Established via Bunk Reader | | | | |

Report 12.7    User: LEX

FIGURE 126

Active Diagnosis Codes

| Diagnosis Code | Description | Financial System Death Code Equivalent | Diagnosis Class Code |
|---|---|---|---|
| A | ACUTE PNEUMONIA | | RESPIRATORY |
| B | CHRONIC PNEUMONIA | | RESPIRATORY |
| C | FROTHY PNEUMONIA | | RESPIRATORY |
| D | MISCELLANIOUS | | OTHER |
| E | DIPTHERIA/HONKER | | RESPIRATORY |
| F | HONKER | | RESPIRATORY |
| G | DIGESTIVE | | DIGESTIVE |
| H | BLOAT | | DIGESTIVE |
| I | ACIDOSIS | | DIGESTIVE |
| J | COCCIDIOSIS | | DIGESTIVE |
| K | BOWEL OBSTRUCTION | | OTHER |
| L | FOOTROT | | OTHER |
| M | ACUTE PNEUMONIA 2 | | RESPIRATORY |
| N | VAGINAL PROLAPSE | | OB/GYN |
| O | CALVER/ABORTION | | OB/GYN |
| OB | OBSERVE | | OTHER |
| P | RETAINED PLACENTA/METRI | | OB/GYN |
| PROC | PROCESSING | | OTHER |
| Q | C-SECTION | | OB/GYN |
| R | RETREAT | | OTHER |
| S | WATER BELLEY | | OTHER |
| T | LAMENESS/INJURY | | MUSCLE/SKELETAL |
| U | PINKEYE | | OTHER |
| V | NEUROLOGIC | | OTHER |
| W | BULLER | | OTHER |
| X | ABSCESS | | OTHER |
| Y | SOLE/HOOF SEP. (SBS) | | OTHER |
| Z | MISC. EYE PROBLEMS | | OTHER |

Report 12.14                              User: LEX

FIGURE 127

Weight Gain Report
For Lot #
Active Lots
As Of 08/18/2004

| Lot | Pen | | Tag # | Weight Gain | Weight | Date Last Weighed |
|---|---|---|---|---|---|---|
| 20 | 311 | | 209346 | 0.000 | 340 | 05/28/2004 |
| | | | 209363 | 31.071 | 775 | 05/13/2004 |
| | Pen Averages: | Total Head Count= | 2 | | | |
| | | Average Weight= | 558 | | | |
| | | Average Weight Gain= | 15.536 | | | |
| | 312 | | 209379 | 6.667 | 900 | 06/28/2004 |
| | Pen Averages: | Total Head Count= | 1 | | | |
| | | Average Weight= | 900 | | | |
| | | Average Weight Gain= | 6.667 | | | |
| | Lot Averages: | Total Head Count= | 3 | | | |
| | | Average Weight= | 672 | | | |
| | | Average Weight Gain= | 12.579 | | | |

Report 12.15    User: LEX

FIGURE 128

Implant Status Codes

| Status Code | Description |
|---|---|
| ABS | ABCESS |
| BUNCH | BUNCHED |
| CRUSH | CRUSHED |
| IMPROP | IMPROPER LOCATION |
| INCART | IN CARTILAGE |
| MSABS | MISSING - ABCESS |
| MSUNK | MISSING - UNKNOWN |
| PART | PARTIALLY MISSING |
| PROP | PROPER |
| WALL | WALLING OFF |

Report 12.18    User: LEX

FIGURE 129

Railer Summary Report
From 08/01/2004 to 08/19/2004
Active Lots
Lot # ALL

| Number of Animals | | Average Days Treated | Average Days On Feed | Percents | |
|---|---|---|---|---|---|
| 3 | Animals Railed for Period | 0 | 35 | 0.04% | of 8096 |
| 1 | Railers Shipped | 0 | 35 | 33.33% | of Railers |
| 0 | Railers Treated Previously | 0 | 0 | 0.00% | of Railers |
| Diagnosis Breakdown | | | | | |
| 1 | ACUTE PNEUMONIA | 0 | 35 | 0.00% 100.00% | Shipped In Pens |
| 1 | MISCELLANIOUS | 0 | 35 | 100.00% 0.00% | Shipped In Pens |
| 1 | DIGESTIVE | 0 | 35 | 0.00% 100.00% | Shipped In Pens |

Report 13.1     User:LEX

FIGURE 130

Railer Analysis (Cause/DOF) Report
From 08/01/2004 to 08/19/2004
Active Lots
Lot # ALL

| Cause | | Days on Feed | | | | | | Total | Shipped | Rail Pen |
|---|---|---|---|---|---|---|---|---|---|---|
| | | 0-7 | 8-25 | 26-45 | 46-90 | 91-150 | 151+ | | | |
| A | ACUTE PNEUMONI | 0 | 0 | 1 | 0 | 0 | 0 | 1 | 0 | 1 |
| D | MISCELLANIOUS | 0 | 0 | 1 | 0 | 0 | 0 | 1 | 1 | 0 |
| G | DIGESTIVE | 0 | 0 | 1 | 0 | 0 | 0 | 1 | 0 | 1 |
| ** Totals ** | | 0 | 0 | 3 | 0 | 0 | 0 | 3 | 1 | 2 |

Report 13.2                    User: LEX

FIGURE 131

Railer Notification Slip
For 8/1/2004 12:00:00AM to 8/19/2004 11:59:59PM
Lot # ALL

| | |
|---|---|
| Home Lot # 464 | Home Pen # 208 |
| Tag Number | 43213 |
| Rail Date | 08/19/2004 |
| Reason For Railer | DIGESTIVE |
| Location of Railer | 104 |

Signature of Feedlot Official _____

Report 13.5                                   User: LEX

FIGURE 132

Cattle Activity - Receivings Report
For: 07/01/2004 to 07/31/2004
Active & Inactive Lots

| Date Rcvd. | Lot Number | Pen Number | Head Rcvd. |
|---|---|---|---|
| 07/01/2004 | | | |
| | 462N | 106 | 152 |
| | | Total For Date 07/01/2004 | 152 |
| 07/02/2004 | | | |
| | 99 | 119 | 75 |
| | | 119 | 150 |
| | | Total For Lot 99 | 225 |
| | | Total For Date 07/02/2004 | 225 |
| 07/03/2004 | | | |
| | 10 | 113 | 13 |
| | 10 | N1 | 13 |
| | | Total For Date 07/03/2004 | 26 |
| 07/14/2004 | | | |
| | 76 | 118 | 71 |
| | | Total For Date 07/14/2004 | 71 |
| 07/16/2004 | | | |
| | 443 | 127 | 88 |
| | 452 | 313 | 90 |
| | 463N | 418 | 62 |
| | 464 | 208 | 101 |
| | | Total For Date 07/16/2004 | 341 |
| 07/18/2004 | | | |
| | 10 | N1 | 21 |
| | 465N | 402 | 73 |
| | | Total For Date 07/18/2004 | 94 |

Report 39  User: LEX

FIGURE 133

Cattle Activity - Movements Report
For: 7/1/2004 to 7/31/2004
Active & Inactive Lots

| Date From Pen | From Lot | To Pen | To Lot | Head |
|---|---|---|---|---|
| 07/01/2004 | | | | |
| 103 | 457 | H1 | | 1 |
| 202 | 40 | H1 | | 1 |
| 416 | 449 | *DEAD* | | 1 |
| H1 | 70 | 417 | | 2 |
| H3 | 422 | H5 | | 1 |
| | | Total For | 07/01/2004 | 6 |
| 07/02/2004 | | | | |
| 102 | 419 | *DEAD* | | 1 |
| 111 | 422 | 418 | | 1 |
| 112 | 416 | H1 | | 1 |
| 119 | 99 | 118 | | 150 |
| 127 | 50 | 511 | | 20 |
| 127 | 50 | 612 | | 17 |
| 127 | 60 | 612 | | 71 |
| 310 | 460 | H1 | | 1 |
| 418 | 24 | 601 | | 1 |
| 418 | 388 | 406 | | 1 |
| 418 | 420 | 300 | | 1 |
| 418 | 428 | 613 | | 3 |
| 418 | 429 | 300 | | 1 |
| 418 | 432 | 300 | | 1 |
| 418 | 435 | 109 | | 1 |
| 418 | 437 | 303 | | 1 |
| 418 | 440 | 513 | | 2 |
| 418 | 441 | 412 | | 1 |
| 418 | 446 | 408 | | 5 |
| 418 | 447 | 409 | | 1 |
| 418 | 448 | 602 | | 1 |
| 418 | 449 | 416 | | 2 |
| 418 | 452 | 300 | | 1 |
| 418 | 454 | 506 | | 1 |
| 418 | 455 | 300 | | 1 |
| 514 | 20 | 612 | | 32 |
| 612 | 90 | 511 | | 10 |
| H1 | 24 | H3 | | 1 |
| H1 | 458 | 417 | | 1 |
| H1 | 459N | 417 | | 1 |
| H1 | 459N | H3 | | 1 |
| H3 | 459N | 417 | | 1 |
| N2 | 24 | 601 | | 1 |
| | | Total For | 07/02/2004 | 335 |
| 07/03/2004 | | | | |
| 130 | 432 | H1 | | 1 |
| 202 | 40 | H1 | | 1 |

Report 40  User: LEX

FIGURE 134

Cattle Activity - Deads Report
For: 07/01/2004 to 07/12/2004
Active & Inactive Lots

| Death Date | Home Pen | Lot Number | Count | Death Loc. |
|---|---|---|---|---|
| 07/01/2004 | | | | |
| | 416 | 449 | 1 | HP |
| | | Total for 07/01/2004 | 1 | |
| 07/02/2004 | | | | |
| | 102 | 419 | 1 | HP |
| | | Total for 07/02/2004 | 1 | |
| 07/03/2004 | | | | |
| | 312 | 20 | 1 | HP |
| | H3 | 70 | 1 | H |
| | | Total for 07/03/2004 | 2 | |
| 07/08/2004 | | | | |
| | H5 | 12 | 1 | H |
| | | Total for 07/08/2004 | 1 | |
| 07/12/2004 | | | | |
| | H3 | 322S | 1 | H |
| | | Total for 07/12/2004 | 1 | |

Grand Total    5

Report 41      User: LEX

FIGURE 135

Cattle Activity - Shipments Report
For: 07/01/2004 to 07/13/2004
Active & Inactive Lots

| Date Shipped | Lot Number | Pen Number | Head Shipped |
|---|---|---|---|
| 07/05/2004 | 416 | 112 | 40 |
| | Total For Date | 7/5/04 | 40 |
| 07/06/2004 | 10 | 113 | 13 |
| | 420 | 105 | 43 |
| | Total For Date | 7/6/04 | 56 |
| 07/07/2004 | 422 | 111 | 45 |
| | 90 | 413 | 37 |
| | 99 | 118 | 75 |
| | Total For Date | 7/7/04 | 157 |
| 07/08/2004 | 439 | 302 | 1 |
| | Total For Date | 7/8/04 | 1 |
| 07/12/2004 | 417 | 307 | 45 |
| | 431 | 110 | 45 |
| | Total For Date | 7/12/04 | 90 |
| 07/13/2004 | 422 | 111 | 43 |
| | 99 | 118 | 75 |
| | Total For Date | 7/13/04 | 118 |

Report 42 User: LEX

FIGURE 136

Pen Master Listing
As Of : 08/18/2004
Pen Type :ALL Sex :ALL
Sorted By: PEN

| Pen | Pen Type | Sex | Delivery Zone/Seq | Call Zone/Seq | In Date | Projected Ship Date | Lot | Head In Pen | Not In Pen | Spcl Head |
|---|---|---|---|---|---|---|---|---|---|---|
| 102 | R | | /4 | /4 | | | | EMPTY | | |
| 103 | R | N | /5 | /5 | 05/27/2004 | 01/18/2005 | 457 | 87 | 2 | |
| 104 | R | | /6 | /6 | | | | EMPTY | | |
| 105 | R | S | /7 | /7 | 01/27/2004 | | 420 | 0 | 3 | |
| | | | | | 06/28/2004 | | 459N | 97 | 2 | |
| | | | | Pen Totals | | | | 97 | 5 | |
| 106 | R | S | /8 | /8 | 07/01/2004 | | 462N | 144 | 7 | |
| 107 | R | | /9 | /9 | | | | EMPTY | | |
| 108 | R | | /10 | /10 | | | | EMPTY | | |
| 109 | R | H | /11 | /11 | 03/18/2004 | 08/15/2004 | 435 | 70 | 0 | |
| 110 | R | H | /12 | /12 | 03/16/2004 | 07/10/2004 | 431 | 0 | 1 | |
| 111 | R | S | /13 | /13 | 02/13/2004 | | 422 | 0 | 2 | |
| 112 | R | S | /14 | /14 | 12/19/2003 | 07/15/2004 | 416 | 20 | 1 | |
| 113 | R | | /15 | /15 | | | | EMPTY | | |
| ... | | | | | | | | | | |

Report 49.1     User: LEX

FIGURE 137

CATTLE MANAGEMENT SYSTEM AND METHOD

CROSS-REFERENCE TO RELATED APPLICATION

This Application claims the priority of U.S. Provisional Application No. 60/609,914 filed on Sep. 14, 2004, the entire disclosure of which is hereby incorporated by reference.

FIELD OF THE INVENTION

The present invention relates to the management of animals such as cattle during the production life cycle of the cattle, and more particularly, to processes and data management systems that allow management of cattle on an individual basis from the time an animal is born until the animal is slaughtered.

BACKGROUND OF THE INVENTION

Automation in the cattle industry has been established by various cattle management systems that track cattle at various stages within a production cycle. These systems have been developed in response to economic factors in the industry demanding more efficient and cost effective cattle management. In these systems, data is gathered and processed to allow cattle industry personnel to improve their return on investment.

One prior art example of a cattle management system is disclosed in the U.S. Pat. No. 5,673,647. This reference specifically discloses an automation system for individual animal electronic identification, measurement and value based management of cattle in a feed lot operation. The invention utilizes a computer system integrated with automatic individual animal identification, multiple measurement and re-measurement systems, and a cattle handling and sorting system. Animals are individually identified and measured by weight, and external dimensions and characteristics of internal body tissue are taken. This information is coupled with animal physiological characteristics and historical data allowing the calculation of an optimum slaughter weight, economic endpoint, and marketing date for shipment to a packing plant. After measurement, individual animals are sorted in response to calculations from the measurements. The computer system also calculates each animal's share of total feed intake for the animal's feed group. The computer system stores individual animal measurement, performance and location data, which is used by feed lot management to select animals for shipment from the feed lot for slaughter at the optimum time. Following an animal shipment to a slaughter facility, the identification in the computer system is used to correlate live animal physical characteristics and performance data to the measured and evaluated carcass characteristics data obtained through the slaughter process. Accordingly, a database can be built to more accurately identify and measure value based characteristics and subsequent animals produced and fed for more effective value based selection and management of the animals.

While this reference may disclose a cattle management system for a feed lot operation, the feed lot operation is but just one operation which is included within the overall production life cycle of cattle. More broadly, the cattle industry can be conceptually broken down into two major components, namely, producers and feed lots. The cattle producers include ranch operations that maintain cow herds. The herds produce calves that are raised and typically fed on pasture grazing land. The calves are allowed to reach a certain maturity, and the next phase in cultivation of the cattle is transfer to a feed lot where they are fed on grain and other products until they reach an optimum size for slaughter. Prior to transfer to a feed lot, cattle may also be transported to grower operations where the cattle undergo intensive management for achieving desired growth. The feed lot can be considered a final processing phase prior to slaughter where not only do the animals achieve optimum size for slaughter, but also are closely monitored for diseases or other physical ailments which would prevent them from being timely slaughtered.

Recently, proposed reporting requirements have been developed in the form of a federal unique animal identification and premise identification program. Although this program has not become formalized in federal or state regulations, it is anticipated that the proposed federal program will require that each animal be individually identified by a unique animal identifier which will be used to track each animal from farm to market and market to slaughter. Additionally, identification programs may require a premise identifier for purposes of identifying the premise of origin wherein each production unit (e.g., each ranch operation) would be assigned a unique identifier. Accordingly, the premise number and animal number could be used to record and track all aspects of a production cycle for each animal. This nationwide animal identification system has been primarily prompted by a concern over increased animal disease outbreaks around the globe and public interest in developing an identification program for protecting animal health.

Therefore, a need has developed for a comprehensive data management system where data can be gathered and processed concerning not only the economic factors important to determining return on investment, but also for complying with proposed regulations concerning animal health. More specifically, in order for compliance to be achieved with respect to a national unique animal identification reporting program, a system must exist that provides absolute certainty in identifying an animal during any stage of its production life cycle, thereby necessitating that animal identification be achieved without loss of identification through a tagging device that becomes inadvertently separated from the animal. There are many cattle tagging systems in existence that rely on external or internal tagging devices that can be verified visually or by an electronic reading device. For example, an RFID tag may be attached externally or internally to an animal; however, this type of tagging device can become separated from the animal thereby resulting in the inability to continuously monitor the particular animal.

There is also a need for an integrated data processing system that is based upon centralized storage of information about animals to be monitored, thereby allowing various personnel in the cattle industry to more easily access, transfer and process the data. Currently, many prior art systems incorporate data gathering at various levels in the production cycle of an animal. Data transfer is made more difficult in these systems since data is generated and stored at many different locations and in many different formats. In other words, information gathering and processing is currently very compartmentalized wherein each feed lot, grower, or producer may have their own identification system that does not allow for easy import or export of data.

SUMMARY OF THE INVENTION

In accordance with the present invention, a data processing system is provided that allows for data gathering, transfer and processing throughout the entire production cycle of individual animals. Some significant functionality of the present system includes the ability to track the location of each individual animal by utilizing unique identification data for each animal, recording all monitored events that take place at each location during the animal's production cycle, and reporting the events and locations as required to government entities, financial institutions, and other entities within the cattle industry. Additional functionality of the present system includes the ability to send and receive location and event data concerning each animal between the data processing system of the present invention and external data processing systems at any phase during an animal production cycle. The ability to achieve the above functionality is enhanced by incorporating storage of information either at feedlot locations, or at a single central database. For example, the location history, treatment history, processing history, and any other significant events that are experienced by the animal can be recorded by the present invention and stored either at feedlot locations or at a central database to accommodate necessary data transfer or manipulation.

The data entered into the system can be achieved on a multiple facility basis, and unique reports can be generated at each level or facility based upon parameters chosen for reporting.

The data processing of the present invention includes a computer software program that can be conceptually broken down into two main modules or sections. The first module is referred to herein as the cow/calf module or ranch module, and the second module is referred to as the grower/feed lot operation module. The grower/feed lot module can be further broken down into various sub-modules including animal health, feed management, animal inventory, drug/commodity inventory, data file maintenance, data interfaces, and data reporting.

Although the present invention contemplates various known methods for tagging an animal, the preferred method is to incorporate retinal imaging identification. As understood by those skilled in the art, retinal imaging systems exist that provide reliable identification through retinal scanning as each animal has a unique retinal pattern serving the basis for absolute identification. One company that provides retinal imaging solutions for the cattle industry is Optibrand Ltd., LLC of Fort Collins, Colo.

In the cow/calf module of the present invention as discussed further below, data is generated, stored, manipulated and transferred based on basic activities occurring at a cow/calf operation. Each of these activities involves actions of an individual animal or groups of animals. These activities can be summarized as follows:

a. Cattle receiving—This term refers to animals being brought into a particular cow/calf operation periodically for various reasons such as to increase a particular herd, modify particular characteristics of a herd, etc.
  b. Inventory receiving—This term refers to the receipt of various supplies including medication, equipment, and the like that are used in a cow/calf operation. Receipt and use of these supplies at least requires an inventory function, and may also require tracking of how the supplies are administered to cattle, particularly with respect to medications.
  c. Processing—This term refers generally to the standard or routine actions that take place with respect to introduction of an animal to the herd either through a new birth, or transfer of cattle into an existing herd. Examples of standard actions that occur within processing include installation of an animal marker (such as a visual tag, RFID tag, retinal scanning, etc.), separation of animals into herds, and initial physical exams.
  d. Treating—This term refers to preventive or remedial actions taken to return an animal to normal health. Accordingly, treatment would include administration of various medications, procedures performed by a veterinarian, etc.
  e. Moving—This term refers to the sorting of cattle within a particular pen or pasture that occurs over time to group and separate animals as necessary based upon growth progress, health, and other factors.
  f. Birthing—This term refers to a birth of calves.
  g. Pregnancy checks—This term is self explanatory and although can be considered a subset of treating, pregnancy checks are a standard procedure that can be distinguished from treating.
  h. Breeding—This term is self explanatory and generally refers to actions taken with respect to preparing animals for, and conducting breeding.
  i. Feeding—This term refers to all activities associated with feeding the animals to include monitoring inventory for feed provided to animals, and the types of feed provided to animals.
  j. Shipping—This term refers to the actions taken to move an animal from a cow/calf operation to a grower/feed lot operation.

With respect to the grower/feed lot module of the present invention as also discussed further below, there are also certain general actions/activities that occur for which data is generated, stored, manipulated and transferred. These activities are summarized as follows:

a. Cattle receiving—This term refers also to animals being brought to a particular feed lot or grower after the animal has been shipped from a cow/calf operation. Detailed data entries occur for this activity to record the type of animal received, its weight, the owner, and other pertinent data.
  b. Inventory receiving—This term refers also to the receipt of various supplies including medications, equipment, tagging devices, and other materials that are used at a grower or feedlot. Receipt and use of these supplies requires an inventory function, to include recordation of how and when particular medications are administered to cattle.
  c. Processing—This term refers generally to the standard or routine actions that take place with respect to introduction of the animal into a particular pen or lot within the grower/feedlot. One standard action that occurs within processing here is an initial physical examination and tagging the animal with another identifier.
  d. Treating—This term again refers to preventive or remedial actions taken to return an animal to normal health.
  e. Calling—This term refers to the act of requesting a certain amount and type of feed to be delivered to a particular bunk or location within the grower/feed lot. This calling function can be generated by an existing bunk reader system that generates a feed order based upon the number and type of animals within a particular pen and lot.
  f. Batching—This term refers to the act of preparing feed and feed additives, medications, and other nutritional supplements to be delivered in response to a call.
  g. Feeding—This term refers to all activities associated with feeding animals to include monitoring inventory for feed provided to the animals, and types and amounts of feed provided to the animals, among other information. This term may overlap with the functions of calling and batching.

h. Shipping—This term refers to the act of moving cattle from the particular grower/feed lot location to a slaughter house.

BRIEF DESCRIPTION OF THE DRAWINGS

FIG. 7 is a table providing examples of preassigned criteria;

FIG. 8 is a user screen for creation of a recommended treatment based upon one or more criteria;

FIG. 9 is a user screen for determining when a ration should be changed based upon one or more criteria;

FIG. 10 is a user interface screen for determining how a ration should be fed to one or more animals over a period of time based upon one or more criteria;

FIG. 11 is a user screen for determining how animals should be sorted based upon one or more criteria;

FIG. 12 is a user screen for establishing custom criteria associated with any desired management function to include feeding, treatment, and sorting;

FIG. 15 illustrates a user screen for data entry of particular premise locations;

FIG. 28 illustrates a user screen for data entry for initial processing of animals as they are received into a feedlot;

FIG. 29 illustrates a user screen including a listing of drugs from the drug list button of FIG. 28 for modifying an existing drug, such as adding or deleting a particular drug from an available listing of drugs;

FIG. 31 is a user screen for individual animal processing;

FIG. 32 is a user screen for further entering data about an animal as it is being processed;

FIG. 33 is a user screen for selecting particular animal processing parameters to be entered and recorded;

FIG. 34 is a user screen for scheduling treatments of animals;

FIG. 35 is a user screen for indicating pending work orders;

FIG. 36 is a user screen showing a sample report corresponding to the pending work order chosen from FIG. 35;

FIG. 37 is a user screen for modifying previously entered data regarding processing for animals;

FIG. 38 is another user screen for modifying previously entered data regarding treatment/processing of a specific animal;

FIG. 39 illustrates a user screen for review of treatment history and for data entry of new treatment;

FIG. 40 is a user screen for modifying treatment data or for entering additional treatment data completed on a prior date;

FIG. 41 illustrates a user screen where a user has selected from a treatment history listing for a particular treatment date;

FIG. 43 is a user screen illustrating data entry to record receipt of animals that are being received from another location;

FIG. 45 is a user screen for recording group animal movements;

FIG. 46 is a user screen for recording group movement from multiple pens into a single pen;

FIG. 47 is a user screen for recording shipment of animals;

FIG. 48 is a user screen illustrating detailed information for recording shipment of a particular animal;

FIG. 49 is a user screen for recording shipment by individual animal as opposed to recording shipment of a group of animals;

FIG. 50 is a user screen for entering data regarding a change in status of a particular animal;

FIG. 51 is a user screen showing an example of an animal that has been designated as a railer;

FIG. 52 is a user screen illustrating an example of an animal that has been designated as a realizer;

FIG. 53 illustrates a user screen allowing data entry for individual selection of animals to be recorded as being moved from one location to another;

FIG. 54 is a user screen providing information regarding the location of animals at a designated time;

FIG. 55 is a user screen for modifying existing data regarding a dead animal;

FIG. 56 is a user screen for modifying existing information of a railer record;

FIG. 57 is a user screen for modifying existing data regarding a realizer record;

FIG. 61 is a user screen showing a listing of diagnosis codes corresponding to a particular ailment or condition;

FIG. 63 is a user screen for viewing inventory to include items such as drugs, and allowing the user to modify such information as necessary;

FIG. 64 is a user screen for recording inventory being received;

FIG. 65 is a user screen for adjusting inventory;

FIG. 66 is a user screen for checking inventory of a particular drug;

FIG. 68 is a user screen illustrating a recommended treatment allowing a user to enter particular treatment protocols or recommendations for a specified diagnosis;

FIG. 69 is another example of a user screen for creating a recommended treatment based upon various criteria, and a mathematical relationship applied to the criteria;

FIG. 70 is a user screen for viewing recommended treatments or to disable the display of recommended treatments during animal processing;

FIG. 71 is a user screen showing another example of data entry for establishing another custom criteria;

FIG. 72 is a user screen for data input of modifications to any of the individual status fields for a particular animal to include tag information and animal condition;

FIG. 74 is a user screen for data entry corresponding to associates within the data processing system;

FIG. 75 is a data entry screen for read codes;

FIG. 76 is a data entry screen for setting up particular facilities within the data processing system;

FIG. 77 is a data entry screen for editing specific data concerning each facility;

FIG. 82 is a user screen for designating location destinations such as pastures;

FIG. 83 is a user screen for setup of particular locations such as pen numbers;

FIG. 85 is a user screen for recording weather data for a particular date and time;

FIG. 86 is a user screen allowing an administrator to identify and set up access for each and every user of the system;

FIG. 89 is another user screen screen for establishing an interface with a financial accounting system;

FIGS. 93-137 illustrate example reports that may be generated from data recorded in the data processing system.

DETAILED DESCRIPTION

I. System Overview

Figure 1:
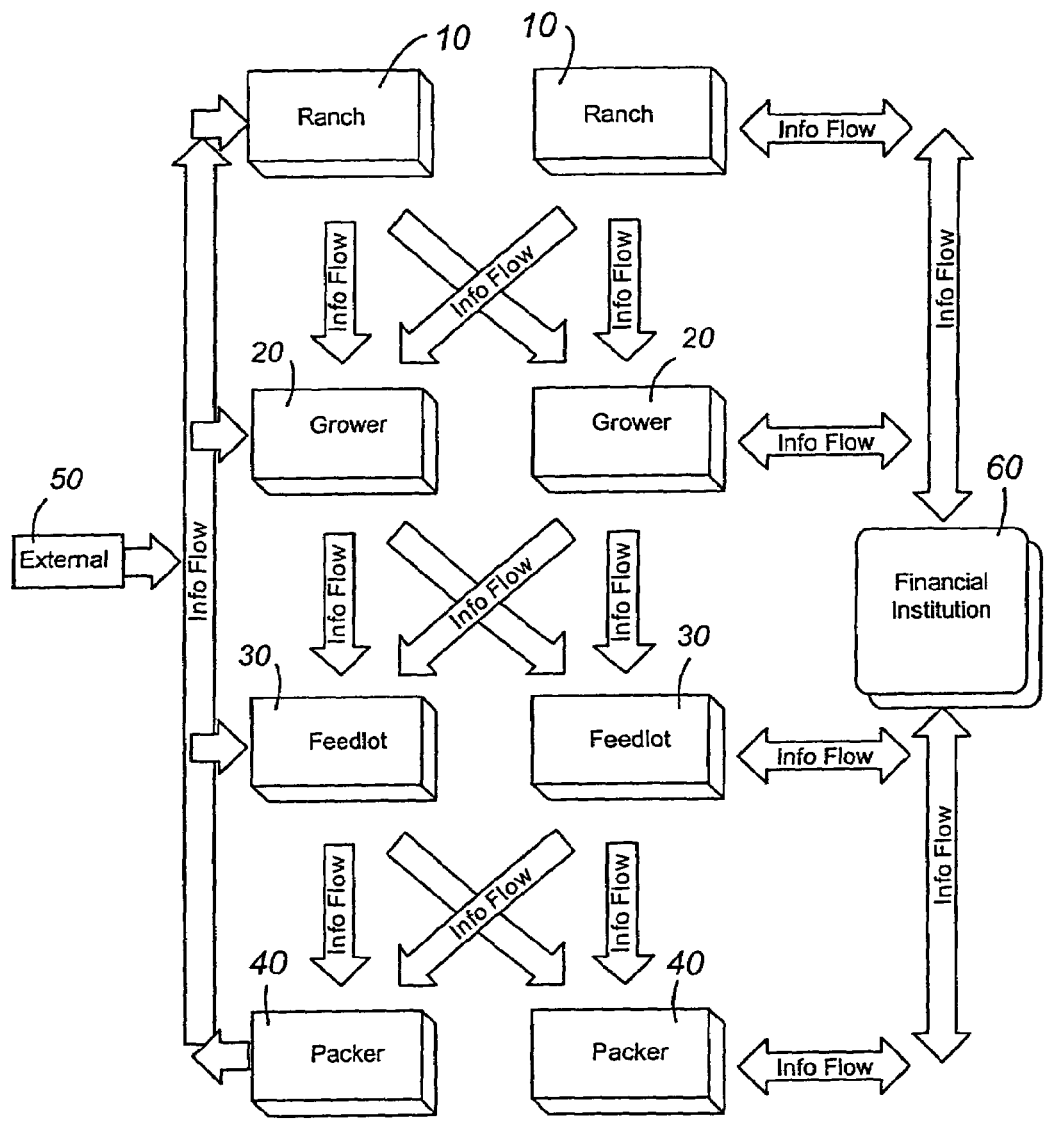
FIG. 1 is an information flow diagram illustrating basic flow of information within the data processing system of the present invention.

FIG. 1 is an information flow diagram showing the basic flow of information within the data processing system, and the organizations that generate, transfer and receive information. Beginning with a ranch or cow/calf operation 10, information is generated and may be transferred to one or more intermediate grower operations 20. The growers generate and transfer information to the feedlots 30. The feedlots 30 generate and transmit information to the packers 40. Information may also be generated and transferred from external sources 50 and integrated within the information that is created, stored, and transferred in each level between the ranch operation and the packers. For example, the external source 50 could generate information regarding new animals brought into a particular herd from a third party source. As also shown in FIG. 1, information transferred between ranchers, growers, feed lots and packers does not necessarily travel between exclusive associations or relationships; rather, ranchers will periodically transact business with various growers, growers will transact business with various feed lots, and feed lots will transact business with various packers. As also shown in FIG. 1, a corporate entity 60 is shown which may have an interest in receiving and transmitting data to the various organizations. A corporate entity could include those which track performances of feed lots or ranches, or the corporate entity could be a financial institution that calculates return on investment for a particular feed lot, grower or packer.

Figure 2:
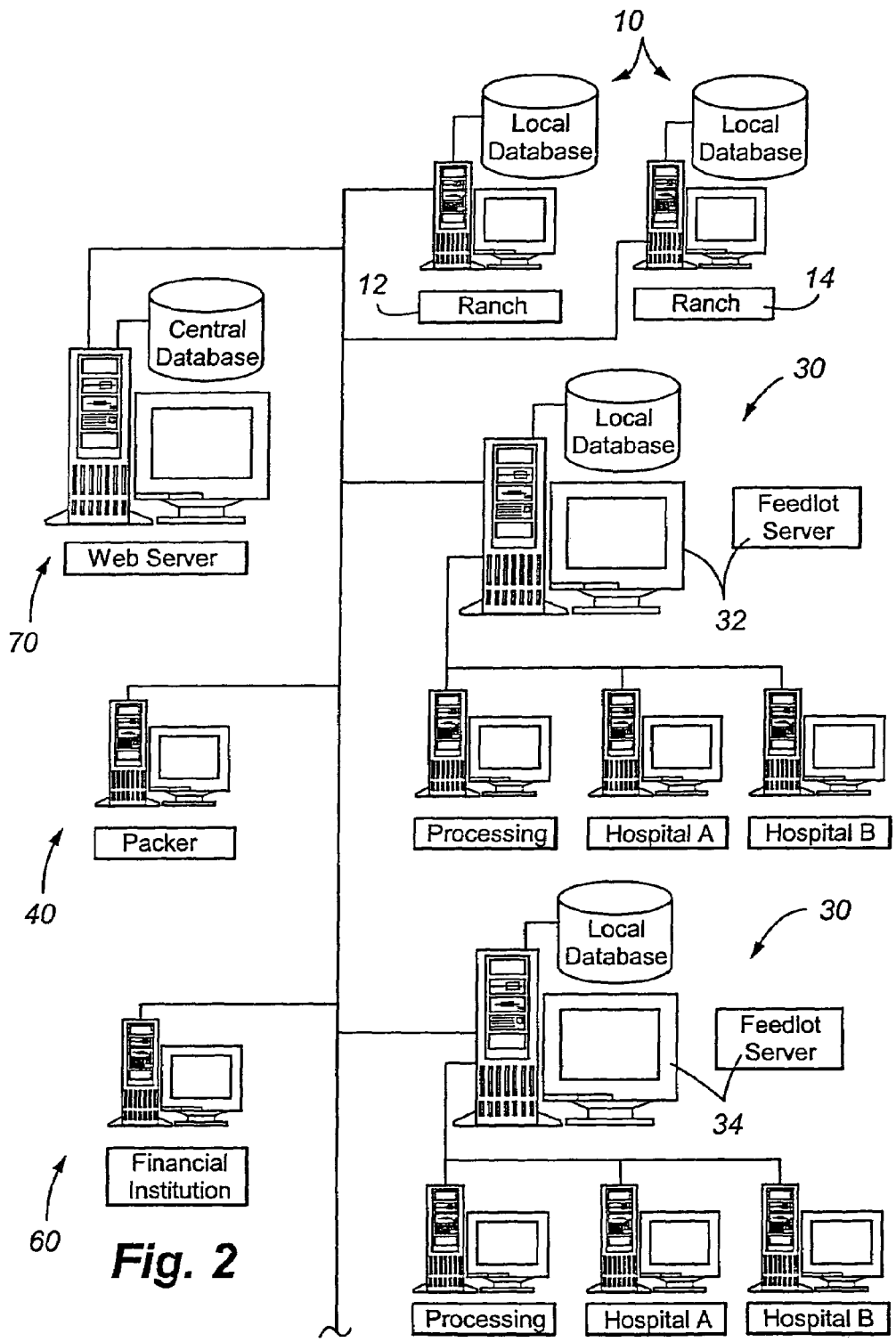
FIG. 2 is a simplified schematic diagram illustrating an example of implementation of the data processing system of the present invention within various organizations.

FIG. 2 is a simplified schematic diagram illustrating one example of how the data processing system of the present invention may be incorporated within various organizations of the system. Two ranch operations 10 are illustrated, namely, ranch 12 and ranch 14. Each of the ranches would have a sufficiently powerful computer and local databases for running of the cow/calf module. As discussed further below, the cow/calf module is specifically designed to collect all data associated with breeding, birth and processing operations at a ranch location. The cow/calf module can be considered a stand alone herd management tool, and the cow/calf module can be interfaced with the grower/feed lot module. Two feed lot operations 30 are illustrated, namely, feed lot 32 and feed lot 34. Each of the feed lots may include their own server and local database(s) for storage of data generated in the grower/feed lot module. Within the feed lots, various other computers may be found which input data directly into the database(s) at the local servers. For example, each of the feed lots 32 and 34 are shown as including discrete work stations within the feed lot which directly input information to the local database. These workstations include a processing station, hospital A and hospital B. These stations would not have their own databases, but rather would directly update the local database found at the local server. FIG. 2 also illustrates other organizations within the system to include a packer 40 and a financial institution 60. These organizations are also shown without databases since they would simply request data from the local servers at the feed lots, or transfer data to the local servers.

FIG. 2 also illustrates the use of a web server 70 which includes its own central database. It may also be desirable to have a web server with a central database which would ultimately serve as the single repository for storage of data within the system. Thus, if a web server was used, the local servers at the feedlots could temporarily store data until it was transferred to the central database. Accordingly, each of the organizations within the system would then access data from the central database as opposed to accessing data at each of the separate local servers. In some circumstances, incorporating a central database at a web server may better facilitate the ability to more efficiently store and update system information, as well as enhance the ability to transfer data to multiple organizations.

Referring again to FIG. 2, in lieu of the web server 70 being a central repository for storage of data, the web server 70 could simply act as a secure Internet FTP server which would provide a secure means of data transfer between organizations in the system, and transferred data is only resident on the server 70 while being transferred between the systems and then removed when the data transfer is complete. Thus, the web server 70 could simply be an Internet FTP site.

Figure 3:
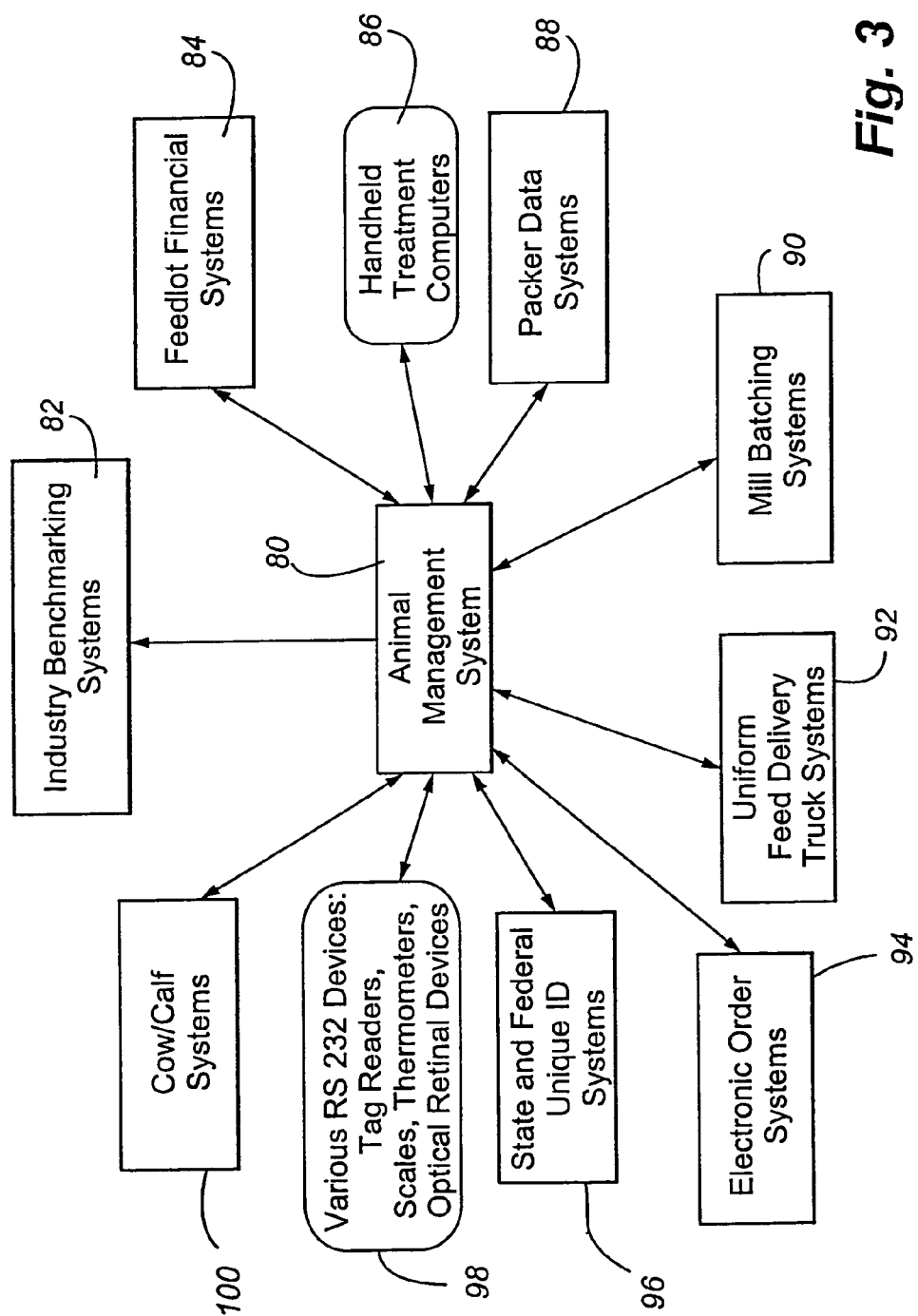
FIG. 3 is a schematic diagram illustrating external information systems that may interface with the data processing system of the present invention.

Another important aspect of the present invention is its ability to interface with various other information systems and data acquisition equipment for data entry into the system. Referring now to FIG. 3, a schematic diagram is provided to illustrate some example external information systems that may interface with the data processing system of the present invention. System 80 of the present invention is described as an animal management system which interfaces with a great number of external information systems to include industry bench marking systems 82, feed lot financial systems 84, hand held treatment devices 86, packer data systems 88, mill batching systems 90, uniform feed delivery truck systems 92, electronic ordering systems 94, state and federal unique ID systems 96, various RS 232 devices 98, and cow/calf systems 100. The methods of data transfer between the animal management system 80 and the outside systems can be recording media (such as CD's, diskettes, etc.), Internet FTP, Intranet, and various network configurations such as wide area and local networks as further discussed below.

Cow/calf systems 100 refers to third party cow/calf systems which may be similar to the cow/calf module of the present invention, specifically designed for animal management at a ranch location. Typically, cow/calf systems 100 are stand alone computer systems that are installed and run at each separate ranch location. These systems record all sire and dam data along with recording all calves born at the ranch location. These systems also record all treatment of calves while at the ranch location. These systems also may be designed to analyze herd data and assist ranch management in detailed herd management functions. The herd management function may be designed to receive data associated with feeding, treatment and packer production from other systems and supply reporting that will assist ranch management in fine-tuning its breeding programs for better return on investment. Typical interface methods for a cow/calf system may include recording media or transfer by Internet FTP. With all interfaces incorporated within the present invention, the preferred method of transfer is a secure Internet FTP server. For most cow/calf systems, the secondary method of transfer would likely be recording media such as optical disks, magnetic disks, or other similar mass storage devices. In terms of a data format during transfer, one convenient protocol would be for storage of the data in a flat ASCII file format. The data can then be reconfigured within the feedlot servers or web server as desired based upon the type of resident databases which may be found in each location.

A uniform feed delivery truck system 92 includes those truck based computer systems that control the uniform delivery of feed to a feed bunk. These systems control the amount and rate the feed is dispensed from the feed truck based upon a previous call from each feed bunk. The animal management system of the present invention can send data to the delivery truck system to include information such as ration codes, ration call amounts, bunk locations, and other bunk specifications which dictate the delivery of feed to the feed bunks. The feed truck systems in turn record the actual amounts of ration delivered to the feed bunk to include truck identification and driver identification. The preferred method of data transfer between the system of the present invention and the feed delivery truck systems would be through a radio frequency connection that utilized a network or radio modem. Secondary methods of data transfer could be use of any type of recording media.

A hand held treatment device 86 is a remote device that is designed to record certain transactions associated with the animal health module of the present invention without a direct connection to the database of the system while recording the transaction. These types of hand held computers record individual animal treatments, processing and individual animal receipt transactions. Data validation tables along with active animal identification data are downloaded to these hand held computers prior to use, and then recorded transactions will be uploaded to the database of the present invention and posted to the database. The preferred method of data transfer between the invention and the hand held computer would be through a network protocol utilizing a radio frequency connection, a Blue Tooth protocol or a cable connection. The cable connection could be a number of known connections such as RS232/USB connections. A secondary method of transfer could include use of recording media.

Mill batching systems 90 are computer systems that control ration mixing equipment located at a feed mill. These systems select ration formulas and batch sizes to be mixed by the mill equipment. The present system can transfer data to the mill batching systems in summary or detailed levels. A summary level would simply transfer a particular ration code and total call amount to the batching system, and the batching system would comply with batching amounts in the size and content as requested. The actual batch content for each ration would be transferred back to the system from the batch control system. At a more detailed level, transfer could be obtained for truck batch identification numbers, batch sizes, pens to deliver and batch ingredient content to the mill batching systems, and the actual batch ingredient amounts along with batch identification would be returned to the system. The preferred method of data transfer between the present system and the batching system would be through network protocol utilizing a radio frequency connection or a cable connection. A secondary method of transfer could be use of any recording media.

Feedlot financial systems 84 refer to the various industry specific financial control computer systems. The data processing of the present invention sends data associated with cattle inventory, animal healthcare data and animal feeding data to these financial control systems. The data processing system then can receive certain selected data elements associated with groups of cattle and individual animals from these financial control systems. The preferred method of data transfer would be through network protocol utilizing a radio frequency connection or a cable connection. Secondary methods of data transfer could be use of any recording media.

Packer data systems 88 refer to packer production data files from packers in the form of files that contain production data identified by the unique animal identification numbers. The present system posts this production data to individual animal records in the databases of the present invention. This production data can in turn be used to analyze individual animals or groups of animals for return on investment, producer evaluation, and buyer evaluation or can be interfaced back to a cow/calf system to assist the ranch manager with herd evaluation or return on investment. The preferred method of data transfer or packer data systems would be through a secure Internet FTP server. A secondary method of transfer could be use of any type of recording media.

State and federal unique ID systems 96 refer to data transfer between the present system and those federal and state entities which may require unique animal identification data and unique premise data. The present invention would have the capability to transfer unique animal ID's along with premise ID's, as well as certain activities associate with each animal to the various state and federal agencies requesting information on individual animals and individual locations. The preferred method of data transfer between the present invention and the various state and federal agencies would be through a secure Internet FTP server. The secondary method of transfer could be any recording media.

For industry benchmarking systems 82, the present invention has the capability to send individual animal data that contains treatment, feeding and production data to the various industry benchmarking systems. Industry benchmarking systems 92 refer to those which analyze data from feed lots to determine basic productivity/profitability of organizations within the industry. The preferred method of data transfer between the benchmarking systems and the present invention would be through a secure Internet FTP server. A secondary method of transfer could be any type of recording media.

The electronic order systems 94 refer to those outside ordering systems which allow automatic generation of supply orders to fulfill the supply needs of a particular location such as a ranch or feed lot. The present invention would automatically transfer data to the electronic ordering systems based upon current inventory, projected usage, preset order levels, reorder points, and any other criteria set for required stockage of any supplies. The preferred method of data transfer would be through a secure Internet FTP server. The secondary method of transfer could be faxing of generated order documents to a particular order processing group that handles customer orders.

The various RS232 devices 98 refer to field devices such as scales, tag readers, temperature measuring devices, and retinal scanning devices. These devices can be connected to the present data processing system via cables, radio frequency connections, or other connections. The data being recorded by these devices can be passed from a particular terminal location or work station directly into the database(s) of the present invention.

Figure 4:
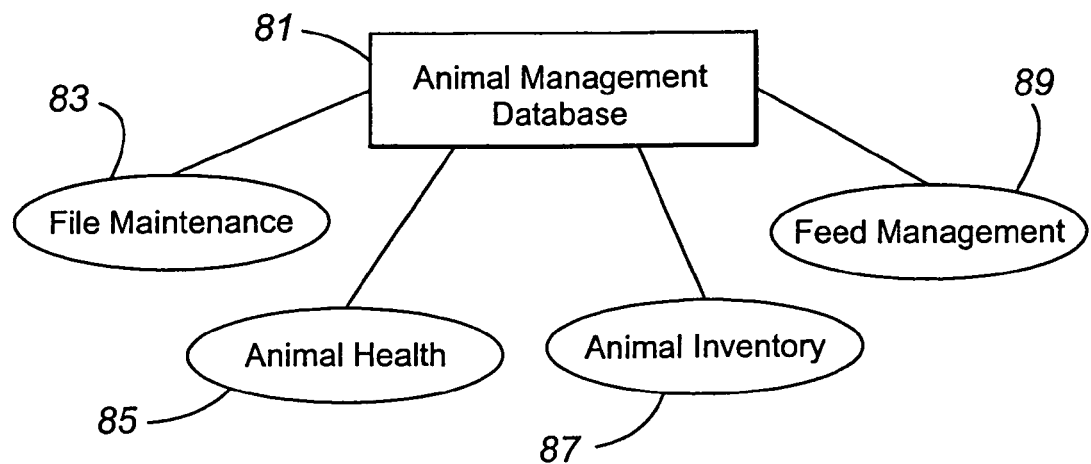
FIG. 4 is a schematic diagram illustrating a central database, and various functional modules that communicate with the central database for data storage, retrieval, transfer, and other functions of the modules.

FIG. 4 illustrates another schematic diagram illustrating one example of how a central database is incorporated within the present invention. As mentioned above, with respect to the web server 70, this central database may reside at the web server, or any of the other local servers of the system that transfer data to and from the various other servers. More specifically, this central database can be incorporated within any one or all of the modules allowing a user to provide data inputs that are then accessible for all functions of the system. In the example, the single or central database is represented as animal management database 81 for the grower feedlot module. Four primary functions of the grower feedlot module are illustrated as being associated with the animal management database, namely, file maintenance 83, animal health 85, animal inventory 87, and feed management 89. All data relating to these four primary functions are stored within the animal management database 81. By use of the single central database, multiple data entries for the same event or data entry is eliminated, and a single data entry can potentially affect any number of module functions assuming the module functions require the data in one or more data fields of the function. For example, when an individual animal is treated in the animal health module and is moved to a hospital pen, a data entry is made which records the animal as being moved to the hospital pen. This data entry can be created in any number of different manners to include an RFID transponder that interrogates the animal's tag and then the transponder communicates with the system for data input of the tag ID. A feed management module feed calculation for the animal's home pen is then affected by the removal of the animal to the hospital pen. That is, the feed calculation is reduced an appropriate amount to account for the absence of the animal at the home pen. The feed calculation function incorporates an algorithm or mathematical expression that requires a daily head count, and the daily head count is determined by analysis of data entries corresponding to the pen locations of the animals. The feed management module feed calculation for the hospital pen is also affected to account for transfer of the animal to the hospital pen, wherein the feed call is increased an appropriate amount to account for the animal arriving at the hospital pen. Accordingly, all cattle activity movements to include full pen or partial pen movements by a single data entry recording the move results in the automatic adjustment of the feed call functions for both the gaining and losing pens.

In order to better understand the present data processing system, a number of user interface displays or screens are provided to show the functionality of the system as it applies to the various tasks which create data entries, transfer data and manipulate data, and which therefore result in the ability to track, monitor, and report on animal management. These displays would typically be provided on a user screen of a computer monitor. The terms "user screen" or "user interface screen" shall be understood to encompass any visual display of data and system information provided to the user.

A conventional user ID and password convention can be incorporated thereby providing each user in the system with specified access to various functions of the data processing system. Therefore, the present invention specifically contemplates preconfiguration of the overall data processing system wherein users at a particular premise location may only have limited access to data generated from other locations. System access is discussed in further detail with reference to FIGS. 76 and 77.

Figure 5:
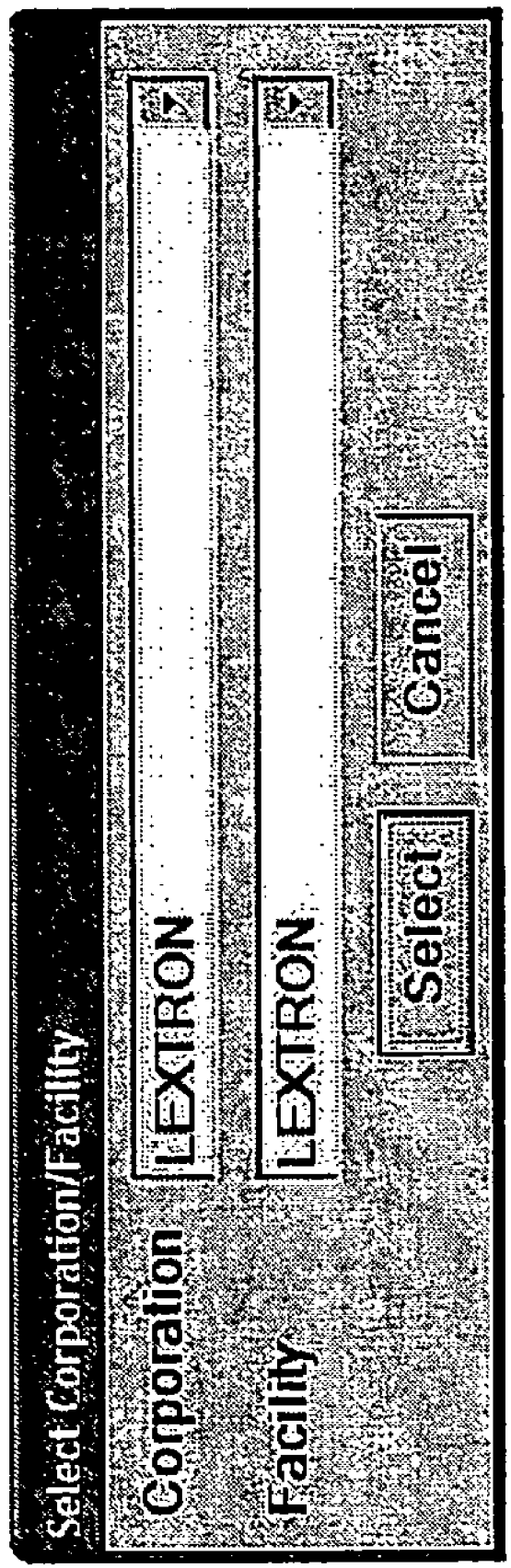
FIG. 5 illustrates a user login screen.

FIG. 5 illustrates a simplified login screen that allows a user to select a particular entity/organization that is going to be addressed and a particular facility within the organization. By selection of a particular organization and facility, the user identifies the particular database to access.

Figure 6:
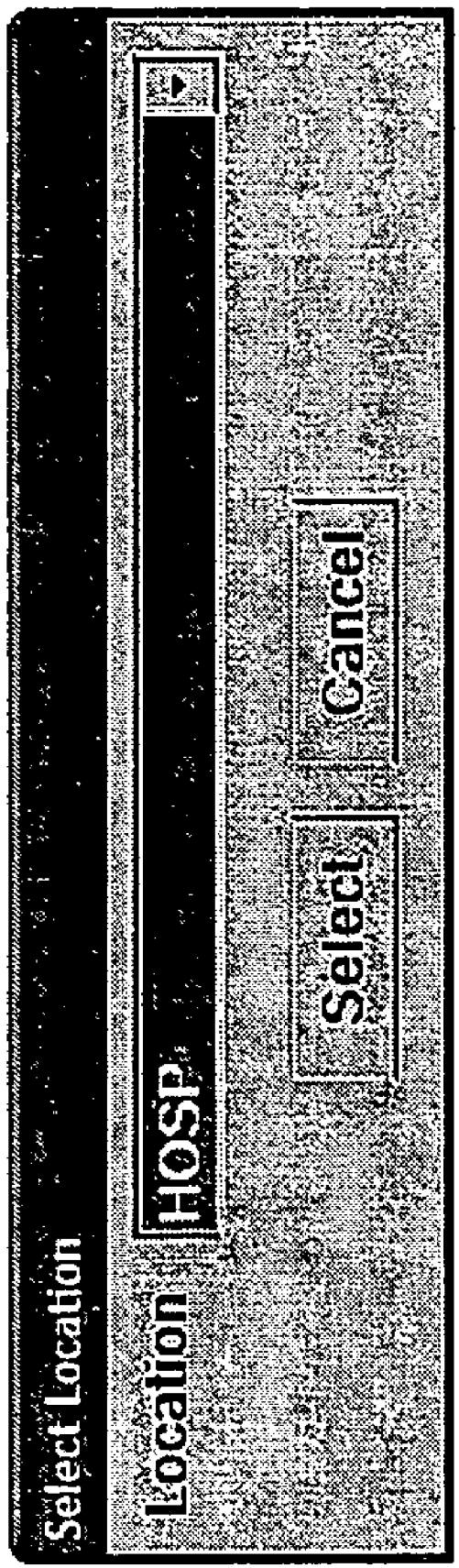
FIG. 6 illustrates a user screen for a particular location within a facility for system access.

FIG. 6 is another screen that allows a user to select the particular location within a facility for system access. There may be multiple locations assigned to a particular facility, each having limited data entry capabilities or system access. For example, a particular location within a feedlot could be a processing station having a weigh scale and a tag reader. This station would therefore have the capability to enter, weigh and tag data. FIG. 6 specifically shows a hospital location.

As mentioned above, it shall be understood that there are many ways in which data can be entered and transferred. One common method is simply an Internet connection from a particular work station/location that communicates with the web server or local servers. However, some locations may have the need to incorporate intermediate data gathering through devices which do not directly interface with a server. For example, with respect to retinal scanning of animals once they enter an inventory, the retinal scanning device may incorporate a hand held unit which creates a digital image of an animal's retina, and then the image is temporarily stored on the hand held device until the image can be downloaded to a nearby work station.

A user can choose to enter data according to preconfigured pull-down menus. Alternatively, the user can choose to manually enter data by keyboard entry. Data can also be entered through integration of remote processing devices, such as the RS 232 devices mentioned above. As a further example, RFID tags are interrogated by a scanner, and the scanner can be interfaced with the present system to allow direct entry of data by the scanner.

One particularly important aspect of the present invention is the ability to manage cattle by production of recommended management actions prompted by previously established logical relationships between data gathered and desired end results. Once a particular relationship is satisfied between the gathered data and the desired end result, the recommended management action can be adopted by the user simply complying with the recommendation action. The recommended action is some form of an instruction such as a message produced for the user to view on a user interface screen, or a message appearing on a printed management report. Thus, the present invention has an active predictive feature that allows cattle managers to proactively manage cattle as opposed to managing only in a reactive manner. For example, within the grower feedlot module, four basic cattle management functions are provided with detailed capabilities, namely, (1) which treatments should be administered to an animal, (2) when the ration assigned to a pen of cattle should be changed, (3) how the assigned ration for a pen of cattle should be distributed during the feeding schedule, that is, when and how the ration should be distributed to the pen of cattle based upon a prescribed feeding schedule and (4) sorting cattle based upon like or similar characteristics among the cattle. These four functions can be conceptually viewed as subroutines within the module. One or more criteria are established which correspond to categories of animal characteristics or other data gathered about an animal or groups of animals for management purposes. The criteria can be stored as a selected list of pre-assigned criteria. The criteria are used within user defined logic such as algorithms or mathematical expressions. The numerical values of the algorithms/expressions correspond to one or more recommended actions, such as a proposed treatment or a proposed feed ration. Data entered and stored concerning a particular animal is then matched with the pre-assigned criteria, and then a recommended action is provided to the user. Thus, the user-defined logic allows the user to customize the functionality of the system without the need to modify actual computer source code in a software program application. Additionally, the user may modify the list of pre-assigned criteria in order to provide additional options for building needed logic relationships to thereby establish recommended management actions.

FIG. 7 provides an example table of pre-assigned criteria that corresponds to basic characteristics of an animal and other information recorded that may be valuable for purposes of managing cattle. These criteria are used as the variables in building the algorithms/expressions. The criteria may include discrete data elements concerning an animal such as animal weight, and may include algorithms/mathematical relationships applied to data to create custom criteria.

Figure 8:
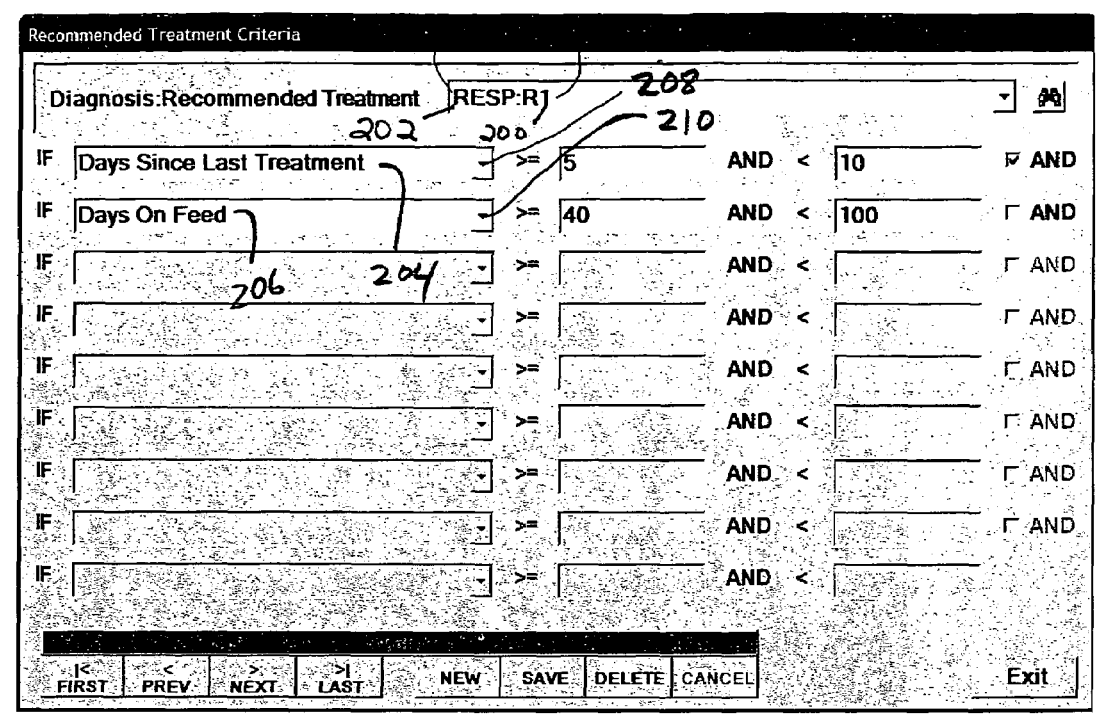

The ability of a user to set up, modify, and implement the four core functions set forth above is now further explained with respect to FIGS. 8-12. Referring to FIG. 8, a user interface screen is illustrated wherein the user can create a recommended treatment based upon one or more criteria. In the example of FIG. 8, the recommended treatment is designated as R1200. The recommended treatment corresponds to a diagnosis 202 by the attending veterinarian, for example, a respiratory ailment denoted as "Resp". The recommended treatment "R1" 200 is based upon two criteria, namely, the number of days since the last treatment, shown at entry 204, and the number of days on a particular feed ration, shown at entry 206. Pull down menus may be activated by clicking on buttons 208 and 210. The menus then display the available criteria for building the treatment. In the example of FIG. 8, for entry 204, if the number of days since the last treatment is greater than or equal to five and are less than 10, then this particular criteria is met. Additionally, if the number of days on feed is greater than or equal to 40 and less than 100, then this criteria also is met and therefore the recommended treatment is "R1". The system will preload the treatment, and the user can then view details of the treatment. The recommended treatment may include an explanation of how the animal should be treated, along with recommended assigned drugs and dosages. The user can view details of the treatment as necessary on a treatment screen or printed report. The entries 204 and 206 are stored in the central database and are evaluated every time that an animal is treated for a diagnosis of "Resp." Accordingly, since data regarding treatment detail is already stored on the system, the user does not have to reenter treatment details each time the animal is diagnosed. Also, creation of the recommended treatment also assists yard management with standardizing treatments administered to like animals.

Figure 9:
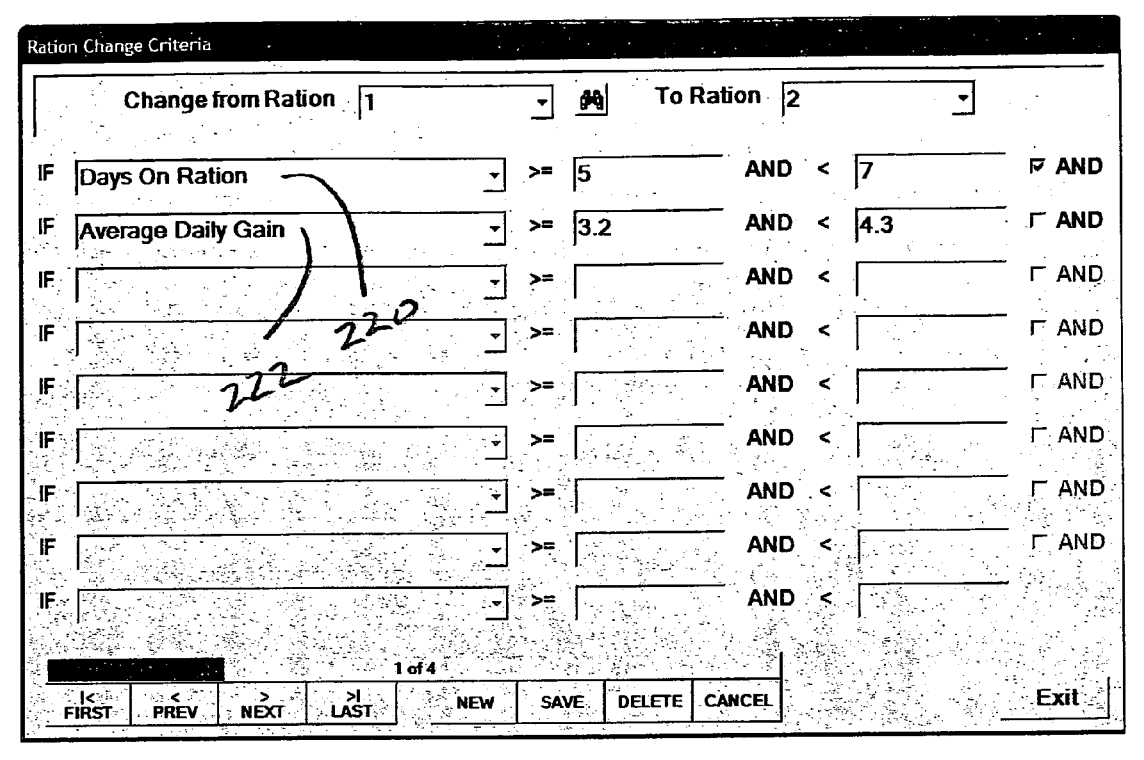

Referring to FIG. 9, a ration change criteria user interface screen is provided which allows a user to establish recommendations for when a ration should be changed. In the example of FIG. 9, there are two data entries or criteria used to build a rule resulting in a recommended ration change from ration 1 to ration 2. More specifically, data entry 220 corresponds to the number of days on a particular ration, and data entry 222 corresponds to the average daily gain, that is, the average daily gain in weight of the animal. If the two criteria are met, then a recommendation is made to change the ration of the particular animal. Each time that a pen or lot data is displayed on feed call screens or is printed in a report, the recommended changes appear in an alert message that recommends the change. This ration change criteria screen therefore assists yard management in standardizing ration changes based upon similarly performing animals, thereby maximizing potential amount of weight gain for each animal.

Figure 10:
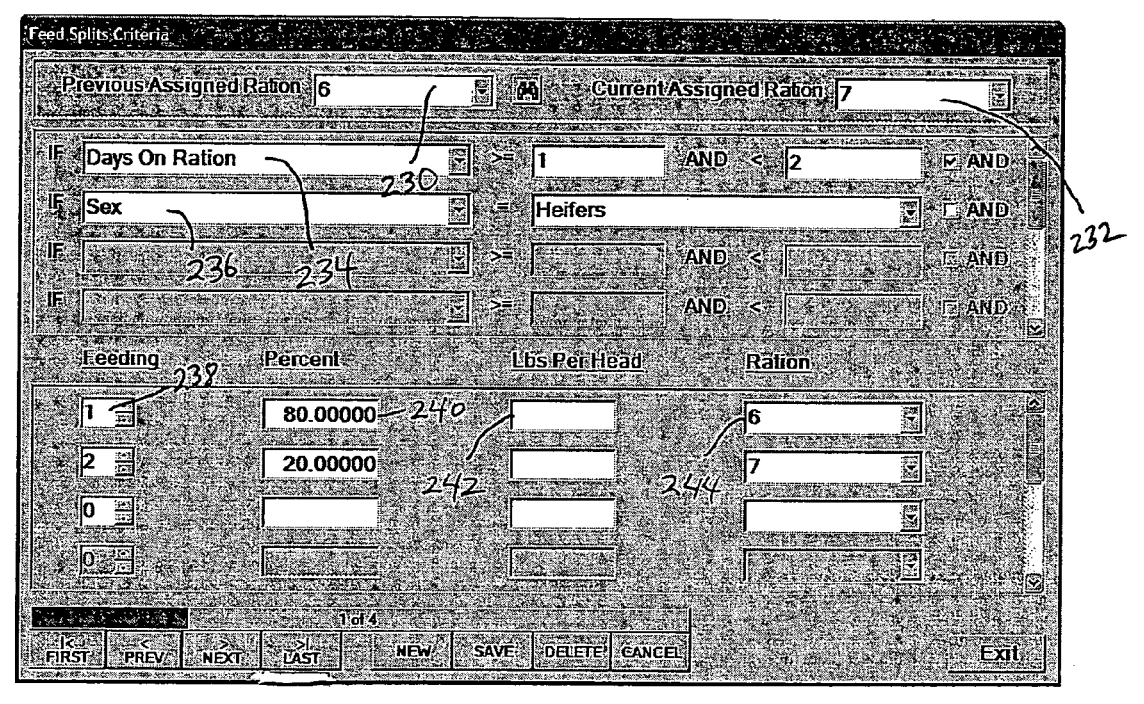

Now referring to FIG. 10, a ration change feeding method screen is provided allowing a user to create rules or recommendations regarding how an assigned ration is fed to a group of animals over a period of time. On the upper portion of the screen the previous ration code is provided at block 230 (Change from ration 6), and the new ration code is displayed at block 232 (To Ration 7). If the ration type/code has not changed, then the change from and to rations would show the same ration code. Blocks 234 and 236 are shown as criteria chosen for determining the feed method of a particular animal or group of animals. In the example, the first criteria at block 234 is days on ration, and the second criteria is the sex of the animal. If these criteria are met, then on the first day of the ration change, the recommended feeding method is to feed 80% of the total daily feed in the first feeding of the day, and the remaining portion of the daily feed (20%) in the second feeding of the day. Accordingly, block 238 denotes the particular feeding of the day, and block 240 denotes how much of the total daily feed should be fed at the designated feeding. Block 242 denotes how many pounds of feed should be fed per head, and block 244 indicates which particular type of ration should be fed at which feeding. It is noted that in the first feeding of the day, the old ration (ration code 6) is fed and then in the second feed of the day, the new ration (ration code 7) is fed. On the next day, the proportionate amount of the ration codes could then change to feed more of the new ration code and less of the old ration code. Thus, the feed ration can be tailored to allow a transition period for changing the type of ration. Accordingly, blocks 238, 240, 242, and 244 represent the variables that can be modified in order to establish a recommended feed method corresponding to one or more criteria.

Figure 11:
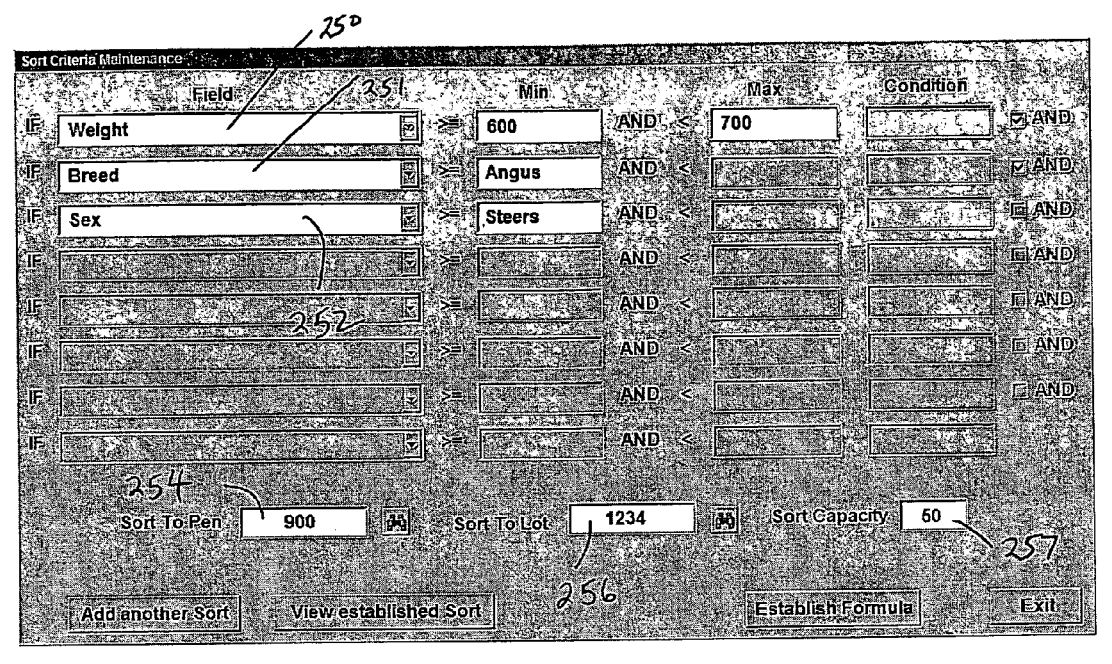

Referring to FIG. 11, another user interface screen is provided for establishing rules or recommendations for how animals should be sorted. Periodically, a group of cattle are reviewed for how the cattle should be regrouped based upon their most recent performance. In a cattle-sorting operation, it is advantageous to have accurate history on the performance of the animal. With the sort criteria function of the present invention, preset rules or recommendations are provided to a user for sorting like cattle. In the example of FIG. 11, three data entries or criteria 250, 251, and 252 are shown. Criteria 250 is the weight of the animal and if the weight is between 600 and 700 pounds, the first criteria is met. The second criteria 251 is the breed (Angus), and the third criteria 252 is the sex (steers). As each animal is processed through a chute for tag reading purposes or otherwise the animal's tag is read, the system compares the animal's data to the criteria, and if the animal's data matches the algorithms/relationships for the criteria, the system assigns the animal to a new lot and pen. The new pen location is shown at box 254 and the new lot location is shown at box 256. Accordingly, sorting in this manner ensures that animals of like performance will be grouped together thereby easing management of the cattle during their critical growth period. Although a new grouping may be recommended for one or more cattle during the sorting process, original data for each animal is maintained to provide necessary historical data on the particular animal. For example, the original load identification assigned to an animal when they are received into a particular yard is still stored in the system to ensure that identity of each animal can be traced back to the original receiving group of cattle. Block 257 provides a count of how many cattle are sorted to a particular pen and lot versus the actual capacity of the pen/lot location. If the recommended sort count exceeds the capacity, a warning message is provided to the user indicating that the sort criteria should be re-evaluated.

Figure 12:
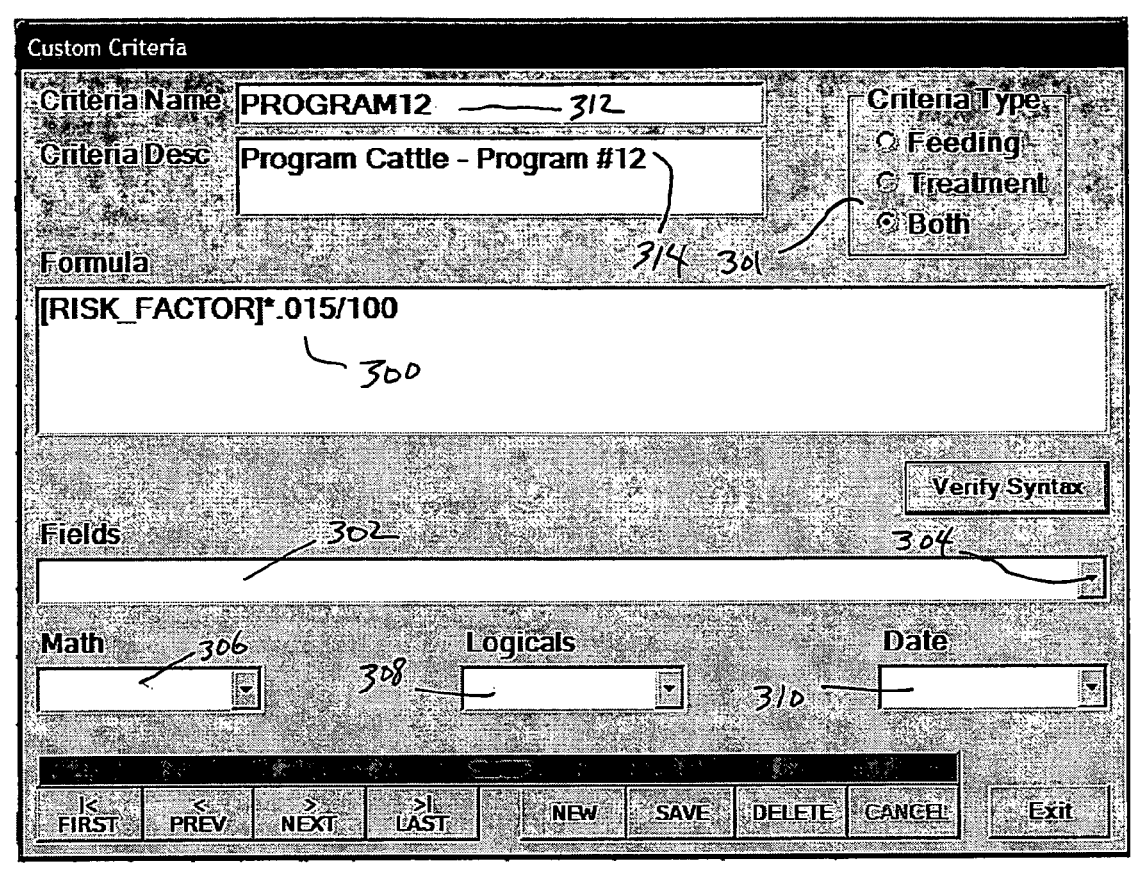

Referring to FIG. 12, a custom criteria user interface screen is provided that allows the user to build a formula/algorithm for any particular criteria associated with feeding, treatment and sorting. Custom criteria created may then be added to the available listing of criteria and used in building the rules to generate recommended actions for feeding, treating, and sorting. The completed formula appears in block 300. The criteria type is designated in block 301. The user can develop the formula based on the available field listing in block 302. The user activates the pull down menu by clicking on button 304 and chooses the fields for insertion in the formula. The fields may include some of the same criteria listed in FIG. 7 as well as any available recorded data elements stored in the central database. Various math and logical operations are chosen to build the particular formula, as shown at blocks 306 and 308. The criteria name is entered in block 312, and a short criteria description can be provided in block 314.

II. Cow/Calf Module

The first module of the present invention to be discussed is the cow/calf module. This module is intended to be a stand-alone data processing system designed to operate on a computer system located at a cow/calf operation. The module collects all animal data associated with breeding, birth, processing and treatment. In addition to being a stand-alone data processing system, particularly advantageous for use as a herd management tool, it could also be interfaced with the other modules of the present invention so that data may be passed between the cow/calf module and the other modules of the present invention. For example, the cow/calf module can be interfaced with any one of the local servers residing at feedlot locations, or the web server, if a web server exists.

Figure 13:
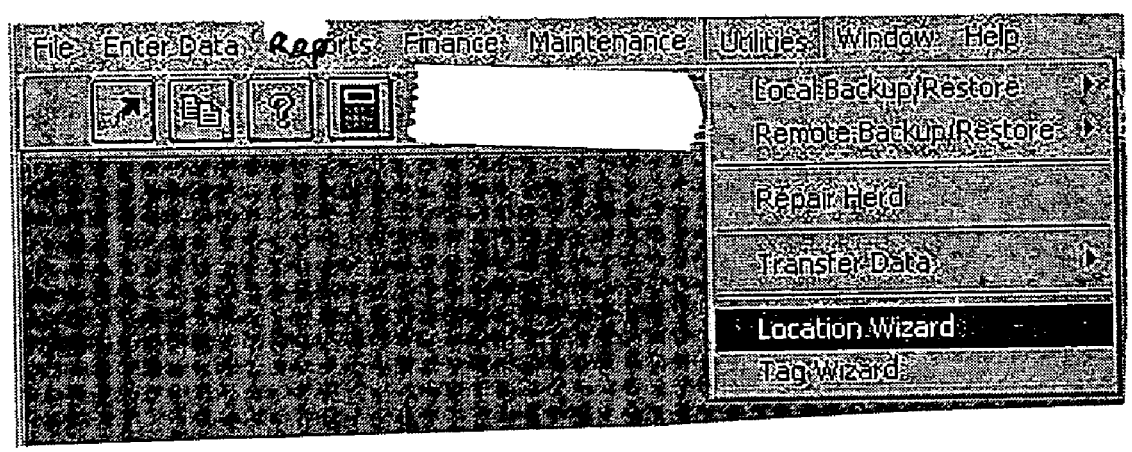
FIG. 13 illustrates a pull-down menu for entering new animals into the cow/calf module or for transferring data in or out of the module.

FIG. 13 illustrates a pull-down menu for entering new animals into the cow/calf module or for transferring data in or out of the module. For example, it may be necessary to retrieve data from a feed lot module and send it to a cow/calf module, or vise versa.

Figure 14:
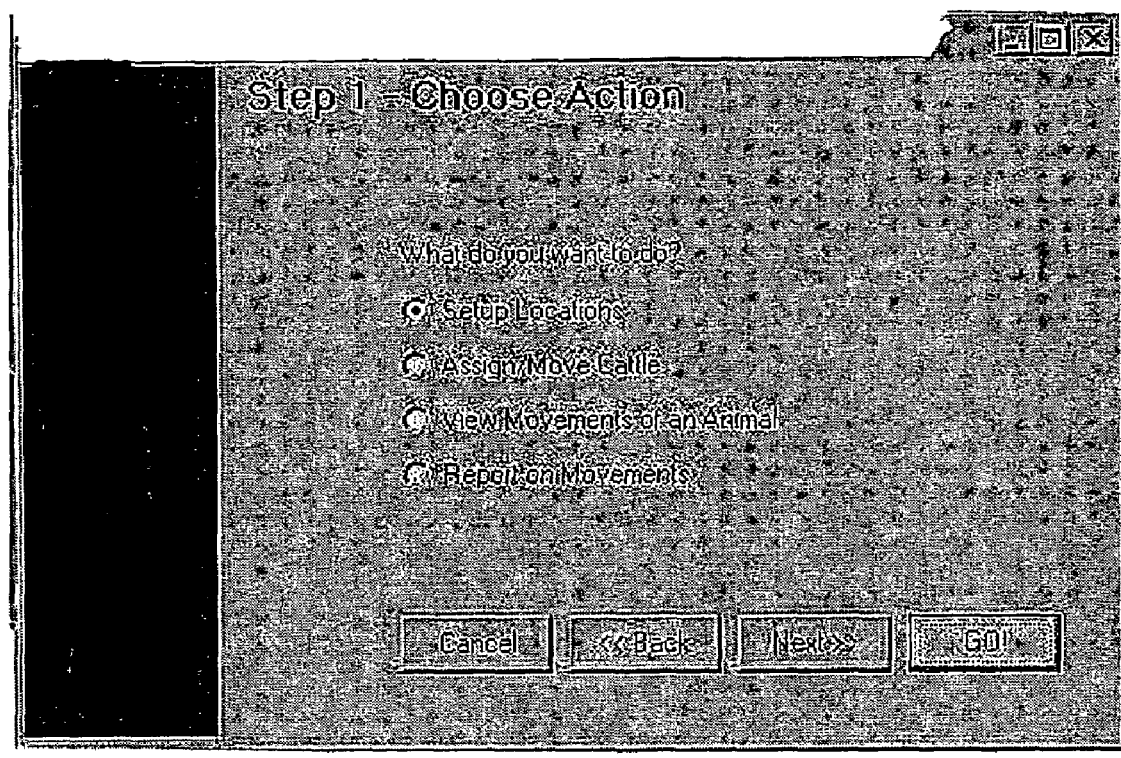
FIG. 14 illustrates a user screen for selection of the location wizard option from the pull-down menu of FIG. 13.

FIG. 14 illustrates a screen for selection of the location wizard option from the pull-down menu of FIG. 13, wherein the user is allowed to set up particular locations that can be assigned a unique premise ID. Assuming a national identification program is required by federal or state authorities, unique premise numbers may be required. In particular, a premise ID could correspond to a particular plot of land such as a pasture in a cow/calf operation, and a particular feed lot pen in a feed lot operation. One technique which may simplify the ultimate assignment of premise location numbers to various cattle operations would be to incorporate global positioning satellite (GPS) technology wherein a particular premise ID corresponds to a geographic coordinate recorded within a GPS system. Those skilled in the art can appreciate other ways in which a particular cattle operation location could be assigned unique premise IDs.

Figure 15:
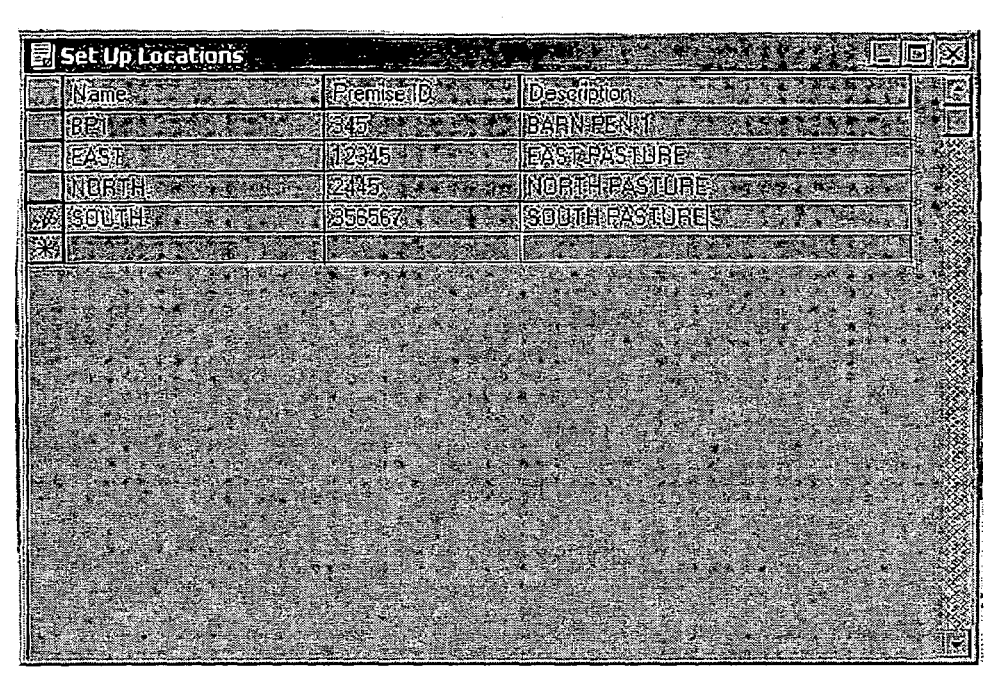

FIG. 15 illustrates a screen for data entry of particular premise locations, corresponding premise IDs, and a short description of the particular premise location.

FIGS. 16-27 are example user interface screens found in the cow/calf module. Each are explained in more detail below.

Figure 16:
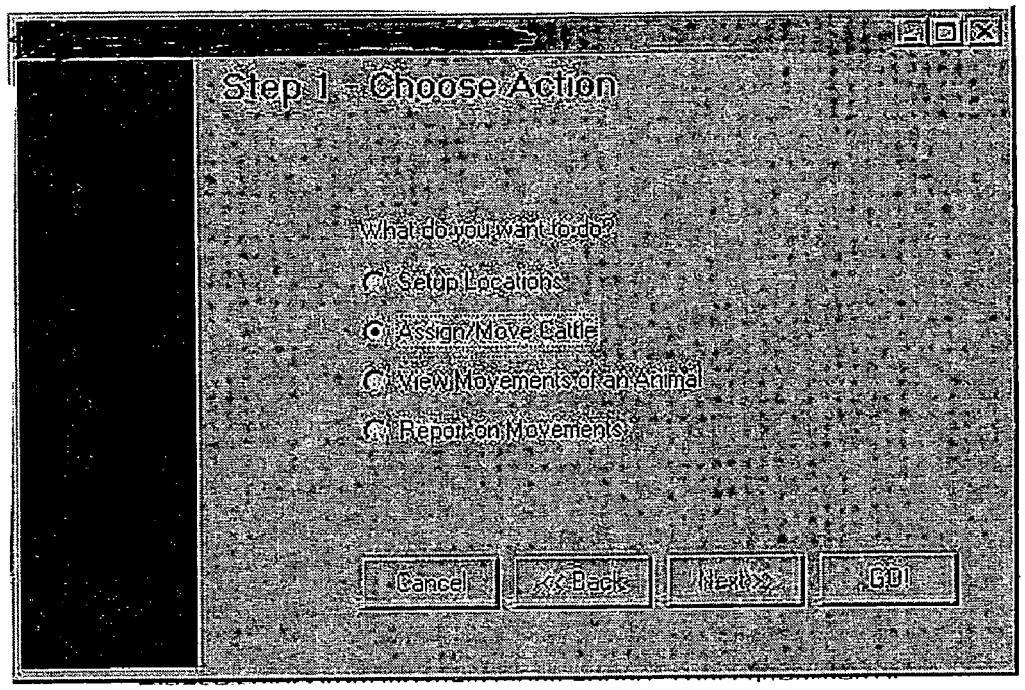
FIG. 16 illustrates a user screen for recording movement of cattle.

FIG. 16 illustrates a user selection screen that allows a user to record the movement of cattle between locations at a cow/calf operation.

Figure 17:
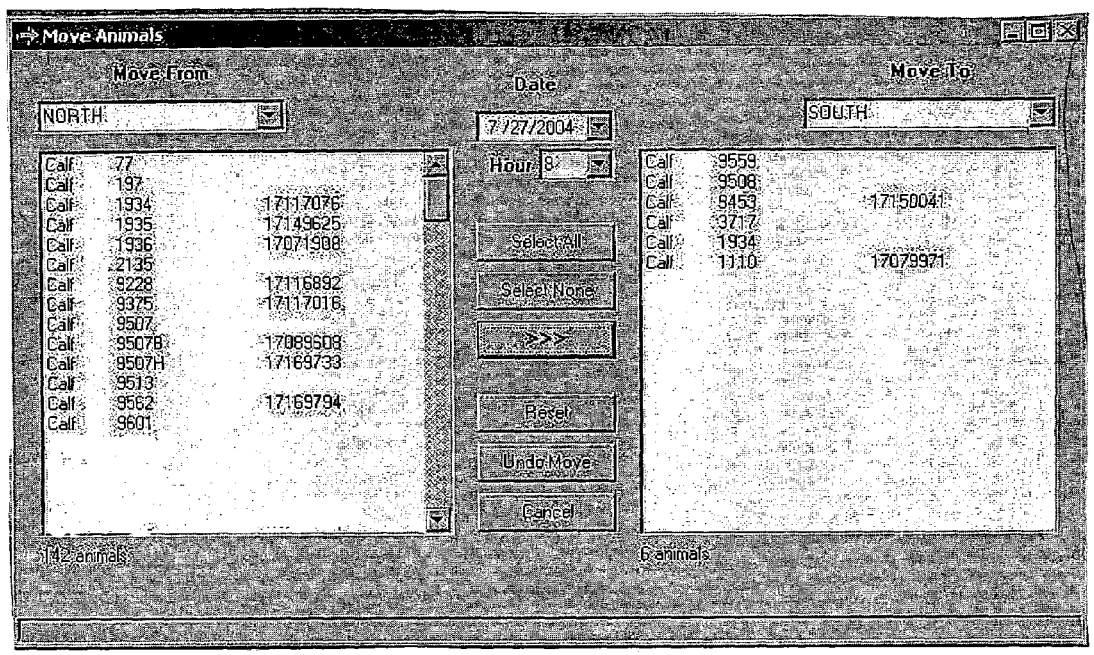
FIG. 17 illustrates a user screen for selecting individual cattle for movement from one location to another location.

FIG. 17 illustrates a user screen that allows a user to select individual cattle for recording movement from one location to another location. As shown in the example, the name of the premise location from which cattle are to be moved is the "north" location and the cattle are to be recorded as being moved to the "south" location. This screen also shows that there are 142 animals currently in the north location and six animals are in the south location. Each of the cattle are identified as to their general category (calf), and some corresponding identification means. The first column identifier could represent a visual tag number, and the second column could represent an RFID tag number. Depending upon how animals are received into the cow/calf operation, and based upon how a particular ranch desires to identify animals, the cattle may have one or more tags. As mentioned above, the preferred method of identifying animals would be through a retinal scan wherein a unique number would be assigned to each digital image of an animal's retina. Therefore, the numbers shown in FIG. 17 could also represent a digital file corresponding to a retinal image of a particular animal. FIG. 17 also shows other features to include the ability to select all of the animals within the north location for transfer, undo a move, or reset. To select one or several animals for transfer, a user would click the cursor on a particular animal(s) and then drag to the listing of animals within the south location. Of course, the transfer of animals from the north to the south location would only occur once an order had been fulfilled by a worker in the field who had actually transferred the animals, and confirmed that the animals had been moved.

Figure 18:
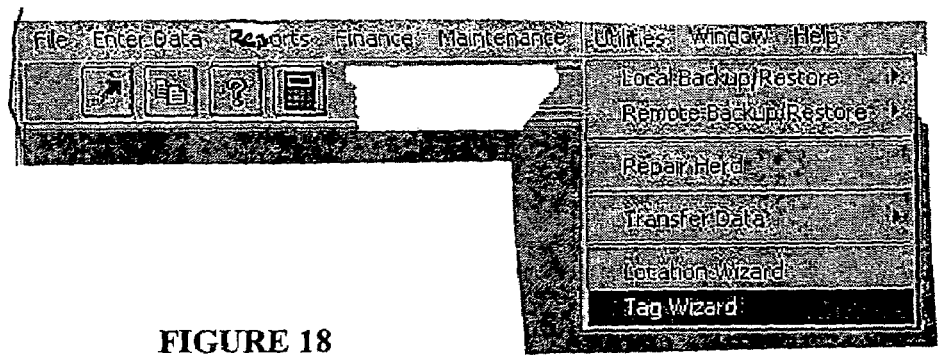
FIG. 18 illustrates another pull-down menu for entry of unique tag identifiers for each animal.

FIG. 18 illustrates another user screen in the form of a pull-down menu that allows the user to utilize a tag wizard function to enter unique tag identifiers to be assigned to each animal.

Figure 19:
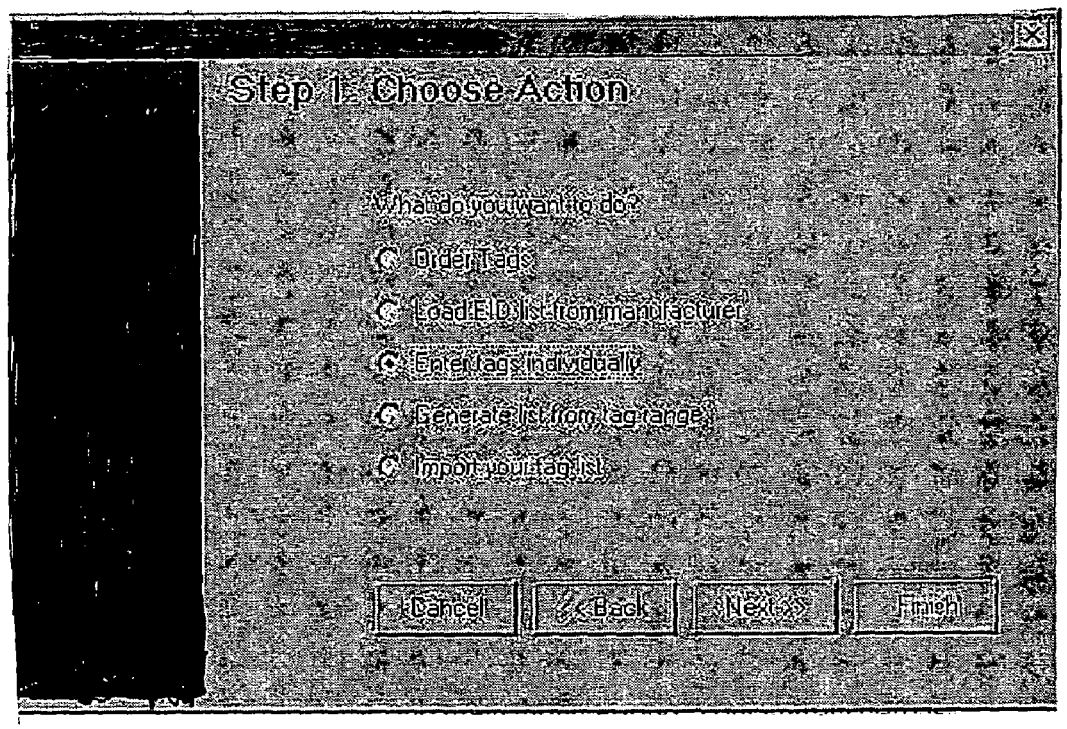
FIG. 19 illustrates a user screen for selecting various options to include ordering tags, loading tag information from a manufacturer, generating a tag range, importing tag listings, and entering individual tag information.

FIG. 19 illustrates a user selection screen where a user may select various options to include the ability to order tags, load tag information from a manufacturer such as predetermined set of tag numbers corresponding to a particular type of tag. This screen also allows the user to enter tag information into the database, generate a tag listing from a tag range which has been preconfigured for a designated location, or to import a tag list from yet another source such as from a third party who has already generated a tag list.

Figure 20:
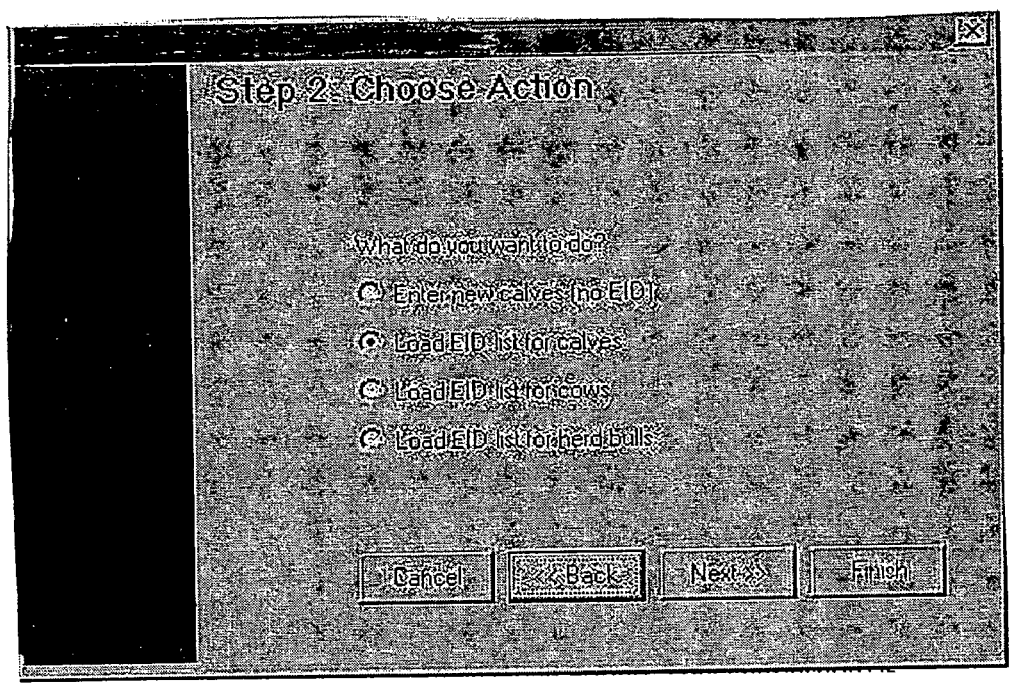
FIG. 20 illustrates a user screen for data entry of new tags to include various electronic identification information.

FIG. 20 shows the next selection screen if tags were chosen to be entered into the system individually. More specifically, FIG. 20 shows that the user can enter new calves, load an EID list for cows, or load an EID list for herd bulls.

Figure 21:
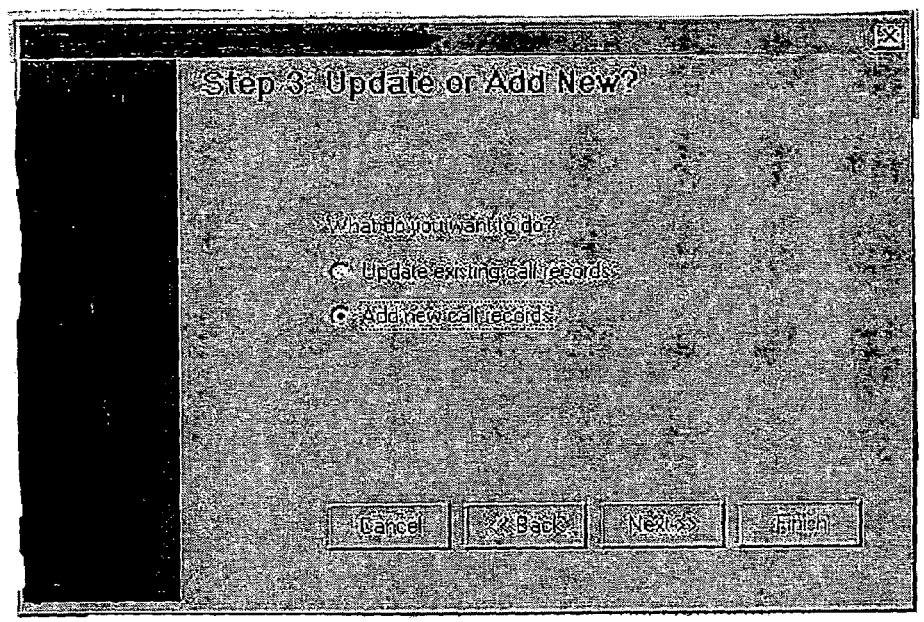
FIG. 21 illustrates a user screen for choosing whether to add a new calf record or to update an existing calf record.

FIG. 21 illustrates a selection screen if the "load EID list for calves" option was chosen from FIG. 20. This screen allows a user to choose whether to add a new calf record or to update an existing calf record.

Figure 22:
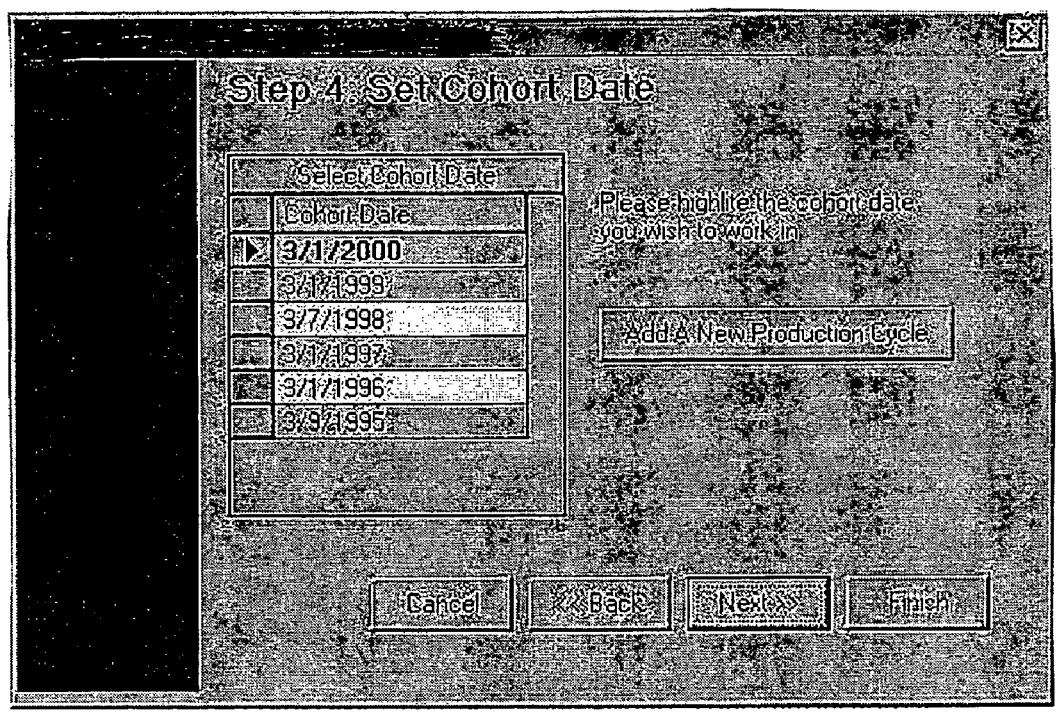
FIG. 22 illustrates a user screen for entering information on a particular animal into the system wherein a user sets a cohort date.

FIG. 22 illustrates the next user screen obtained once the user requests a new calf record to be added to the system. More specifically, FIG. 22 illustrates a data entry screen for entry of a particular animal into the system wherein a user sets a cohort date. The cohort date is simply an originating date for the animal and is either the actual birth date of the animal, or an estimated birth date.

Figure 23:
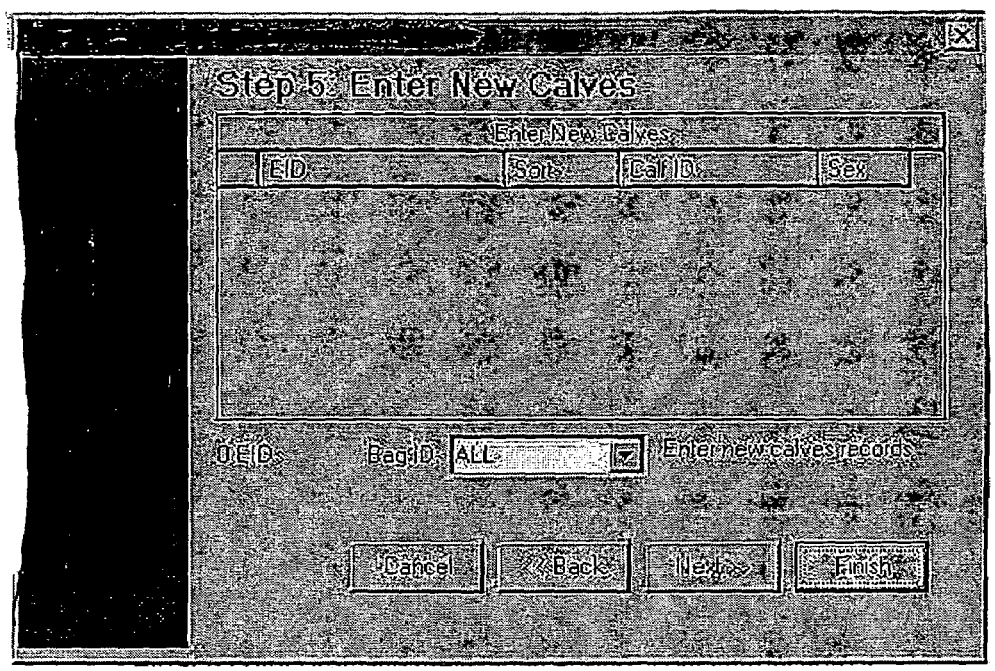
FIG. 23 is a user screen for assigning unique animal identification information such as an electronic identification number.

FIG. 23 is the next user screen provided once that particular cohort date is chosen wherein a calf is assigned a unique tag number such as an EID number, a sort identification corresponding to a particular grouping of animals, another identification means in the form of a separate calf ID, and identification of the sex of the animal. After data has been entered for each animal by completion of the data entry within the screen shown in FIG. 23, a particular animal has been uniquely identified and can be monitored by the system.

Figure 24:
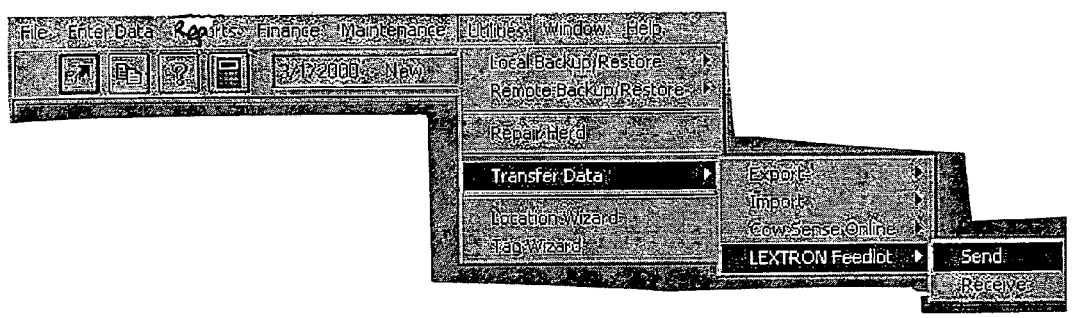
FIG. 24 illustrates another pull-down menu option from a user screen for enabling data transfer.

FIG. 24 illustrates a screen for another option from the pull-down menu which is a transfer data function allowing the user to export data, import data, review data records online, and to choose one or more particular operations such as a feed lot to send data to, or to receive data from.

Figure 25:
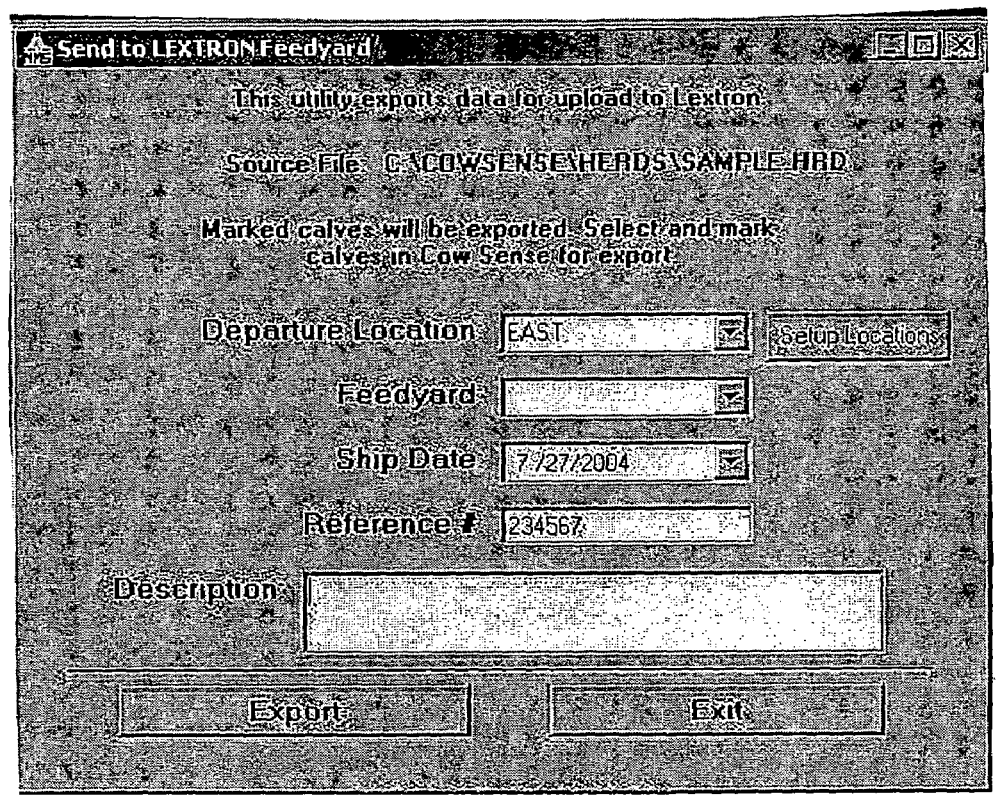
FIG. 25 is a user screen for sending data to a particular selected location.

FIG. 25 illustrates a user screen that allows the user to send data to a particular location for selected animals; for example, transfer of data from a cow/calf operation to a feedlot. This function is selected when, for example, it is desired to transfer animals from a cow/calf operation to a feedlot which must be prepared for receiving the animals. Typically, a group of animals is selected at a cow/calf operation for transfer to a feedlot, each animal being listed by their particular tag or identification number. By the export function shown in FIG. 25, not only is a simple listing of all the animals to be transferred sent to the particular feed yard chosen, but also other corresponding data that has been gathered about the animals which would include information such as medical treatment history, weight, sex, and owner.

Figure 26:
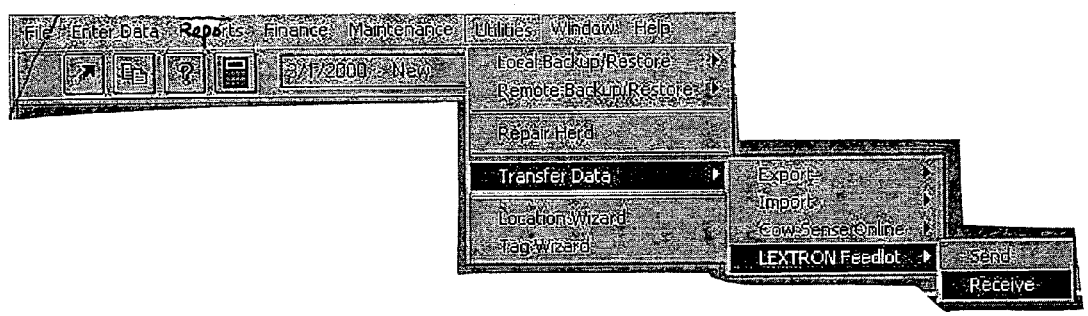
FIG. 26 is another pull-down menu from a user screen for receiving data from another location.

FIG. 26 is a user selection screen indicating that the user has chosen from the pull down menu to now receive data from another location. Data that a rancher may be interested in receiving from a feedlot would include growth rates and animal weights upon shipment to a packer.

Figure 27:
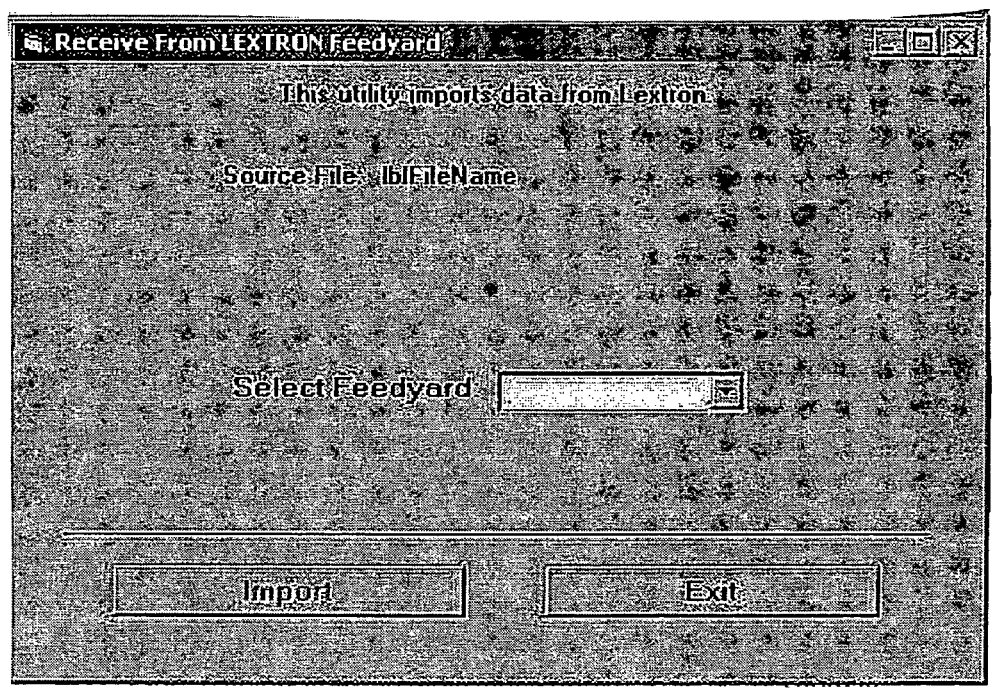
FIG. 27 illustrates a user screen for selecting a particular location for importing data.

FIG. 27 simply illustrates a screen that allows the user to select a particular feed yard for importing data.

As can be seen from the preceding discussion with respect to the cow/calf module, each animal which is received into a particular cow/calf operation is uniquely identified, is monitored as to the movements between locations/premises within a particular cow/calf operation, and data may be exported to other operations, and imported from other operations.

III. Grower/Feedlot Module

A. Animal Health Sub-Module

The first sub-module discussed below is an animal health function allowing a user to record and analyze all treatment and processing events for each individual animal while the animal resides at a particular grower/feedlot location. The term "feedlot" as used below also may describe grower operations; therefore, the following discussed functionality is applicable to grower operations as well.

Figure 28:
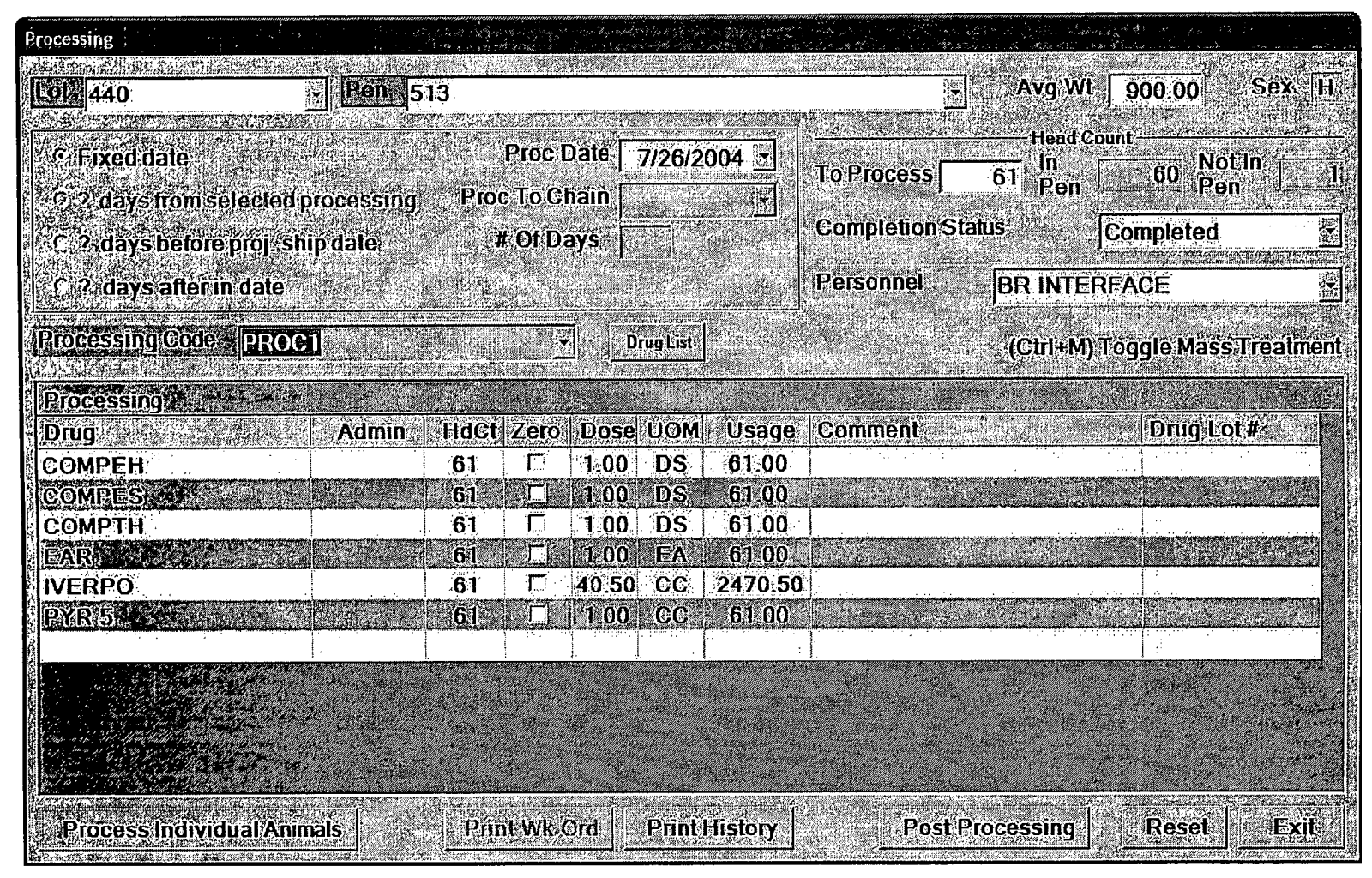

FIG. 28 illustrates a user screen allowing data entry for initial processing of animals as they are received into the feedlot. More specifically, FIG. 28 allows data entry for recordation of medications administered to animals located at a particular lot and pen number. The animals located at a particular lot and pen number are a known group of animals that are each individually identifiable by their corresponding tags. FIG. 28 indicates that each of the animals are to be recorded as receiving the specified listing of drugs. The user has an option of printing the screen in the form of a work order so that a feedlot worker can then administer the drugs. Once the work order has been completed, the user can then select the "Post Processing" button which will record that each of the animals within the particular lot and pen number have received the drugs. Because each animal within the pen and lot numbers are known, each one of the individual animal records in the local database or central database is updated to reflect that the animal has received the drugs. A particular listing of drugs to be administered can be chosen from preselected or preconfigured processing codes that represent either standard protocol treatments, or tailored treatments can be created by the user. Therefore, the user can select from the processing code listing the various treatments to be completed and posted to the system database(s). It is also possible to individually process animals by selecting the "Process Individual Animals" button. Thus another user screen would be shown allowing a user to select a particular animal, and the user again could chose treatment from a processing code, or the user could create a tailored treatment.

FIG. 29 illustrates a sample listing of drugs from the drug list button of FIG. 28 that allows the user to add or delete a particular drug to the available listing of drugs. Therefore, it is evident that the standard treatment protocols as well as tailored treatments can be modified by the user if required.

Figure 30:
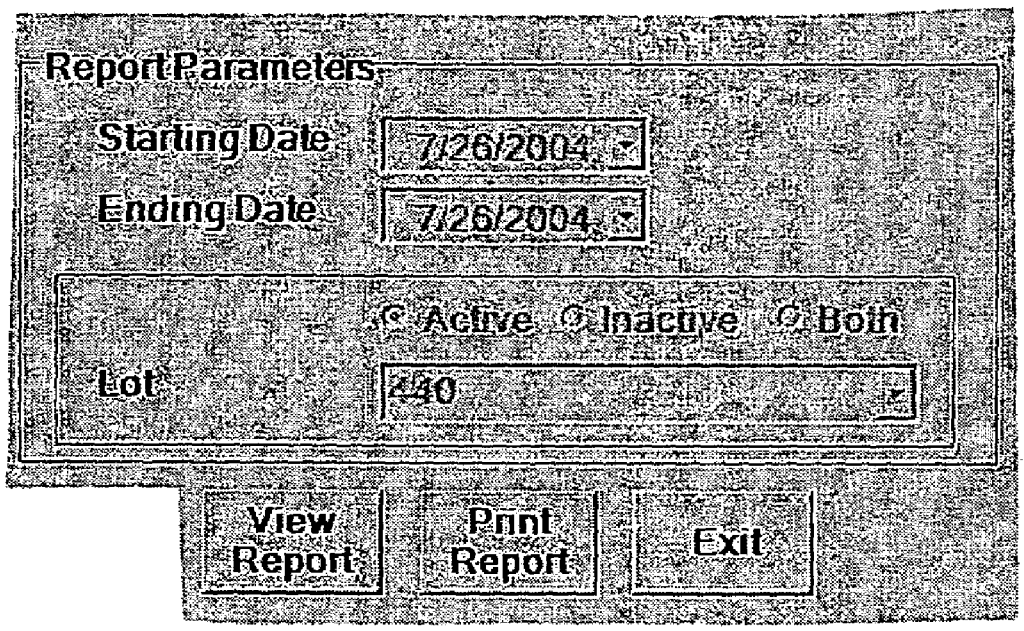
FIG. 30 is a user screen for selecting report showing the processing history of the particular animal or group of animals.

FIG. 30 illustrates a user screen that allows a user to select a report showing the processing history of a particular animal or a group of animals.

Figure 31:
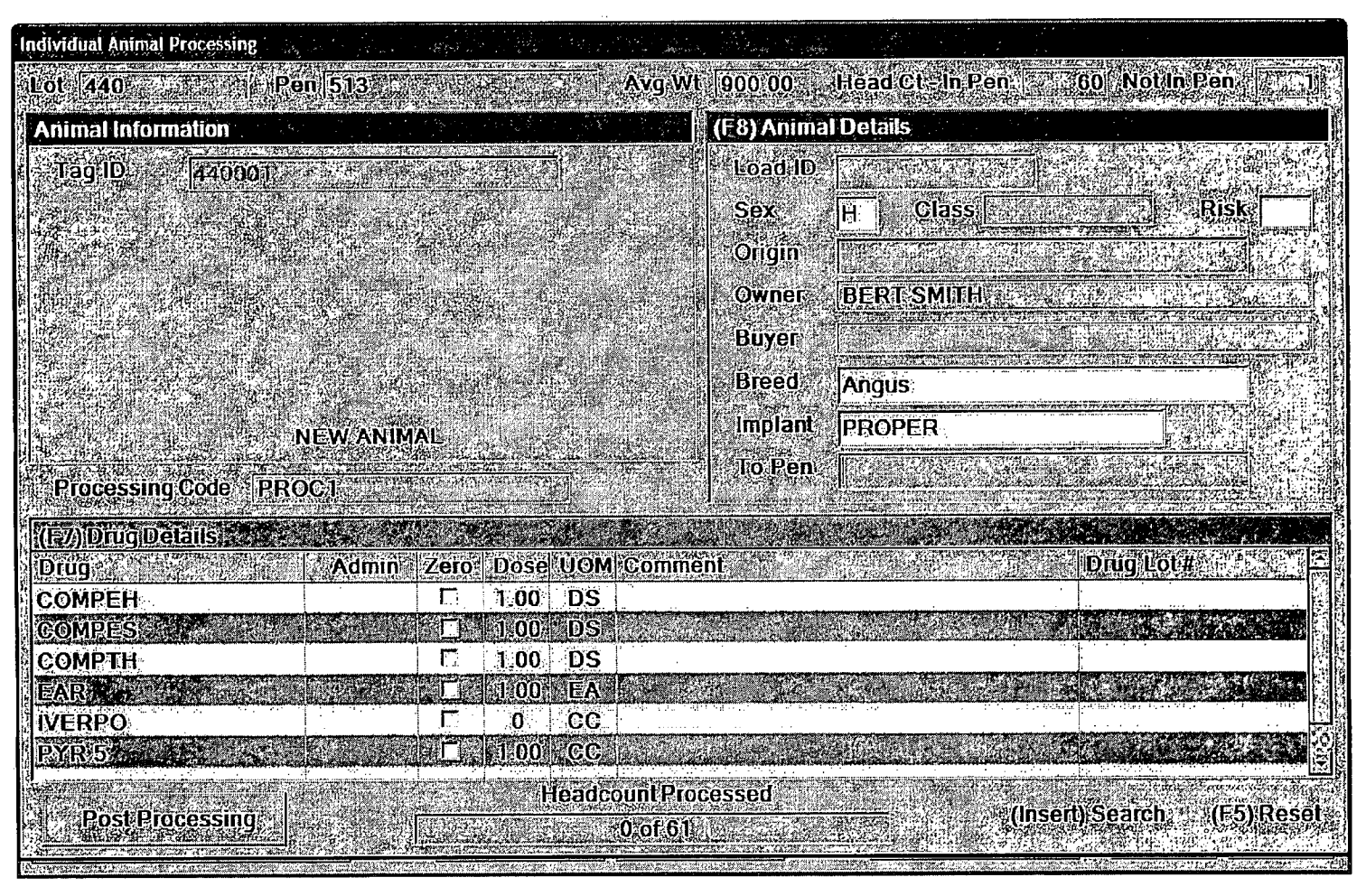

FIG. 31 is another user screen for individual animal processing where instead of processing animals by a particular pen and lot number as initially described above with respect to FIG. 28, the user also has the ability to individually process animals. As shown, a unique tag ID for a particular animal chosen appears on the screen as well as the current location of the animal at the corresponding pen and lot number. The processing to be recorded is shown in the form of the administration of one or more drugs to the animal according to a particular processing code chosen. FIG. 31 also illustrates that within the particular lot and pen, there are sixty animals present within the pen and one animal not present in the pen, which could account for a particular animal being at a hospital location, or some other location at the feedlot. As treatment for each animal is posted, the head count processed as shown at the bottom of the screen would automatically update. A user could confirm that all the animals within the pen have been treated once the head count reach the total number of animals assigned to the particular pen. The posting of a record indicating that an animal was treated in accordance with the screen in FIG. 31 is preferably done at chute side. Thus, once an animal had been treated, the user would simply click on the "Post Processing" button which would then post that particular information to the database thereby indicating that the animal had been treated with the listed drugs. Alternatively, a report could be printed for each animal and a feedlot worker would then use the printout as a work order. The worker would complete the treatments, and then would return to the work station to report that the processing had been completed. Then, the user would post each of the records to the database.

Figure 32:
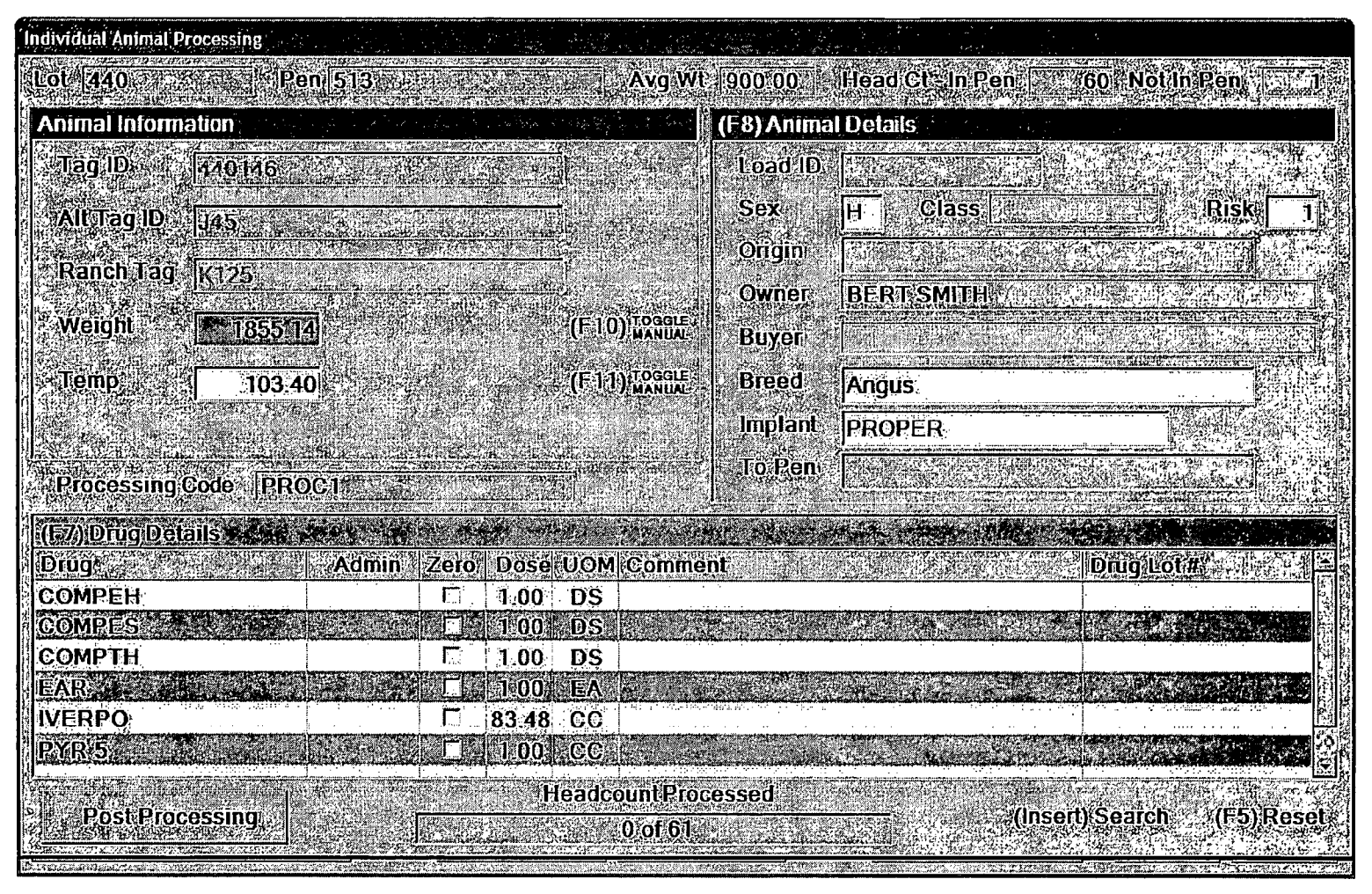

FIG. 32 is another example of an individual animal processing screen that allows the user to enter data about the animal as it is being processed. More specifically, FIG. 32 illustrates that the user could enter a weight and temperature, as well as information about the owner of the animal. Of course, for all the data entry screens, a user cannot randomly assign a new or different identification to a particular animal, nor create fictitious animals within the system. Thus, once an animal has been initially identified and is recorded as being an active animal within the particular feedlot location, the identification numbers that have been assigned to the animal cannot be altered or changed. In exceptional circumstances, it may be necessary for a user having administrator level privileges to make a change to one or more identification numbers; therefore, some override could be provided within the system that allows correction or modification to existing identification records.

Figure 33:
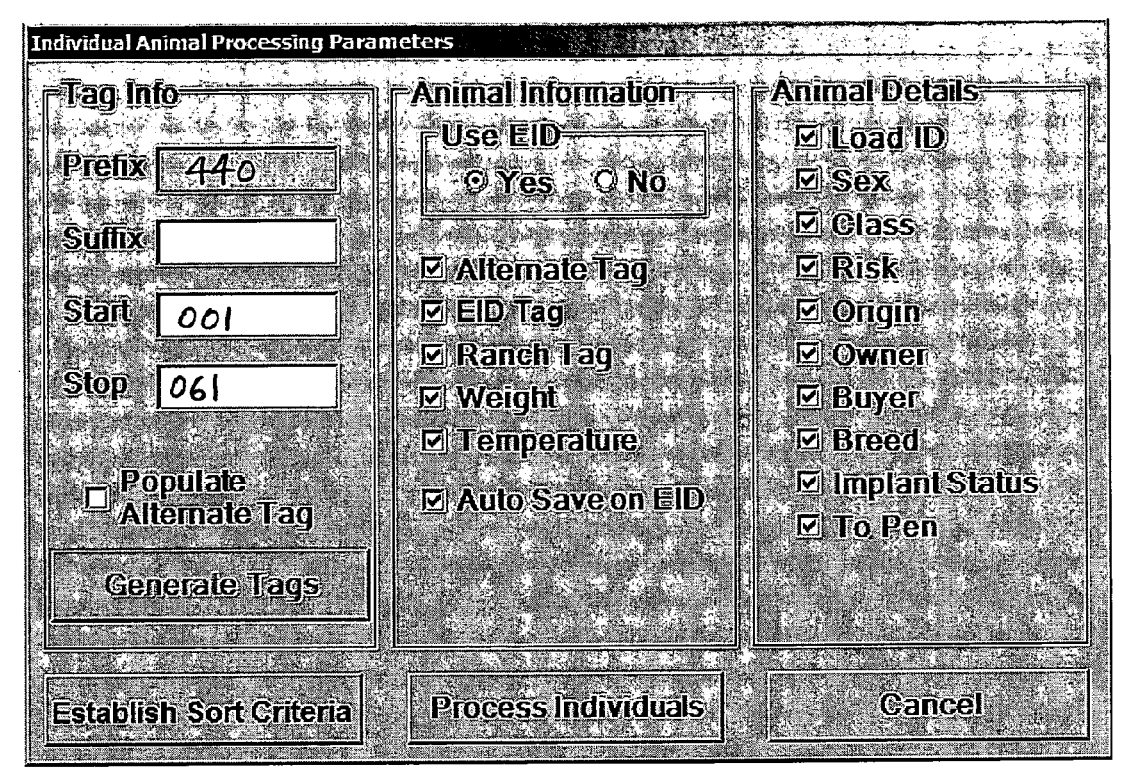

FIG. 33 is another user screen that allows the user to select particular individual animal processing parameters to be entered and recorded. This screen also allows the user to generate special feedlot tags that can be used for supplementary identification purposes while the animals are in the feedlot. It should be understood that the initial identification of an animal in a cow/calf operation in terms of identifying each animal by a unique identification number is not reentered at the feedlot; rather, additional identification means may be provided at the feedlot that allows a feedlot to move, treat, or ship the animals. Ultimately, a single data record is available for each individual animal that allows one to view a complete medical treatment history for each animal, as well as locations where the animal was located on specific dates.

Figure 34:
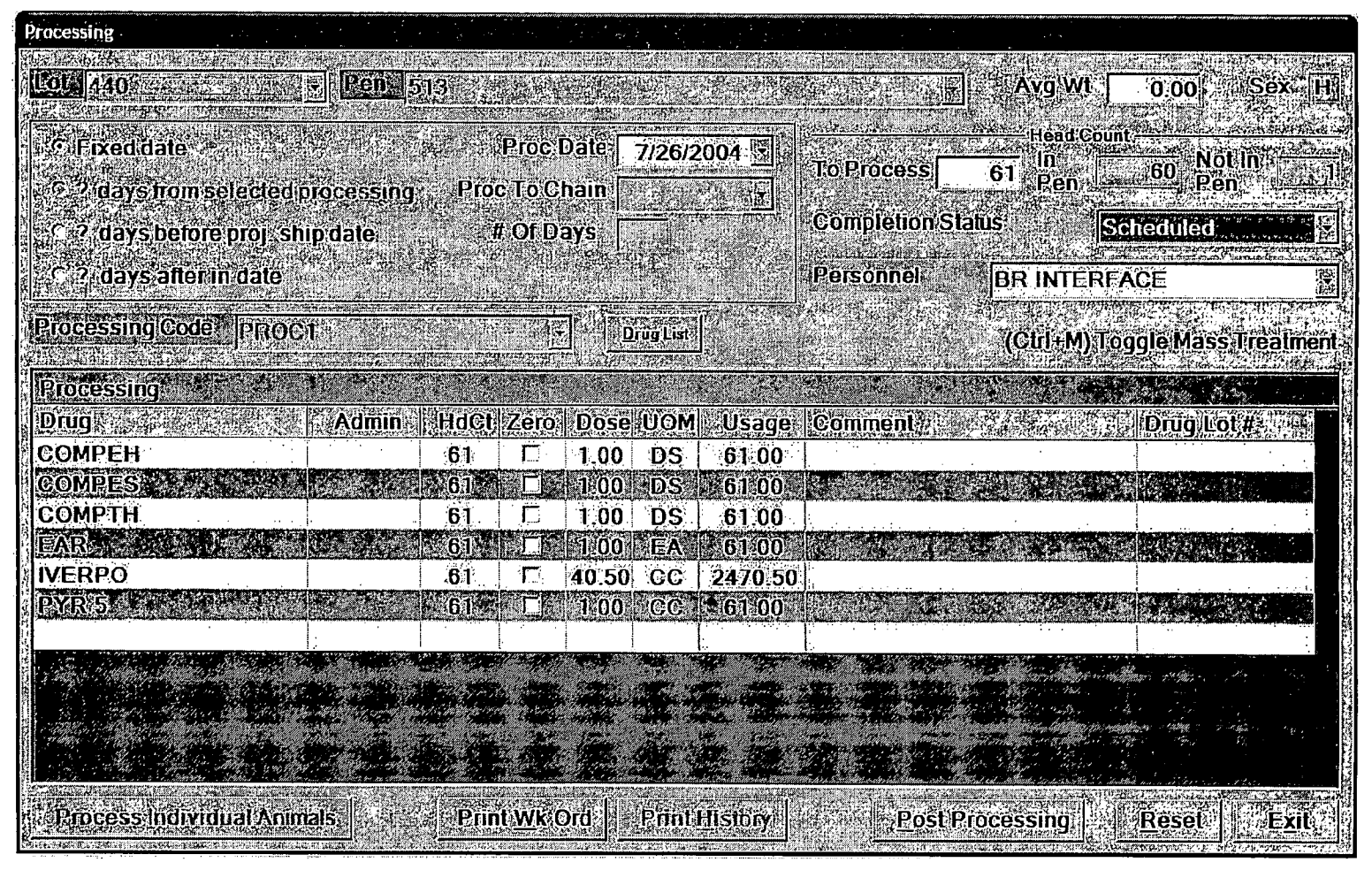

FIG. 34 is another user screen that may be used to schedule treatments of individual animals or groups of animals. In the example shown in FIG. 27, the user desired to set Jul. 26, 2004 as the fixed date to complete processing of Processing Code 1 (PROC 1) for the 61 animals that have been assigned to Lot 440 and Pen 513.

Figure 35:
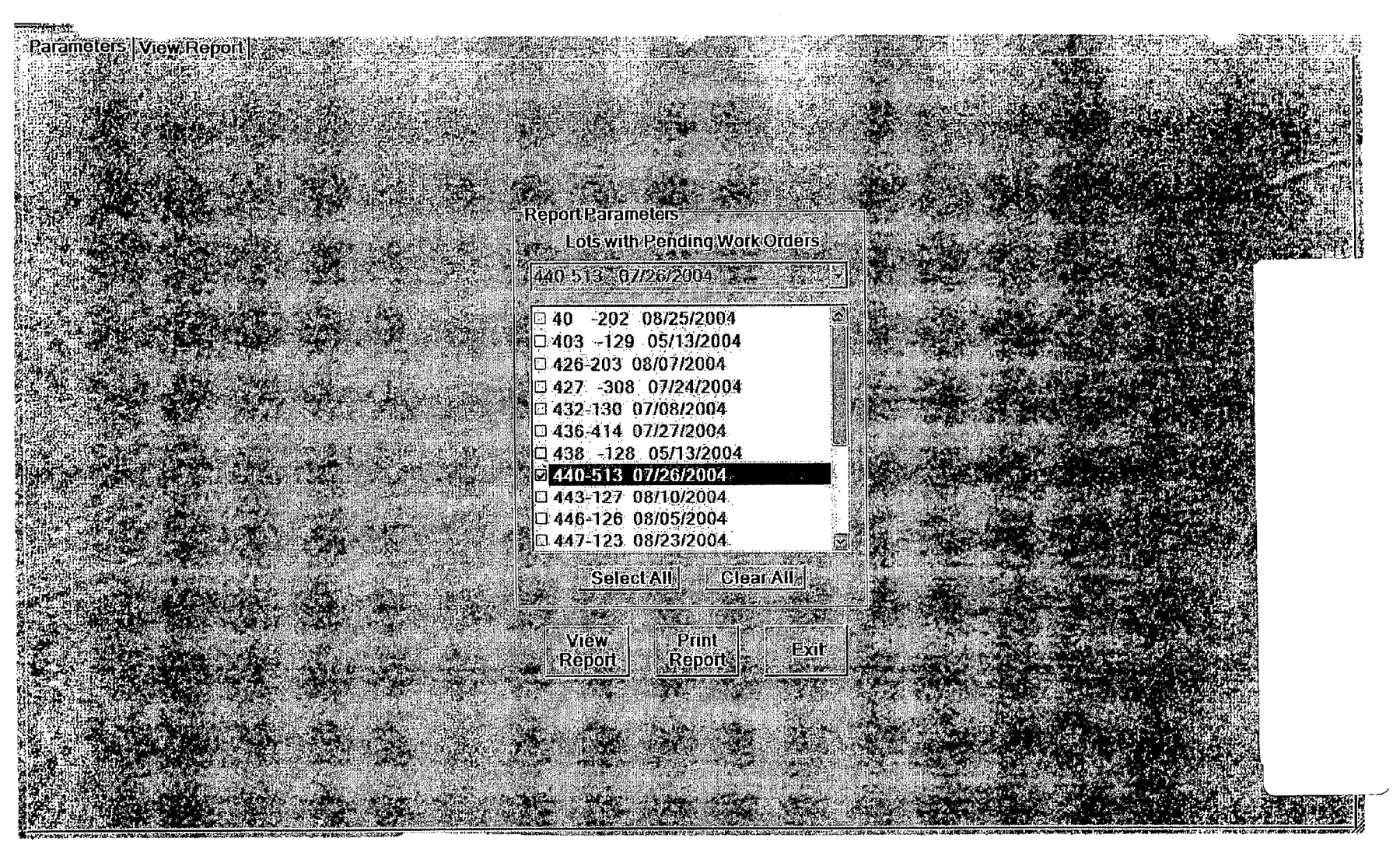

FIG. 35 is another user screen that indicates pending work orders, allowing the user to select a particular work order for viewing. Accordingly, the user in FIG. 28 has chosen to view the scheduled processing for Lot 440 Pen 513 on Jul. 26, 2004. The user could then view or print the report to determine what had been scheduled.

FIG. 36 is a user screen showing a sample report corresponding to the pending work order chosen from FIG. 35. The report lists a head count, lot, pen, and explanation of particular processing to be completed, namely, the administration of various drugs to each of the animals.

Figure 37:
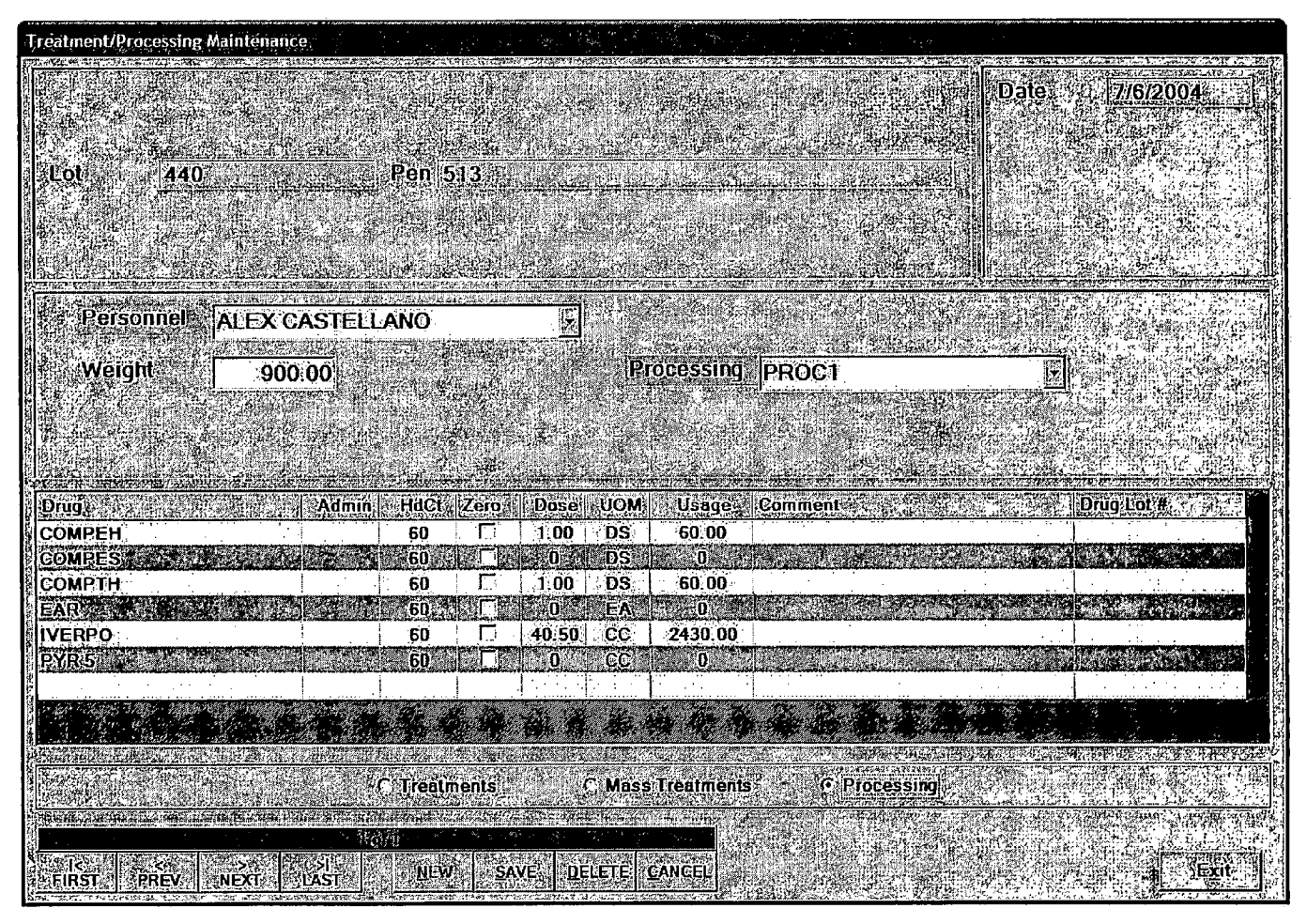

FIG. 37 is another user screen which can be used to modify previously entered data regarding a particular processing that has been already posted for a group of animals. For example, it may be found later that although a particular work order had instructed the administration of a particular amount of a drug, the actual amount of a drug administered was different than ordered. The screen shows the name of the person who originally completed the processing. The user could reenter data such as dose or usage and then add a comment as to why data was reentered.

Figure 38:
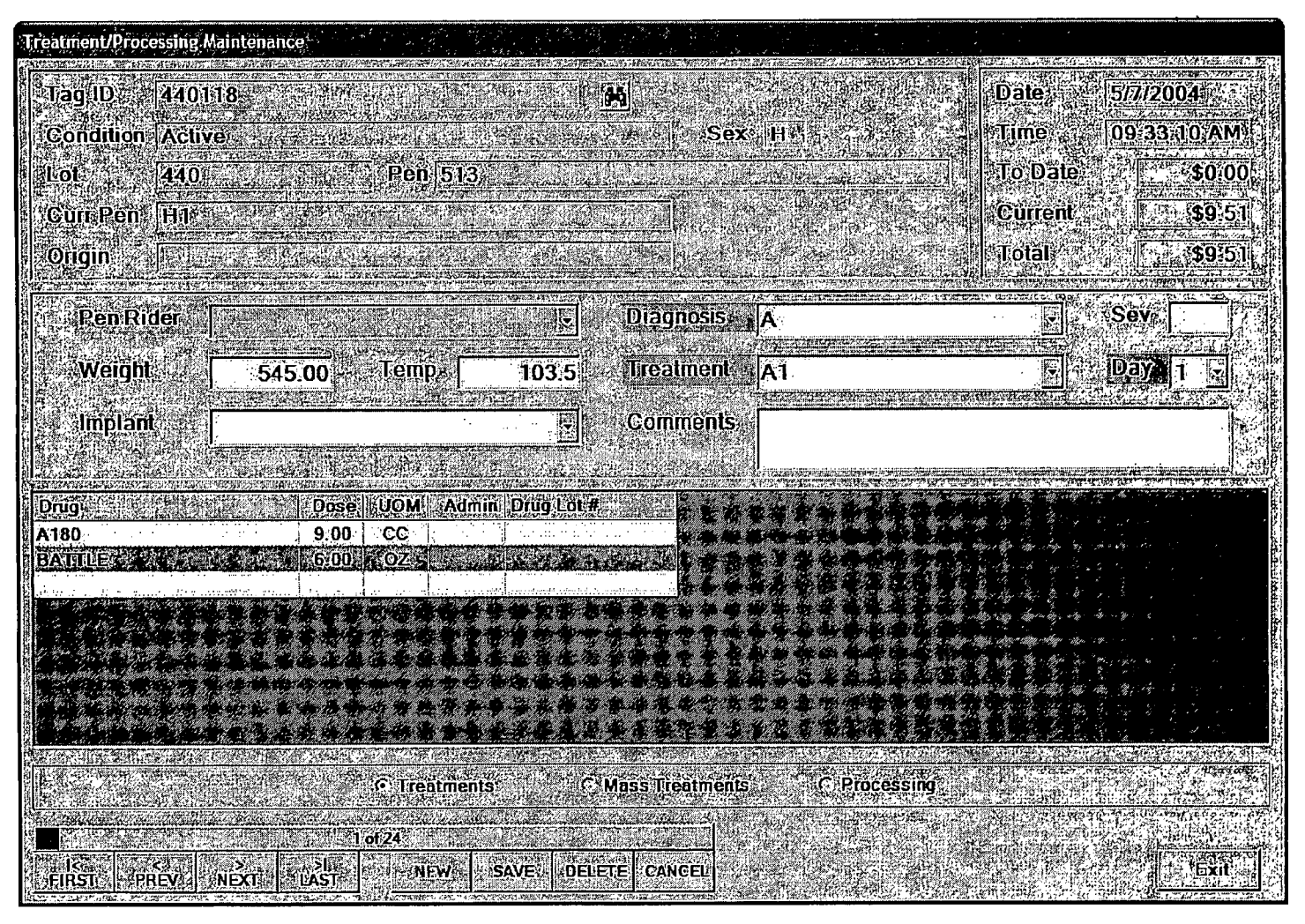

FIG. 38 is another user screen that can be used to modify previously entered data regarding treatment/processing of a specific animal. As with FIG. 37, the user could use the screen shown in FIG. 38 to modify data that had been previously entered, such as dose.

Figure 39:
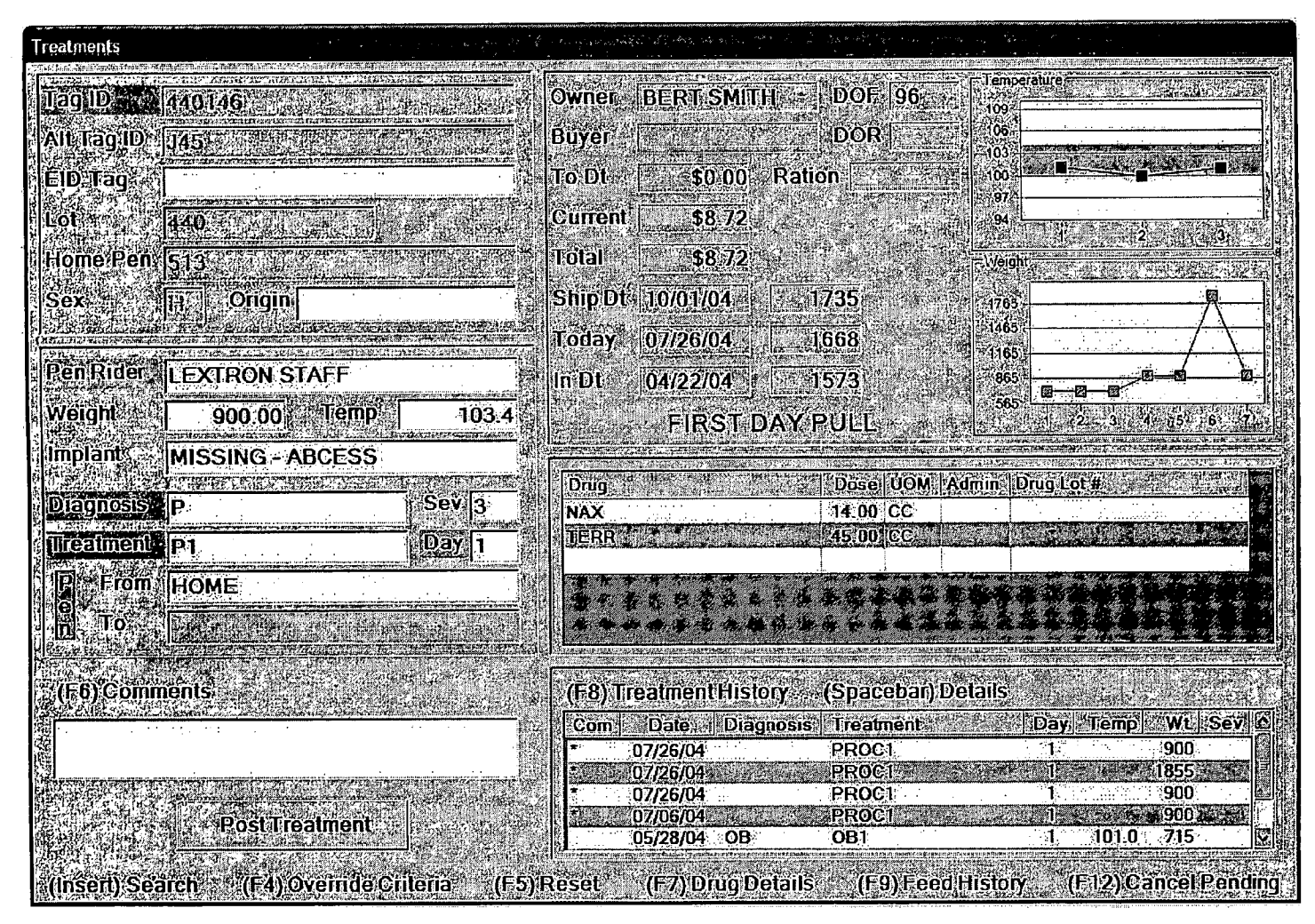

FIG. 39 illustrates another user screen allowing data entry for treatment. FIG. 39 also shows additional information about the particular animal such as temperature and weight graph, owner information, and treatment history of the animal. In the example shown in FIG. 39, an animal is to be administered two specific drugs identified by the abbreviations "NAX" and "TERR." The user would again preferably be located at chute side as the treatment occurs, and then once the treatment was completed, the user would click on the "Post Treatment" button to record the treatment.

Figure 40:
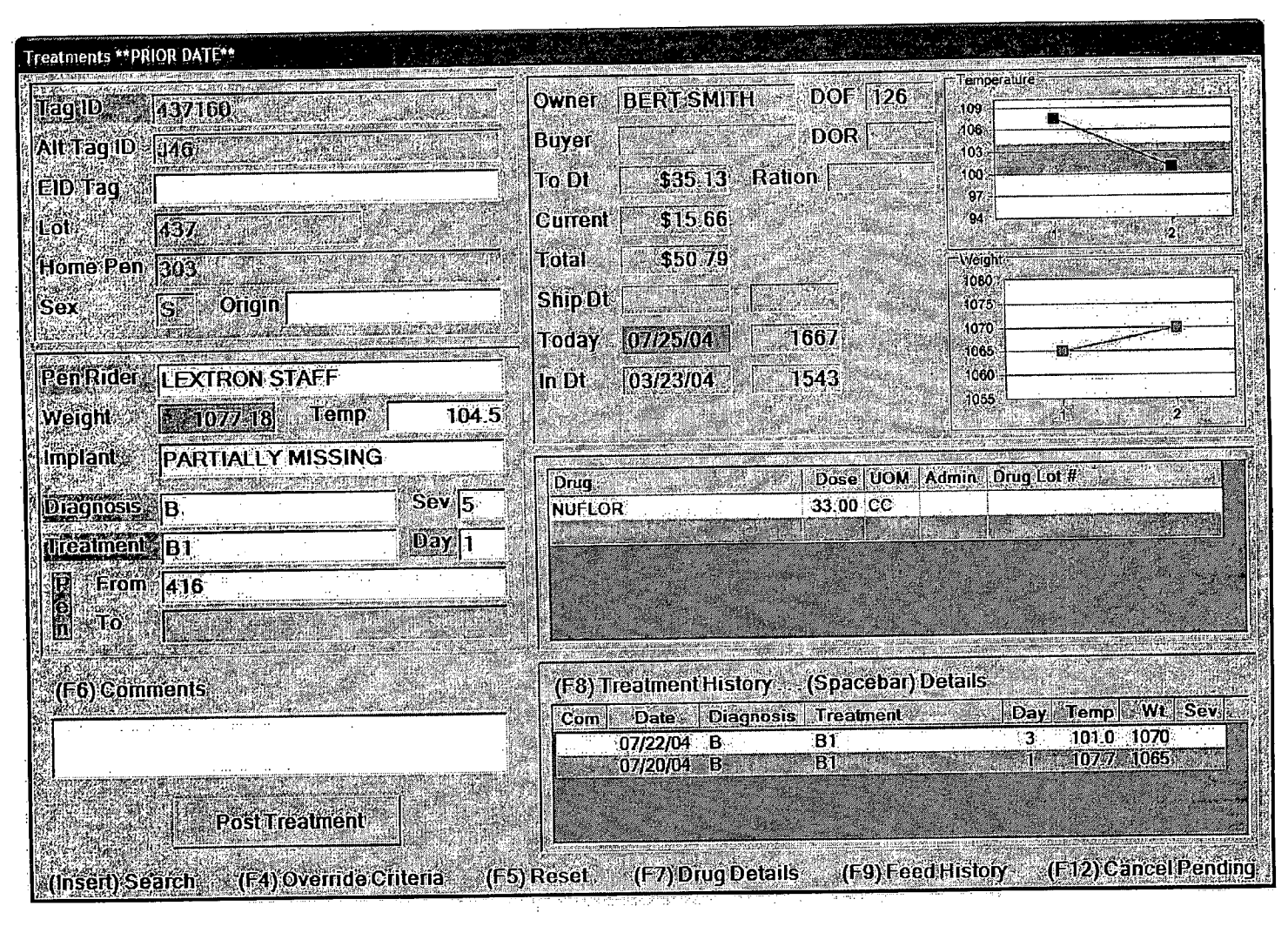

FIG. 40 is another user screen indicating that data for a particular treatment is now being entered for a treatment that was actually completed on a prior date. For example, if a user is unable to be located chute side when treatment occurs, confirmation that a treatment has occurred may not be forwarded to the user for some time after the treatment has taken place. Therefore, this particular screen simply alerts the user to the fact that they are now entering data regarding a treatment that has previously occurred. In the example of FIG. 40, the date of the treatment was Jul. 25, 2004 (the date shown in the "Today" block), and the date that the user is posting treatment would be some day subsequent to Jul. 25, 2004.

Figure 41:
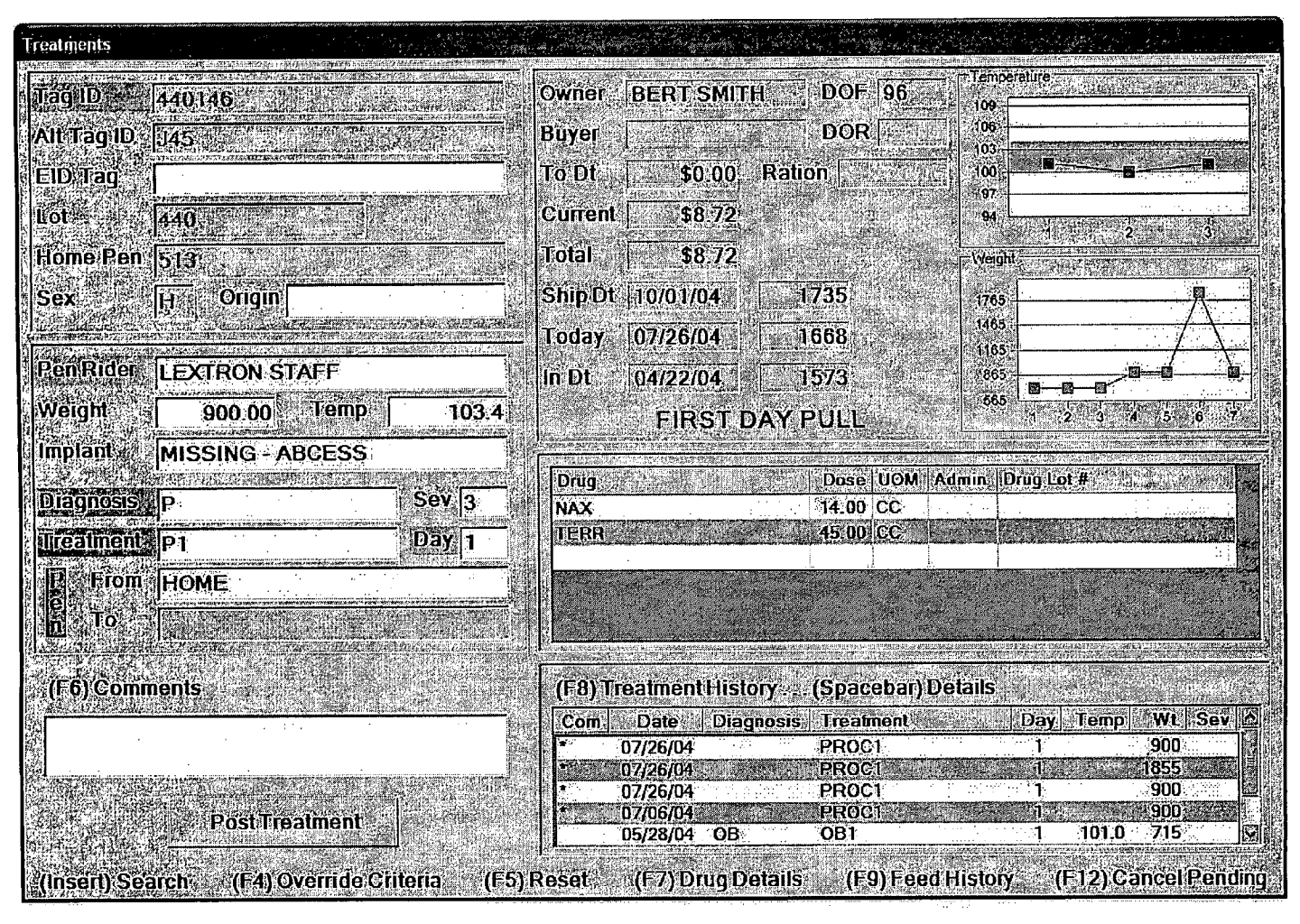

FIG. 41 illustrates another user screen where a user has selected from the treatment history listing a particular treatment date. Once selecting a particular treatment date, another window opens listing the drugs that were administered during that treatment. A user can review a summary of a treatment-by-treatment code, and can also review a specific listing of each of the drugs that were administered during the treatment.

Figure 42:
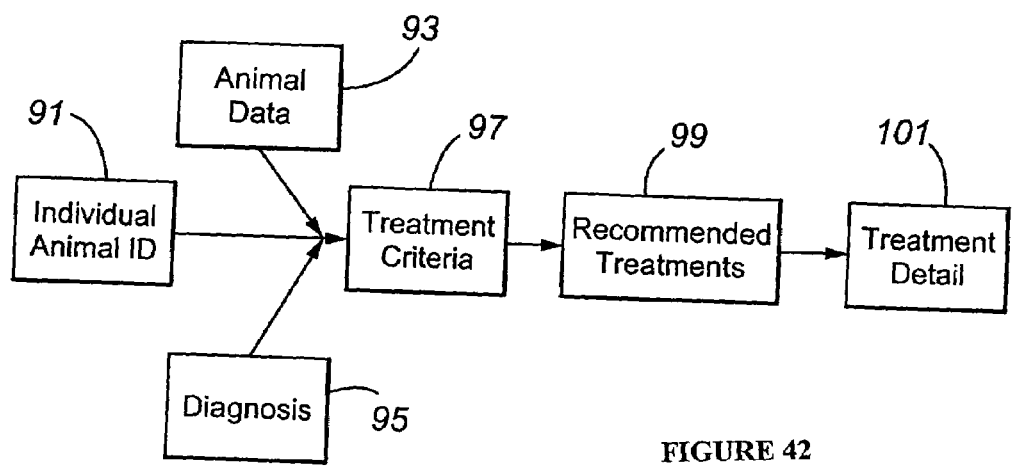
FIG. 42 is a schematic diagram depicting an automated recommended treatment selection process.

Referring to FIG. 42, the schematic diagram depicts an automated recommended treatment selection process. First, the individual animal identification is entered into a treatment screen as by manual entry (typing in the tag ID) or through use of an EID tag reader, as shown at Block 91. Once the animal ID has been entered, the system then locates all animal data stored in the central database or any other peripheral databases associated with this particular individual animal ID. This animal data located is represented at Block 93. The user will next enter an identifying diagnosis code, shown at Block 95, based on the evaluation of the animal. The diagnosis code matches a particular symptom or symptoms of the animal based upon knowledge of the treating veterinarian. The combination of the animal data with the diagnosis is compared with the treatment criteria, as shown at Block 97. The treatment criteria can comprise a listing of animal characteristics or other recorded data about the animal, as well as criteria that is defined by its own formula/algorithm. If the animal data matches the rules set for the criteria, a recommended treatment is produced, as shown at block 99. For example, if the particular animal is recorded as having a fever and respiratory problems, those data entries may match a set of criteria wherein an alogorithm/mathematical relationship is applied to the criteria results in a recommended treatment for pneumonia. The recommended treatment appears on a user interface screen or printed report to include an explanation of how to treat the animal. If the recommended treatment is accepted by the user, then the system next retrieves the associated drugs, drug dosages, administration site, and any other treatment detail associated or assigned with the particular treatment, shown at Block 101. If the treatment is executed, the user inputs data to reflect which treatment was conducted, and the detailed treatment data then becomes additional animal data 93 that is stored for the particular animal. Although a treatment criteria and recommended treatment may be established, it shall be understood that the treating veterinarian may also decide to adopt another treatment that is not recommended and in such case, the particular treatment data is also entered into for the particular animal data, to include a record of any drugs or therapeutic agents provided to the animal.

B. Feed Management Sub-Module

A feed management sub-module is also provided within the grower/feedlot module. The purpose of the feed management module is to manage the assignment, calling, delivery and analysis of an animal feeding operation at the feedlot. The module allows recordation and reporting of all activities occurring during feeding, and also provides capability to interface the detailed feeding information to external financial systems, feed delivery systems within a particular feedlot operation or grower operation, as well as feed mill batching systems within a particular operation. Furthermore, the module also facilitates the assignment of types and amounts of rations to the various locations within the feedlot, the assignments which take into consideration various animal movements, receipt of new animals, shipment of animals from the feedlot, and many other factors that may alter the type and amount of rations to be delivered to each location within the feedlot. The feed management module data is stored at the local server databases or the central database, and therefore, the data can be fully integrated within the animal health module and all of the modules of the data processing system.

C. Animal Inventory Sub-Module

FIGS. 43-58 disclose an animal inventory sub-module that is used to control, record, and report on all transactions that effect the inventory of animals that are entered into the data processing system. Basic functionality within the animal inventory module includes detailed management of receiving, movements, shipments, deads, railers, and realizers. The entries for each of these functions enable the data processing system to assign a location to each individual animal to ensure that the status of an animal is updated within the system. For example, once an animal is shipped from the feedlot to a packer, no further data can be entered concerning that particular animal at the feedlot location unless corrections are being made to previously entered data. Thus, data from another animal cannot mistakenly be entered for a shipped animal, and vice versa.

Figure 43:
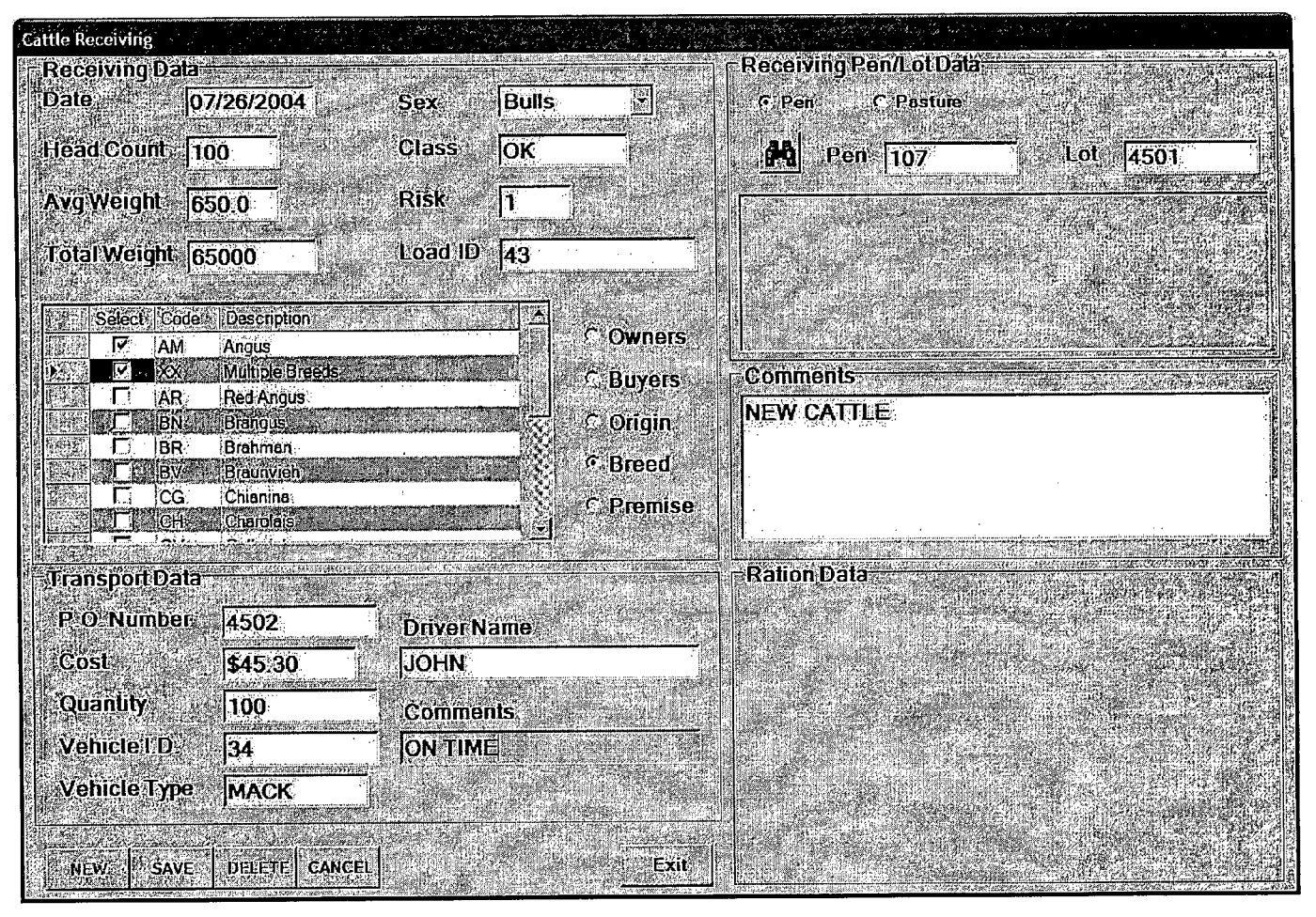

FIG. 43 is a user screen illustrating data entry to record receipt of animals that are being received from another location such as a ranch or grower operation, and wherein a specified group of animals are to be initially assigned to a single pen and lot. As shown in the example of FIG. 43, a head count of 100 cattle were received on Jul. 26, 2004, the group having multiple breeds, the transport data indicating that the 100 cattle were received on Purchase Order Number 4502. The user would enter all of the appropriate information as shown in FIG. 43 and assign the group of incoming cattle to the desired pen/lot or pasture. The data entry would be completed by pressing the "Save" button.

Figure 44:
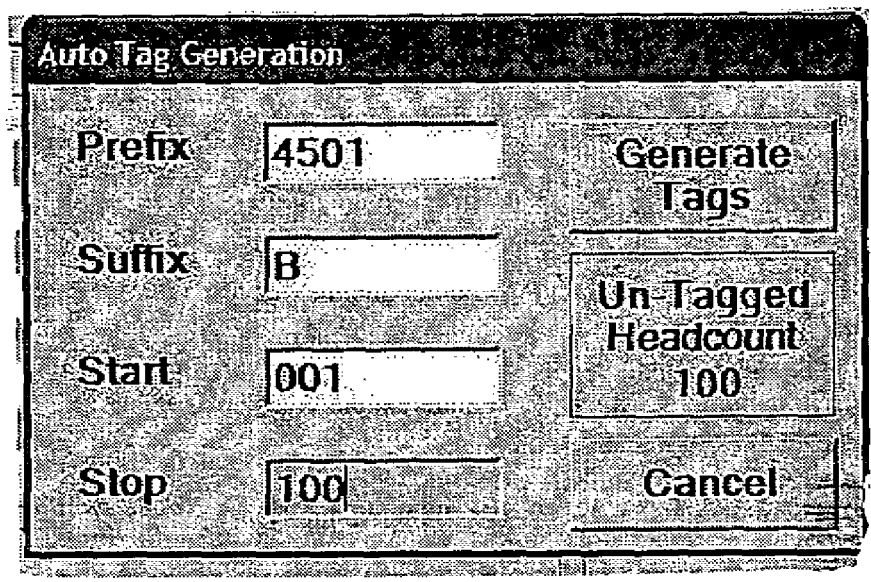
FIG. 44 illustrates a user screen for generating a feedlot tag.

FIG. 44 illustrates a user screen wherein the user can generate a feedlot tag to be assigned to each of the incoming cattle. Accordingly, the "Auto Tag Generation" option is illustrated wherein the user identifies the group of tags by prefix and suffix, and a total number of tags to be generated.

Figure 45:
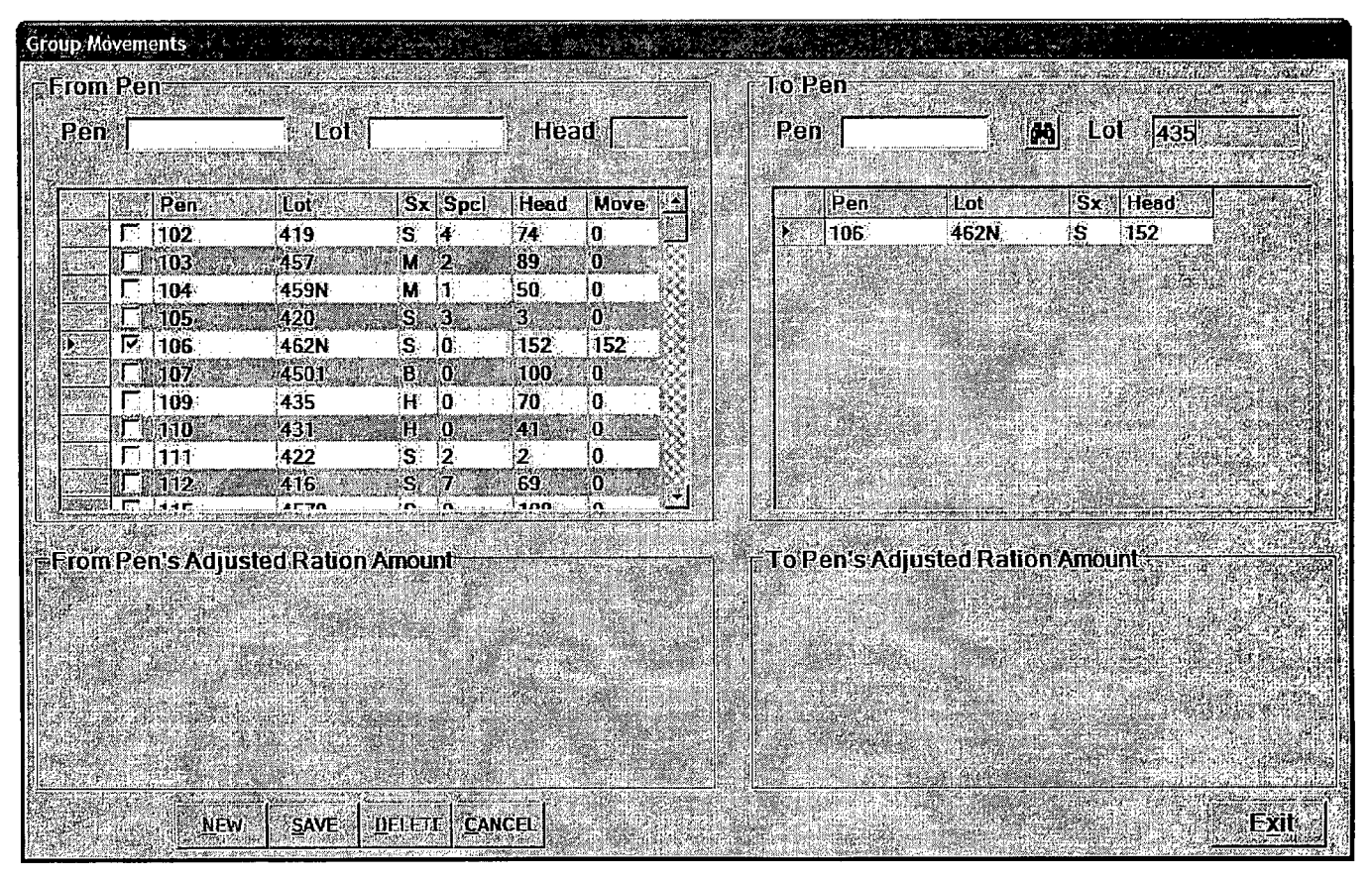

FIG. 45 is a user screen illustrating how to record group movements of animals. In the example of this figure, all of the animals residing in Pen 106 Lot 462N are to be transferred to Lot 435. Accordingly, the user would check the appropriate block for Pen 106 Lot 462N on the left side of the screen, and then would enter Lot 435 on the right side of the screen as the desired location to which the animals are to be recorded as being transferred to. Also, the screen will show the adjusted ration amounts after the transfer has been saved/posted. If there are any animals left within the pen and lot losing animals in the transfer, a lesser amount of ration would be shown in that losing pen and lot. Accordingly, a gain in the amount of ration would be listed for the gaining pen and lot based upon the number of animals being added to that location. An algorithm is provided in the system which automatically calculates the adjusted ration amounts in both the losing and gaining locations. This algorithm is updated continuously based upon the number of cattle in each location, the identified individual animals in each of the locations, and the prescribed rations for each animal.

It should also be understood that based upon the organization of a particular feedlot location, the pen number could correspond either to a more general or more specific location, and the particular lot number could also correspond to either a more general or more specific location. In other words, there could be a number of lot numbers assigned to a particular pen, or a number of pen numbers could be assigned to a particular lot. In the example screen shown in FIG. 45, the particular lot number is a subset of a particular pen. However, if a feedlot is arranged so that pens are subsets of lots, then transfers could be recorded as being between various lots. Of course, transfers could also be recorded between pens and lots even if the pens and lots are subsets of more general locations. As also discussed above, recordation of group movements would only occur after a work order had been fulfilled, and a feedlot worker was able to confirm that in fact the movement had taken place. Ideally, work stations would be set up within the feedlot at locations so the person recording the group movements could actually witness the movements.

Figure 46:
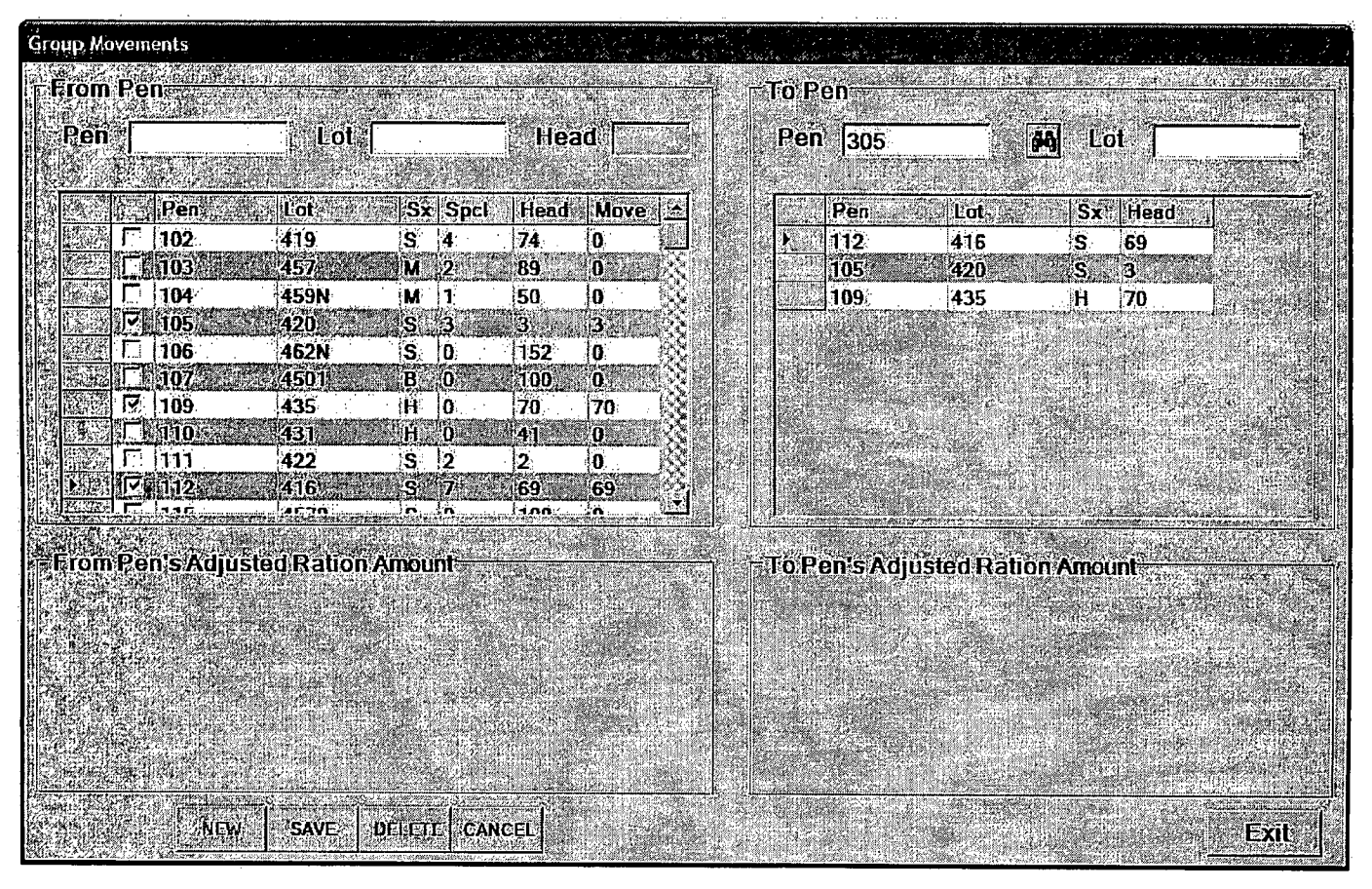

FIG. 46 illustrates another group movement, but instead of the movement of just one group of animals from a particular pen, multiple pens are being transferred to another pen. In the example, Pens 105, 109 and 112 are being recorded as moved into Pen 305.

Figure 47:
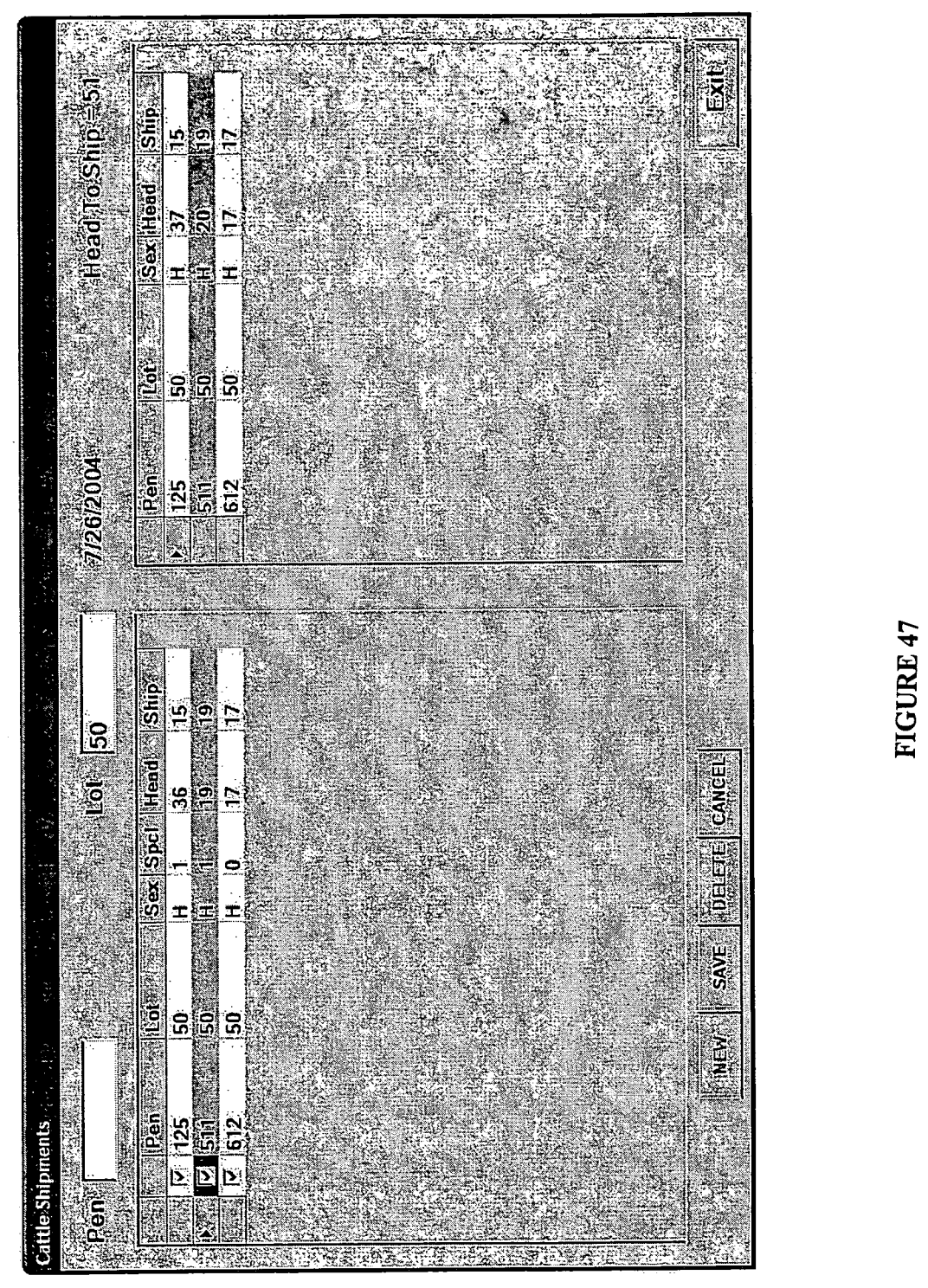

FIG. 47 illustrates another user screen wherein cattle shipments can be recorded. More specifically, FIG. 39 illustrates a situation in which cattle found within various pens are ready for shipment to another location, such as another feedlot, or to a packer. In order to record this transfer, the user would simply check the box on a particular pen having animals that were shipped, and then click on the save button to enter the shipment. In the example of FIG. 47, 51 head of cattle were shipped from Pens 125, 511, and 612. Only selected animals were shipped from each pen as shown in the head count versus the ship count. Each animal to be shipped from each pen was previously identified by the user in another user screen which allows the user to select each individual animal to be shipped in a subsequent group shipment.

Figure 48:
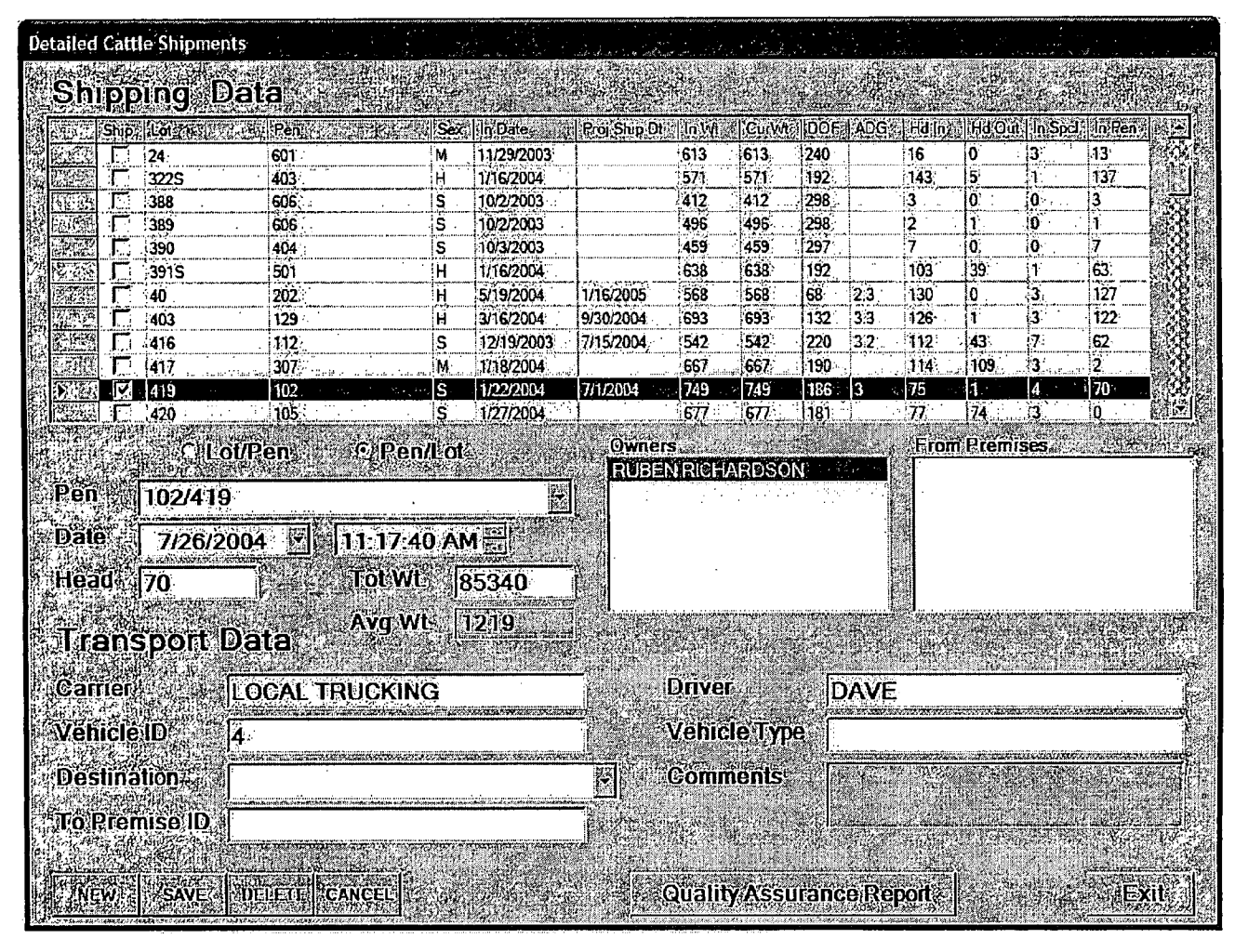

FIG. 48 is another user screen illustrating a more detailed listing of information for recordation of a particular animal shipment. A user would simply click on the lot and pen shipped by checking the appropriate box, and then complete the information as to the particular transport data, i.e., the carrier, vehicle ID, destination, and new premise ID. The shipment data can be entered by clicking on the Save button. Either individual lot/pen locations or multiple lots/pens may be recorded as shipped with the same transaction.

Figure 49:
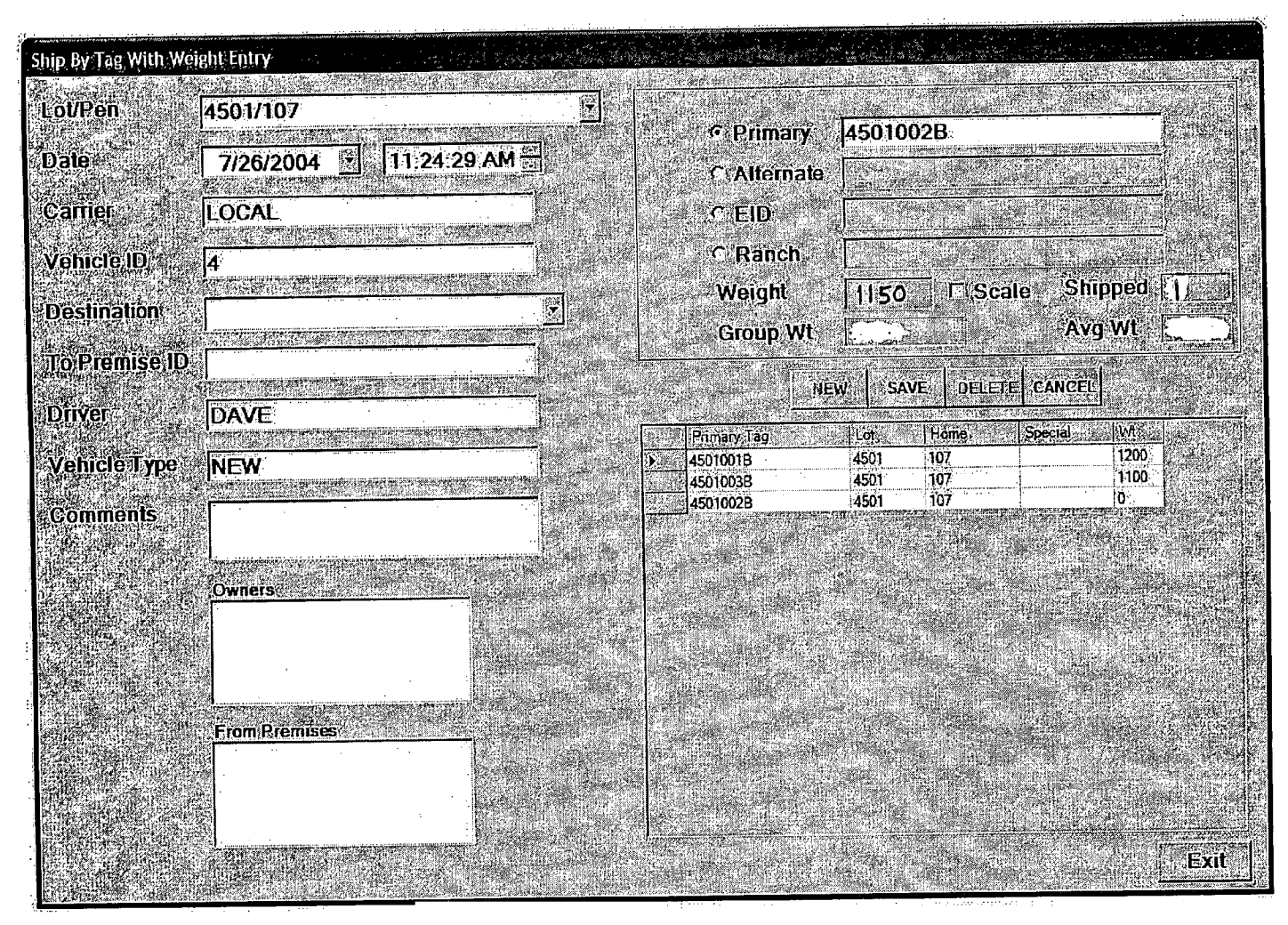

FIG. 49 is another user screen illustrating capability to record shipment by individual animal as opposed to recording shipment of a group of animals found within a designated lot or pen. More specifically, FIG. 49 indicates that one particular animal is to be recorded as shipped from Lot 4501 Pen 107 on Jul. 26, 2004. The animal is identified by its primary tag number. Additionally, the weight of the animal is also shown upon shipping. In order to identify particular animals to be shipped, the operator would either manually enter the tag number on the screen or if the animal had an electronic tag, the animal would be "wanded" and the reading device would directly interface with the data processing system to enter the particular electronic tag number on the screen. The user would enter data which may include the carrier, vehicle ID, destination, and new premise ID to which the animal was being shipped. Accordingly, FIG. 41 illustrates that shipments can be recorded by selecting individual animals.

Figure 50:
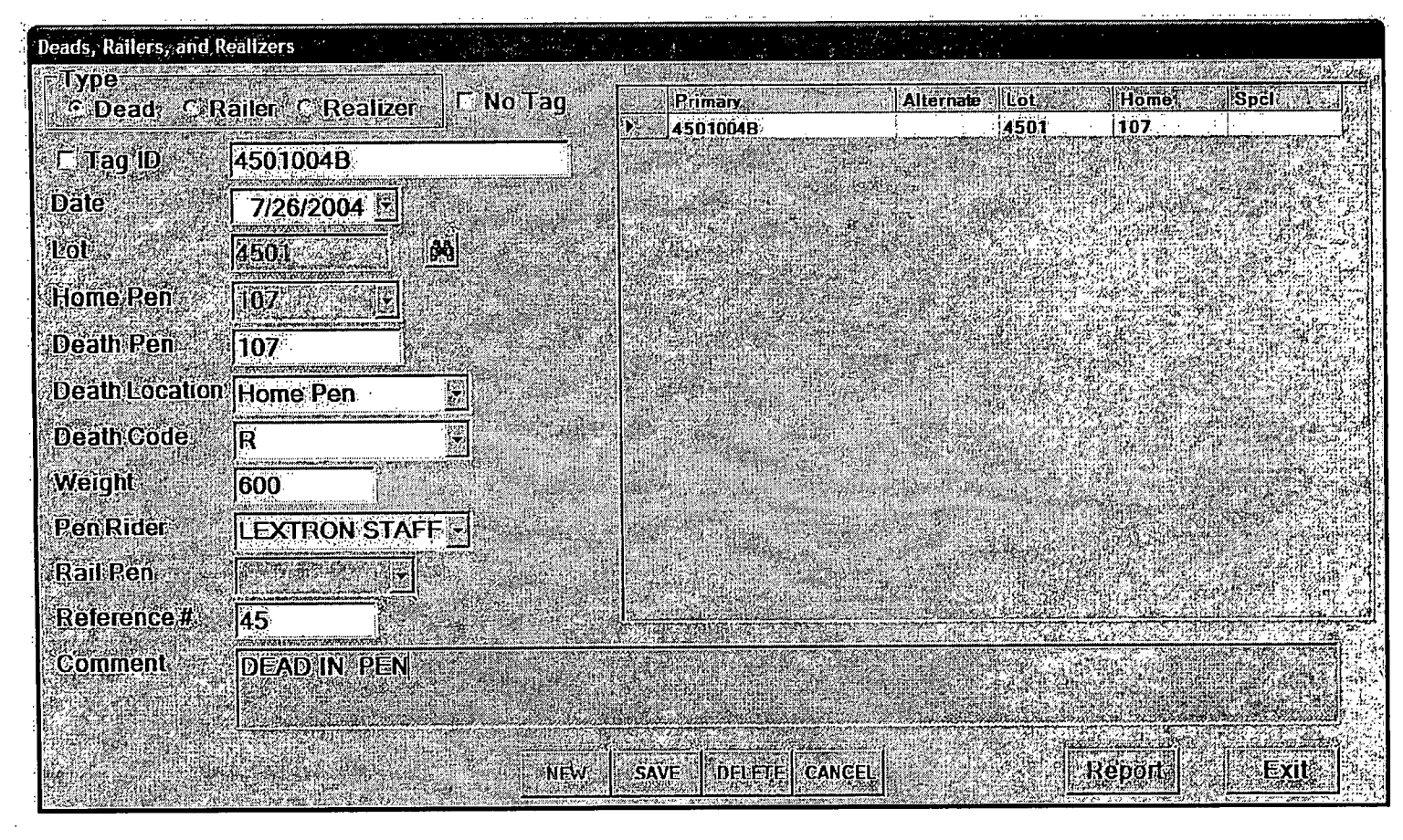

FIG. 50 is another user screen available for entering data regarding a change in status of a particular animal. During the production cycle of an animal, the animal can unexpectedly die. Thus, recordation must be made of the death. Accordingly, as shown in FIG. 502, the user would enter the tag, date of death, location of death, death code, and comments as necessary. Once this data has been entered, this particular animal could not be scheduled for any further processing or treatment as a live animal. A "Railer" status indicates that a decision has been made to no longer maintain an animal in the feedlot any longer, with the intent to soon ship the animal away from the feedlot. For example, an animal may not be responding to treatment and the cost to conduct further treatment exceeds the market value of the animal. Therefore, by designating the animal as a "Railer", the animal will not be further scheduled for treatment. The "Realizer" status indicates that a decision has also been made to ship an animal for one or more reasons, and the specific reason being recorded on another data entry screen for the particular animal. Thus, FIG. 50 represents the ability for a user to individually select animals and to change their recorded status as necessary.

Figure 51:
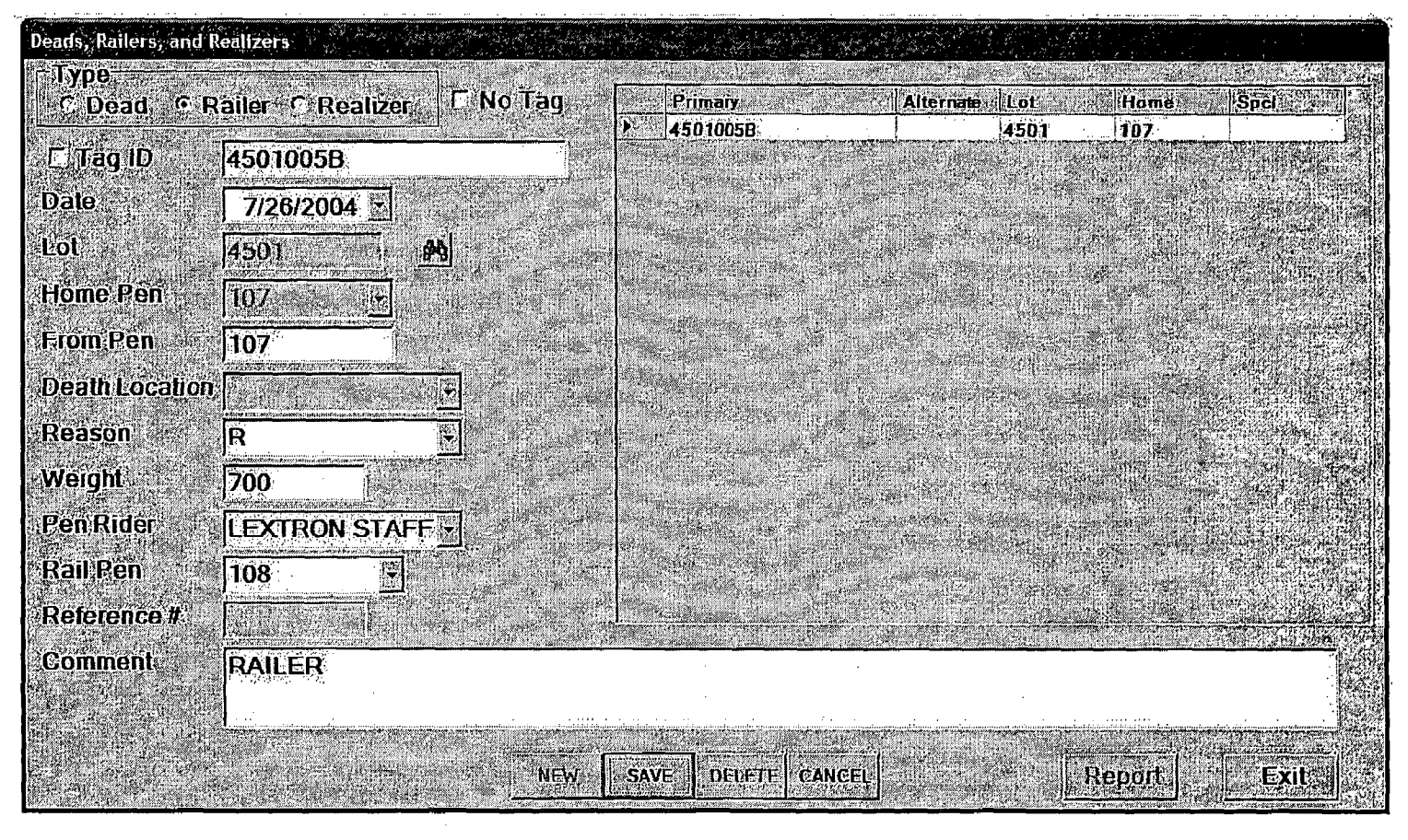

FIG. 51 is another user screen showing an example of an animal that has been designated as a Railer.

Figure 52:
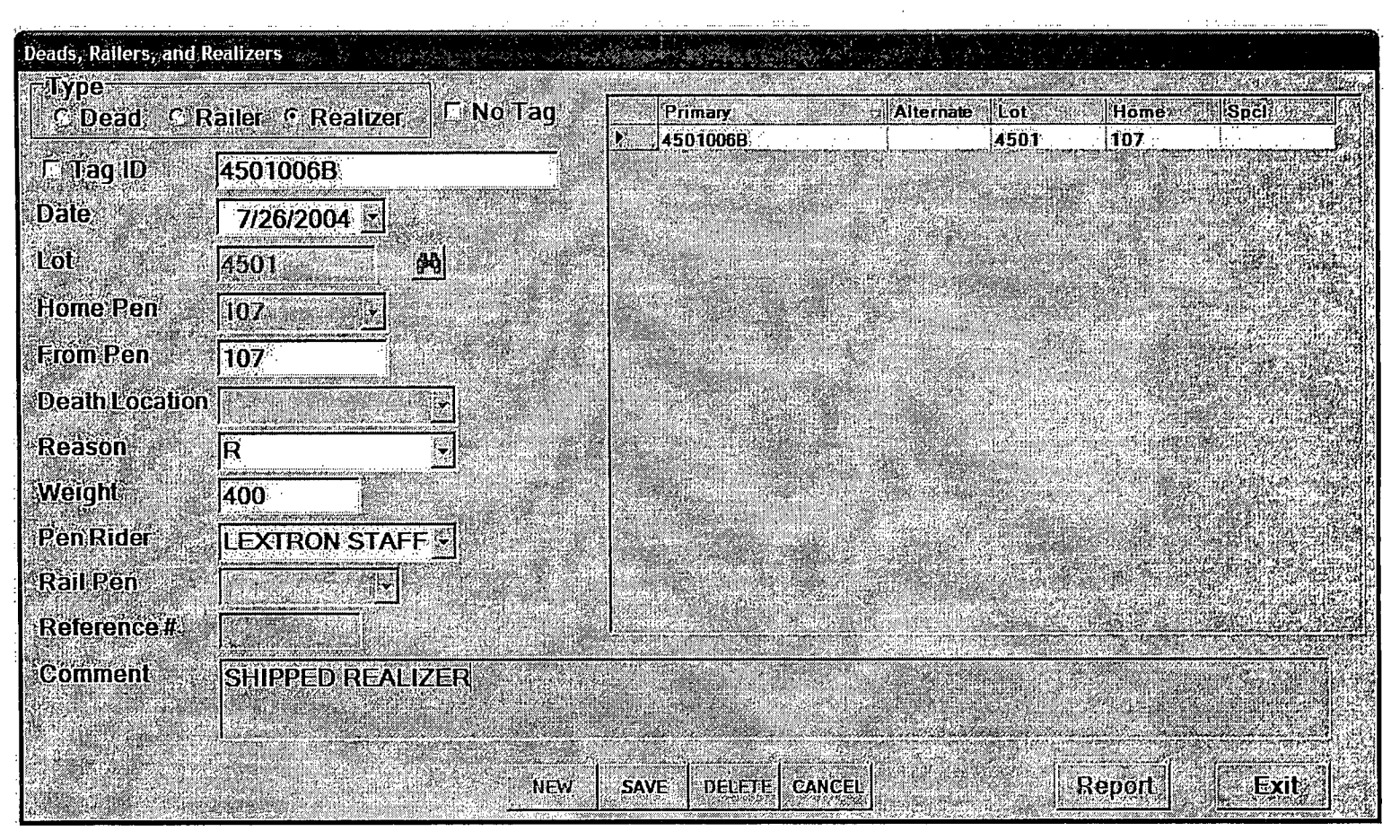

FIG. 52 is another user screen illustrating an example of an animal that has been designated as a Realizer.

Figure 53:
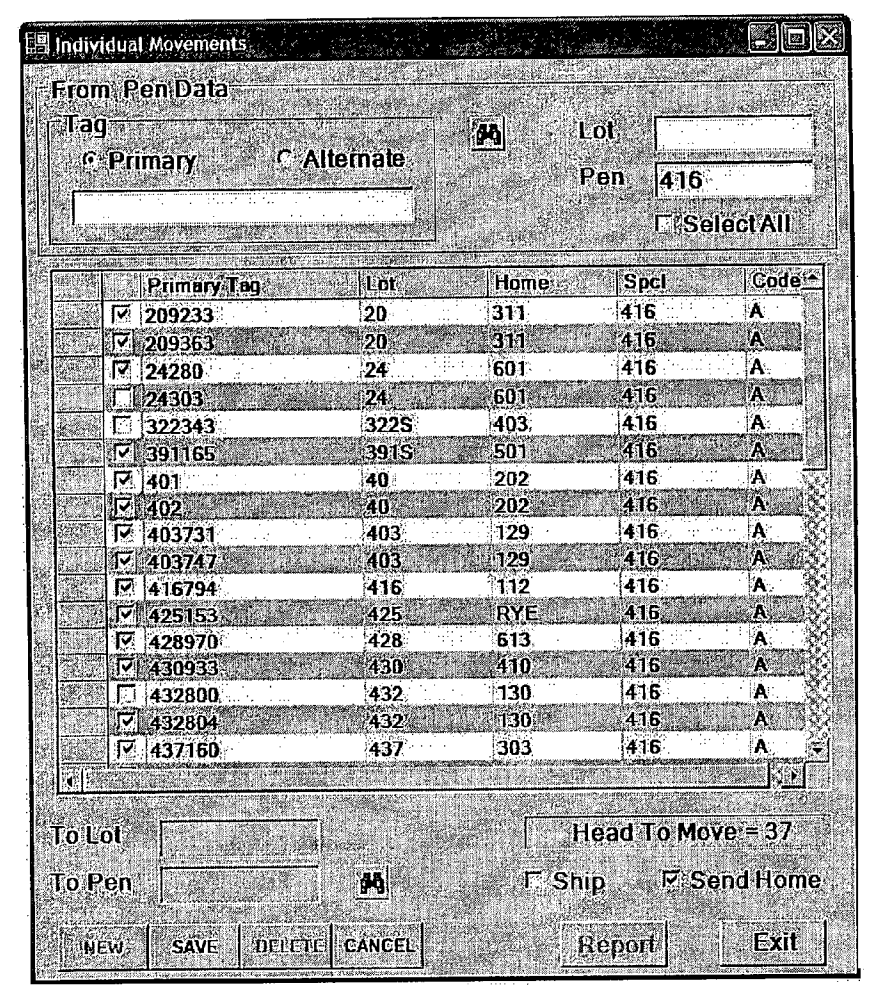

FIG. 53 illustrates a data entry screen that allows individual selection of animals to be recorded as being moved from one location to another. More specifically, the user can select a particular pen or lot, and each of the animals within the pen or lot at that time would be shown by tag number. The user then checks on the particular animal(s) to be recorded as moved, and then enters the pen/lot number where the animals are to be moved. In the example of FIG. 53, Pen 416 was selected as the "from" location, and all of the animals within Pen 416 are listed by their primary tag numbers. Thirty-seven cattle have been selected for movement to Pen 450. Once the user clicks on the Save button, the transfer will be recorded and the selected animals will be shown as being found within Pen 450.

Figure 54:
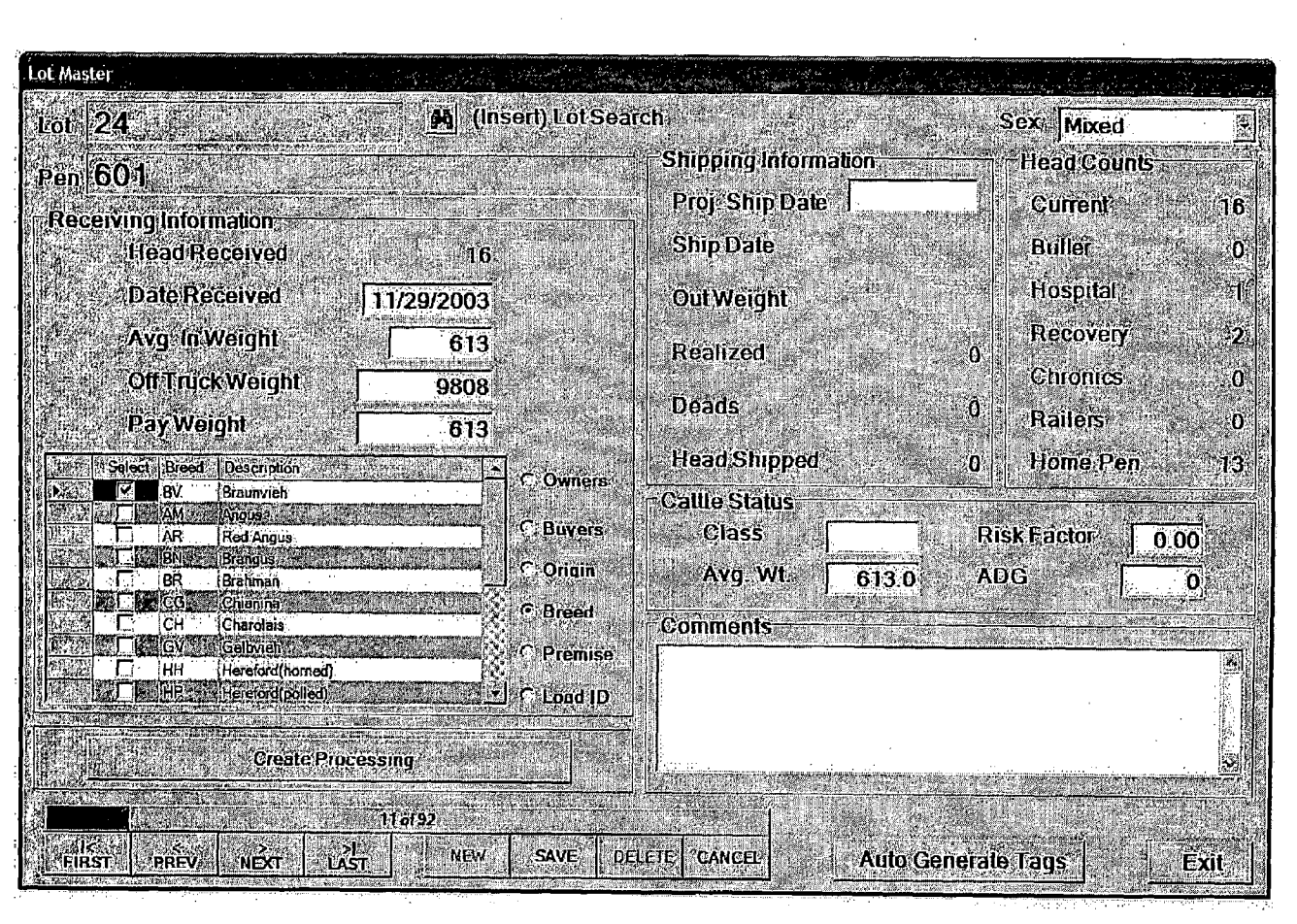

FIG. 54 is an informational screen that may be provided to a user regarding information where animals can be found at any particular time. In the example of FIG. 54, Lot 24, Pen 601 is selected. The screen indicates that there are 16 cattle that were received into this lot on Nov. 29, 2003. This screen also provides shipping information, head counts, cattle status, and comments. The user is not capable of changing head counts within this screen, but is able to add additional identifying information for the particular lot and pen such as the types of breeds, owners, buyers, etc. FIG. 54 more specifically shows that the user has selected to further identify animals within the particular lot by breed.

Figure 55:
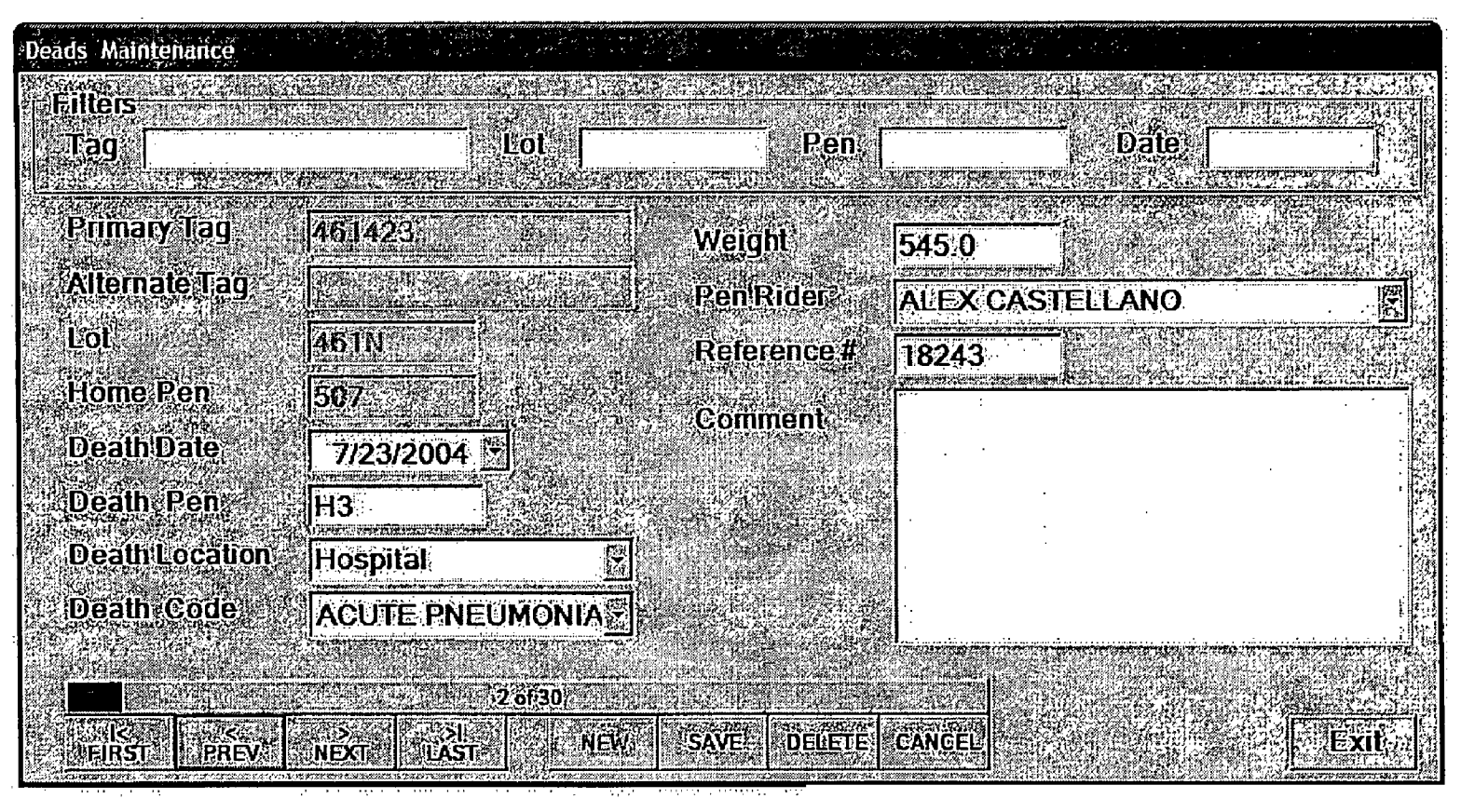

FIG. 55 is a data entry screen that allows the user to modify existing data regarding a dead animal. This type of data entry screen can generally be referred to as a maintenance screen.

Figure 56:
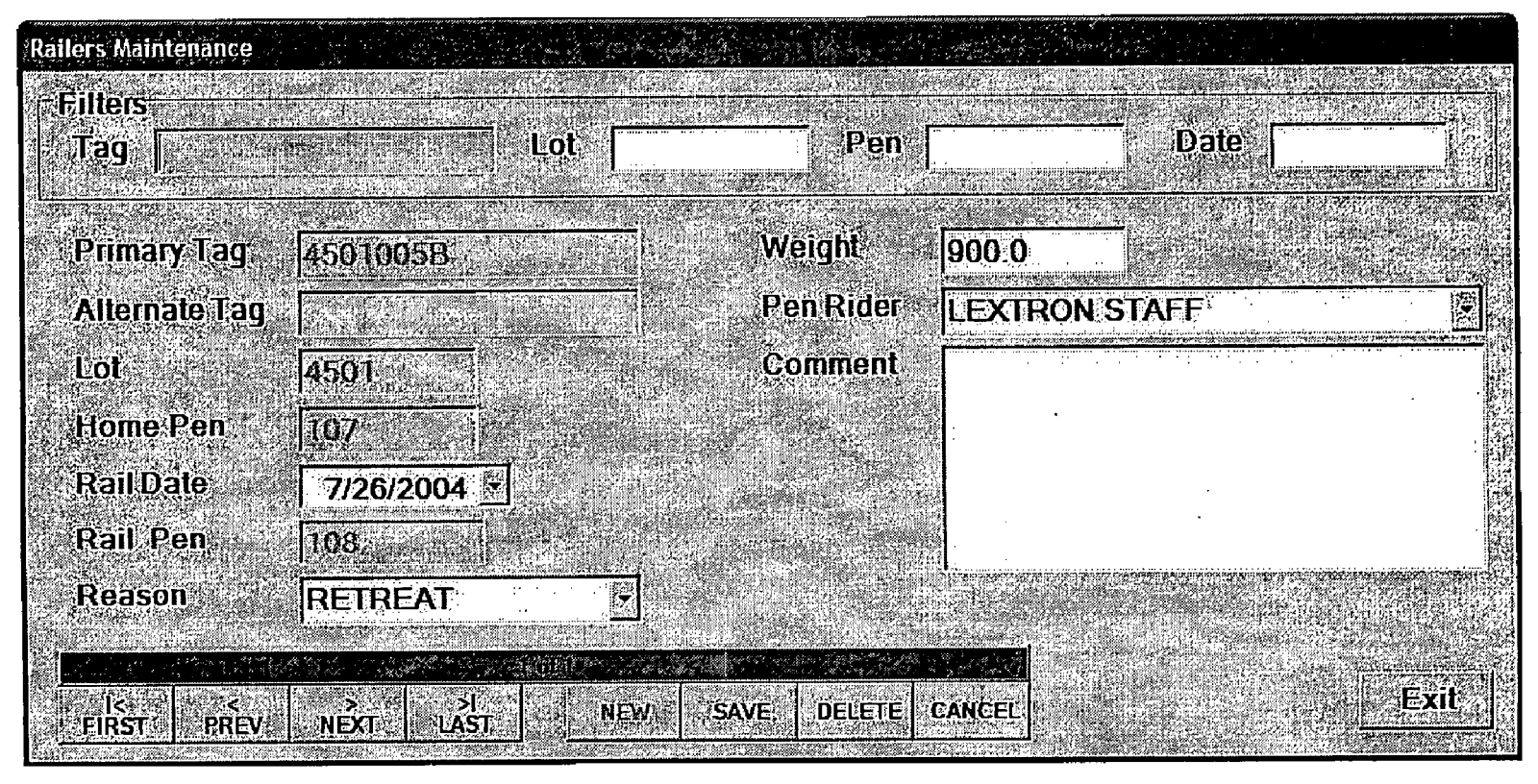

FIG. 56 is an example of a user screen allowing maintenance of a Railer record.

Figure 57:
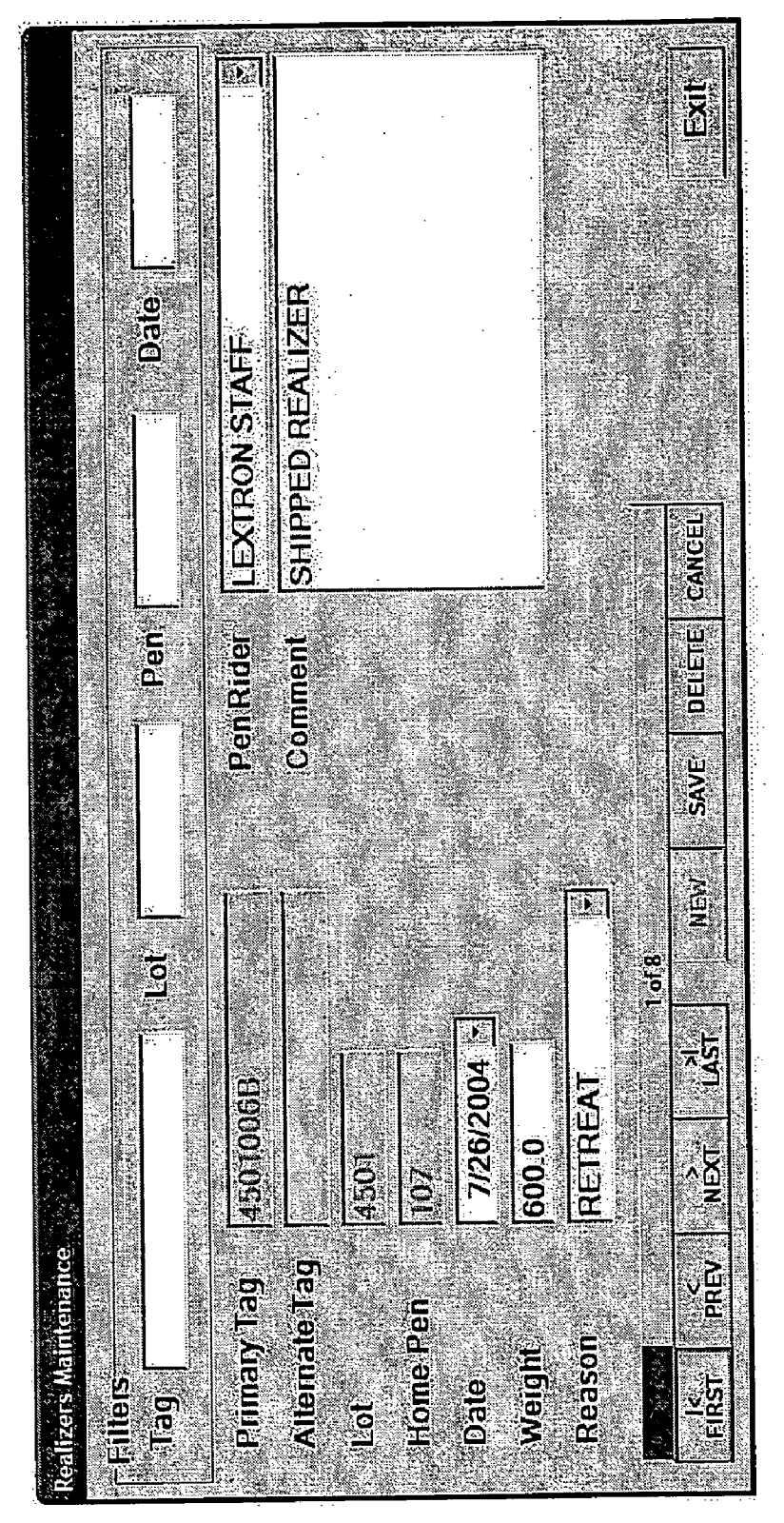

FIG. 57 is an example of a user screen allowing maintenance of a Realizer record.

Figure 58:
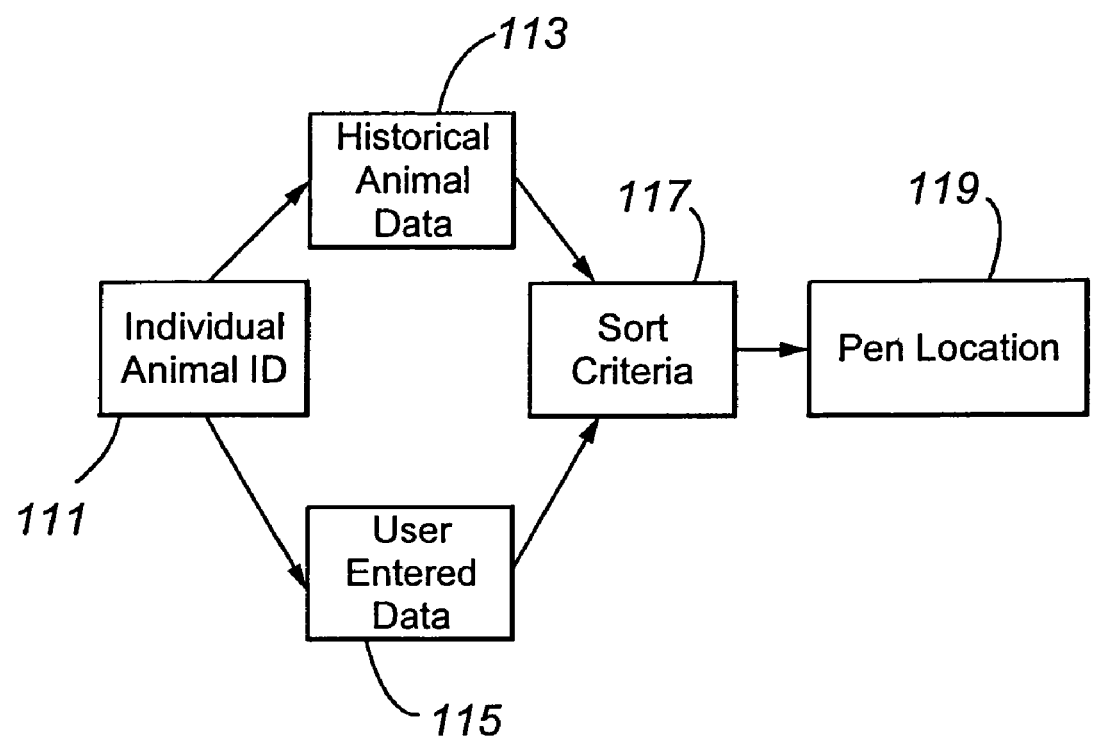
FIG. 58 is a schematic diagram illustrating an automated sorting criteria process of the present invention.

An additional function covered under the animal inventory sub-module includes animal sorting. Animal sorting refers to the continual evaluation of a single animal or a group of animals, and sorting those animals periodically so that animals with similar characteristics are grouped together in order to ease overall management tasks. For example, one or more animals in a particular feed yard may not be responding to particular medications administered to return the animals to proper health. Because these animals may continue to carry an infection, they might infect other cattle within the pen or lot; therefore, it is desirable to isolate those animals from the others to prevent the spread of disease. Further for example, if there are one or more cattle who do not appropriately respond to the feed ration in order to gain a prescribed amount of weight, then those particular animals should also be segregated and treated separately, thereby simplifying the feed call for other animals who are properly responding to routine feed rations. Referring now to FIG. 58, a simplified schematic diagram is provided to explain the automated sorting criteria process of the present invention. As shown in Block 111, first the individual animal ID is entered in a treatment screen via manual entry or through automated entry for example, an EID tag reader. Once this information is entered, the system then locates all animal data associated with the individual animal ID from the animal management database. This historical animal data is shown at Block 113. The user may then enter additional animal data, shown at block 115, to further describe the present state of the animal. For example, the animal could be weighed at that time. Based upon the recorded data concerning the particular animal, application of one or more rules/algorithms to the sort criteria 117 results in a recommended location for the animal by comparing the animal data to the sort criteria. The recommended location is typically another pen and lot location 119. The user can then initiate transfer of the animal to the recommended pen/lot location. Additionally, it shall be understood that while a particular location may be recommended by the sort criteria, the user also has the ability to manually select a particular location thus overriding the recommended location.

Figure 59:
FIG. 59 is a user screen showing the manner in which cattle can be sorted wherein individual animal data appears on the user screen once an animal's tag is read, the screen further illustrating where the animal originates from and the location to where the animal is being transferred to in the sort operation.

Referring to FIG. 59, another user interface screen is provided to explain in greater detail the manner in which cattle can be sorted thereby allowing the user to assign a particular animal to a new group of animals within a facility. When it is desired to conduct a sorting operation, the user first obtains information on the particular pens that are to be sorted, which may include a new load of cattle that are being held in a receiving pen. In the example of FIG. 59, the user has chosen to sort two numbered pens and one receiving pen. More specifically, the upper portion of the user interface screen includes two small boxes containing information on cattle in two different pens of the feedlot, shown as boxes 270 and 272. The information displayed for these two pens includes the head count of the cattle present in the pen, the head count of the cattle not in the pen (for example cattle in a hospital pen), and a tag count. The tag count corresponds to the number of animals in the head count that have a tag that identifies the particular animals. In some cases, an animal may be received into a pen without a tag thereby accounting for the difference between the head count and the tag count. The animals to be sorted from the receiving pen are displayed in box 274 which provides a file location, identification of the premise/location where the animal has been received from such as from another feed yard (the "from premise"), and a count of the cattle in the receiving pen (the "record count"). The file location is the temporary location in the central database where information is stored about the group of received cattle. Next, the user will approach a particular pen and begin the sorting process. An animal is removed from the pen and guided through a chute or alley to identify the animal being processed. As discussed above, tag reading can be done automatically by a tag reader incorporated within the chute/alley, or alternatively by a hand-held tag reader, or the tag information can be manually entered. As the animal tag is read, the recorded animal data appears on the user screen. In the example of FIG. 59, the tag ID, alternate tag ID, ranch tag, weight and temperature of the animal is displayed in box 276. Box 278 illustrates additional animal detail such as the sex, origin and owner of the animal, and box 280 shows details of which particular drugs the animal is to receive. The user has also selected various sort criteria for sorting the selected pen/file locations. In the example of FIG. 59, the sort criteria chosen includes sort criteria for weight and breed. It shall be understood that any number of sort criteria can be chosen by the user depending upon the purpose of the sorting operation at that time, and the sort criteria available within the system. The location to which the animals are to be transferred to are illustrated at the lower portion of the screen. Three pens are identified as the locations to which the cattle are to be transferred to, and the information for these pens are shown in boxes 282. These pens are designated as the "to pens". The information for these to pens include the designated pen and lot numbers, as well as the current head count in the pens, the head count not in the pens (for example, cattle in a hospital pen), the tag count, and the average weight of the animals in the pens. After the user views the animal information in boxes 276, 278, and 280, the user can decide to sort the particular animal into the designated pen by clicking on the post processing button 284. Optionally, during set up of the sort operation, the user can choose to have all records automatically posted once each tag is read so that each animal record automatically posts to the proper pen location. The animal is sorted into the appropriate pen based upon the match of the animal data with the sorting criteria. As each animal is processed, a head count processed is provided in box 286 that provides a running total of animals processed versus the total number of animals to be processed. The total number of animals processed is a sum of the "from pen" and "from files" selected. Additionally, as each animal is processed, the head count in the losing or from pen will be decreased by one, and the gaining or to pen count will be increased by one. Thus, the user can also view the progress of the sorting operation as each animal is processed. Of course, as the location of each animal changes by moving the animal from one pen to another, the individual animal information is also updated to reflect the location of where the animal currently is. However, data is also maintained as to the animal's previous pen location, as necessary. Maintaining this historical location data will ensure that an animal can be traced back to the original receiving group of cattle for various evaluation purposes. The sorting screen in FIG. 59 can be accessed during processing or receiving functions within the data processing system. Additionally, a user may wish to change the sort criteria during the sort operation based upon the actual results of the sort operation. Accordingly, the user can click on either the change sort criteria button 283 or the view sort criteria button 285 to choose another criteria in the listing of available sort criteria, or to modify the chosen criteria.

D. File Maintenance Sub-Module

The file maintenance sub-module of the present data processing system refers to the sub-module that allows a user to add, delete, and modify items on the data verification tables, and operational parameter tables set up in the system. Many of these tables are preloaded/preconfigured with standard values and may be supplemented or modified by authorized users.

In order to ensure data integrity of the system, the verification tables and operational parameter tables are incorporated to ensure that any data entered can be validated against acceptable data values and parameters. For example, if a user manually enters a tag number and the tag number does not correspond to an available active record, then the attempt to make that data entry would result in the production of an error message to the user indicating that the tag number is not valid.

Additionally, the present system has the ability to set general rules and parameters for processing, treating and treatment of animals. For example, specific criteria may be set for both feeding and/or treatment protocols thus potentially avoiding improper feeding or treatment in terms of excessive use of supplies for an animal making it an unprofitable investment. More specifically, a particular mathematical relationship or algorithm can be defined to control available feeding or treatment protocols. The variables in the algorithms can be selected from data fields that can be especially configured.

Figure 60:
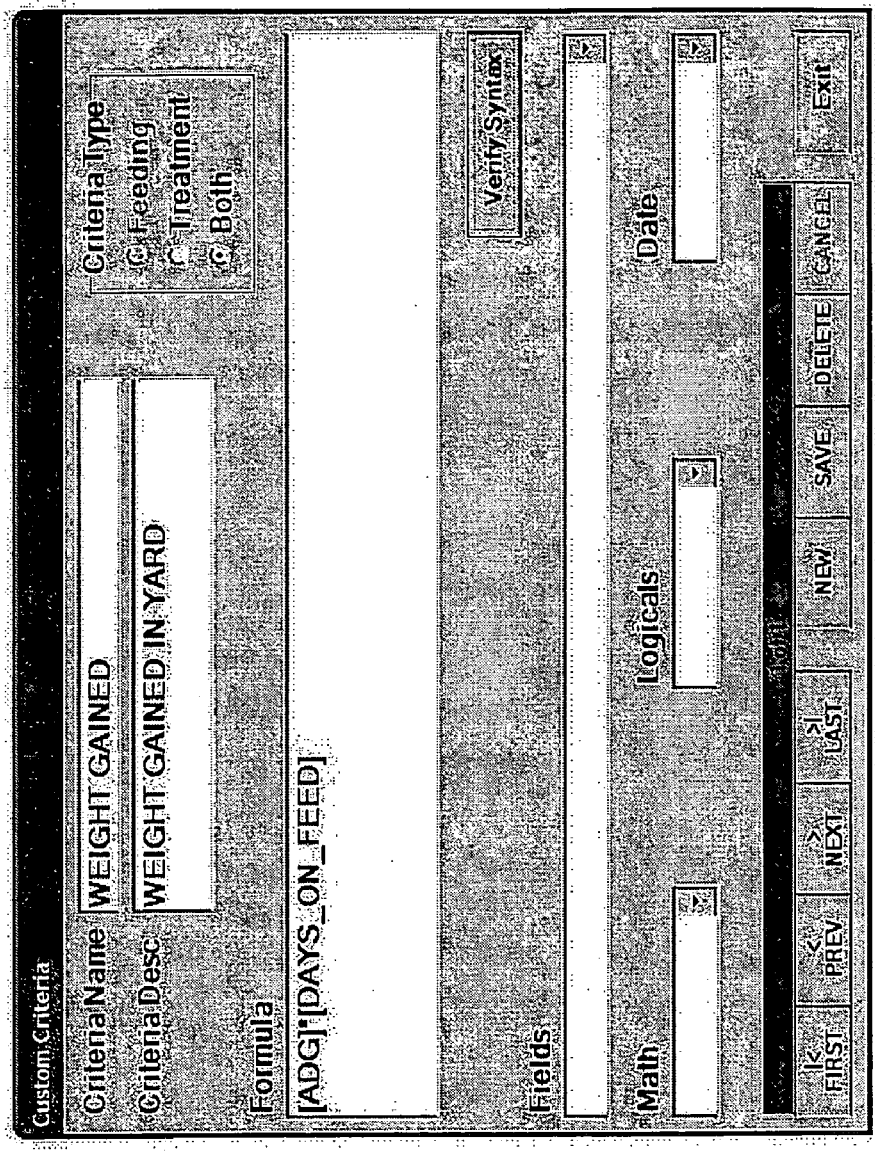
FIG. 60 is a user screen illustrating yet another example of a custom criteria that has been developed for both feeding and treatment criteria.

Referring now to FIG. 60, another example is shown for creating custom criteria. More specifically, FIG. 60 shows that the user decided to create both a feeding and treatment criteria given a criteria name of "Weight Gained". The criteria corresponds to the amount of weight gained by the animal while in the particular feedlot/yard. The amount of weight gained in the yard is calculated by a formula. In this case, the formula is ADG multiplied by the number of days on feed. ADG and days on feed are specific data fields that are recorded for each animal. Therefore, FIG. 60 simply represents another example of the ability to create criteria by naming particular criteria, and then assigning some type of mathematical relationship to that criteria. In another user screen, the "Weight Gained" criteria could be presented as a view option, and selecting this option would allow the user to view weight gain information for the animal to date.

FIG. 61 illustrates an example of a listing of diagnosis codes that correspond to a particular ailment or condition. The codes can be modified by a user, and diagnosis codes can be arranged or separated by facility as required. These diagnosis codes can then be used to build specific treatment protocols based on the diagnosis entered by the user.

Figure 62:
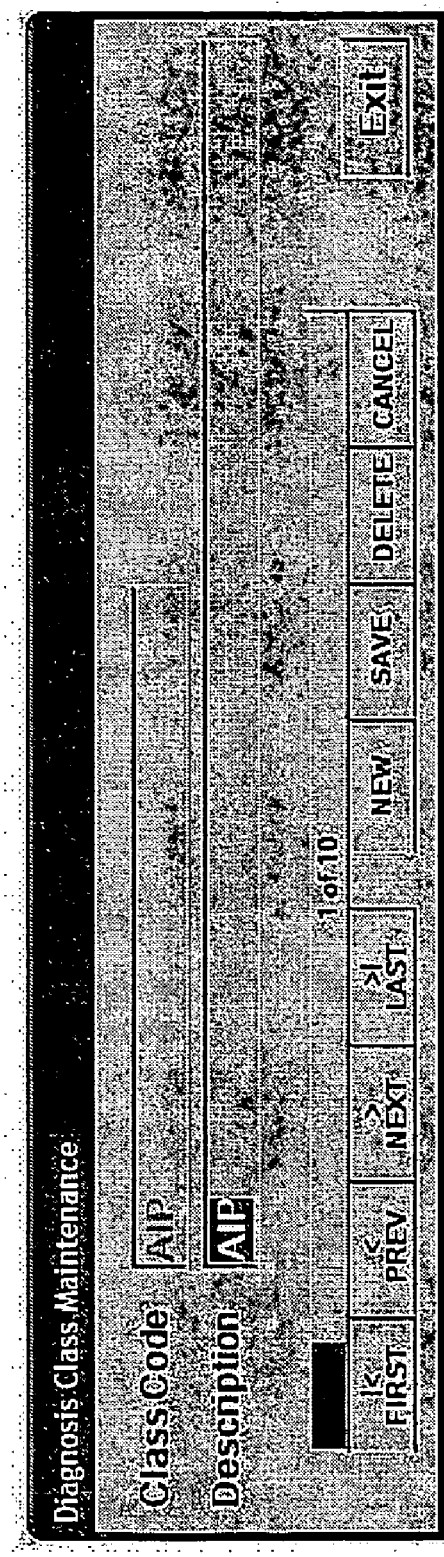
FIG. 62 illustrates a user screen for management of like groupings of criteria used across many different facilities to accommodate comparison and analysis of the facilities.

FIG. 62 illustrates a user screen for management of like groupings of criteria used across many different facilities to accommodate comparison and analysis of the facilities, even though each uses different particular criteria names. For example, FIG. 62 would allow a financial institution to analyze different feedlots by assigning a class diagnosis or "super-classification" to each of the different named criteria that may exist at the different facility locations. More specifically, one feedlot may code respiratory diseases as RSP, R, or P. Another feedlot may choose to designate respiratory diseases as corresponding to some other criteria code. This screen allows a user to identify each of the different facility criteria that correspond to a general classification or condition so that when information is gathered from the various facilities, like data is categorized for each facility thus allowing for companion and analysis.

Figure 63:
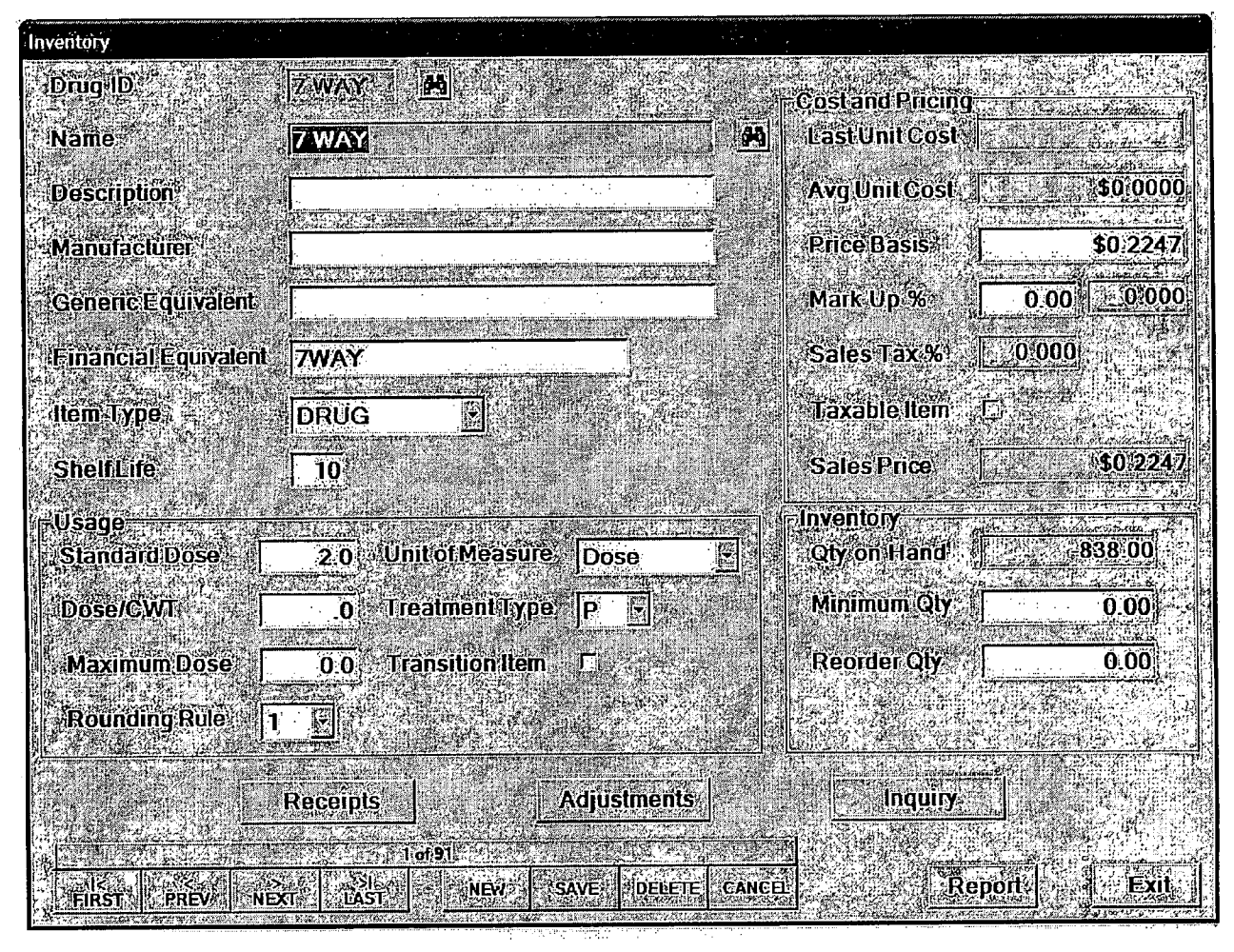

FIG. 63 illustrates a screen allowing a user to view inventory such as drugs, and allowing the user to change certain information on the drug such as the name, manufacturer or standard dosage.

Figure 64:
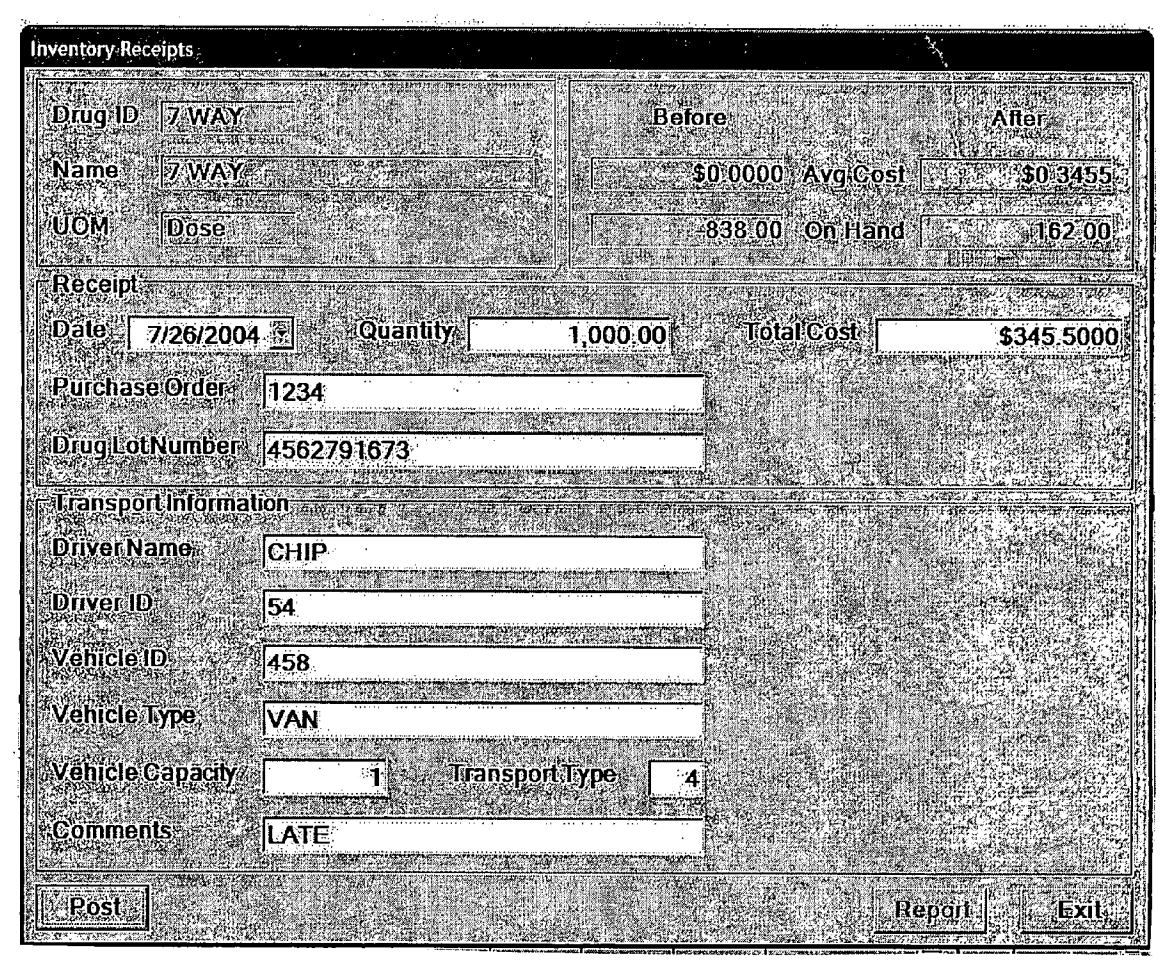

FIG. 64 illustrates a user screen that allows a user to record inventory being received. As supplies arrive, such as drugs, the user would enter the arrival of the drugs into the inventory by completing the information on the screen. Once quantity and cost data is entered, the actual inventory is automatically adjusted to show a "Before" and "After" state for the particular drug. Drugs are entered on a drug by drug basis; therefore, if a particular facility received a number of different drugs on a particular day, the user would separately enter the receipt of each drug by completing an inventory receipt screen for each.

Figure 65:
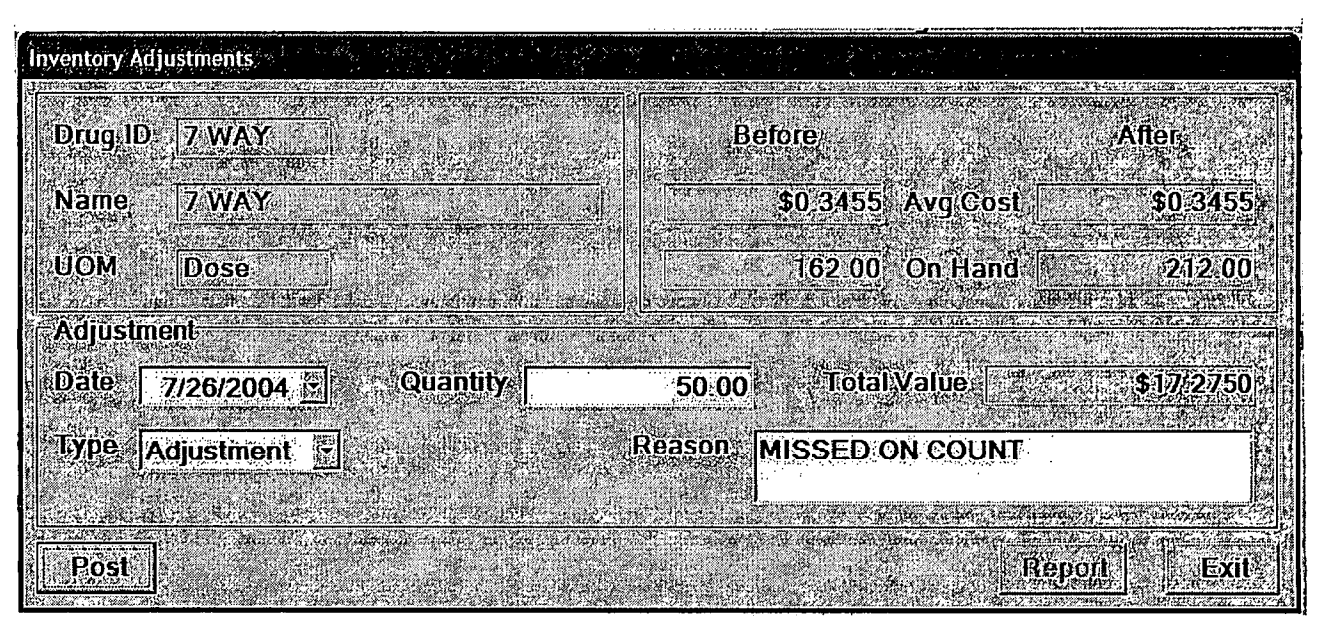

FIG. 65 illustrates a user screen allowing adjustments to inventory. For example, if a particular drug remains in inventory beyond expiration, or a drug is inadvertently lost or destroyed, then the screen at FIG. 65 allows user to adjust the inventory. In the specific example of FIG. 65, the reason for the adjustment was to correct an initial miscount of a particular drug when it was recorded as being received in inventory. Clicking on the "Adjustments" button from FIG. 63 brings up the inventory adjustments screen of FIG. 65.

FIG. 66 is an inventory inquiry screen allowing the user to check the inventory for a particular drug. Clicking on the "Inquiry" button from the screen in FIG. 63 brings up the inventory inquiry screen of FIG. 66. The user simply enters in the drug name, or drug ID and the on-hand amount is then shown.

Figure 67:
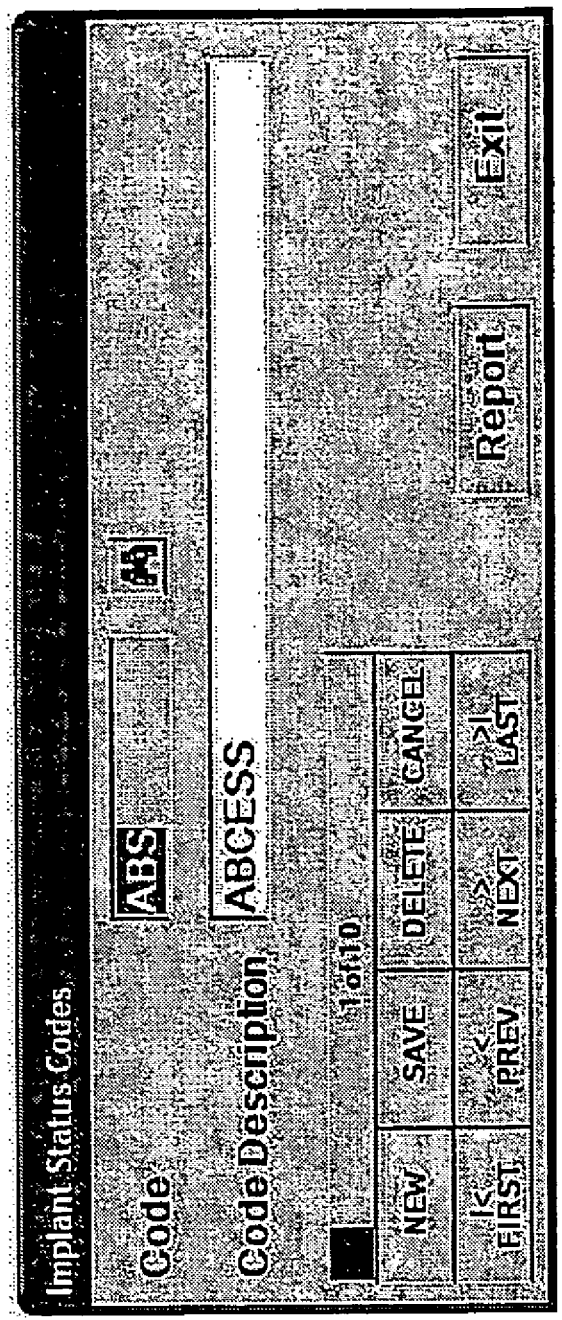
FIG. 67 is a user screen illustrating an implant status code that provides a preset listing of those implants installed for animal identification purposes.

FIG. 67 is an implant status code screen that provides a preset listing of implant status codes. The preset code listing can be modified as desired. An implant refers to a device implanted within the animal, such as an RFID tag, and it may be desirable to list the particular status of the implant during processing or treatment. In the example of FIG. 67, the code ABS indicates that an abscess has developed because of the implant, thus signaling some treatment should occur to heal the abscess.

Figure 68:
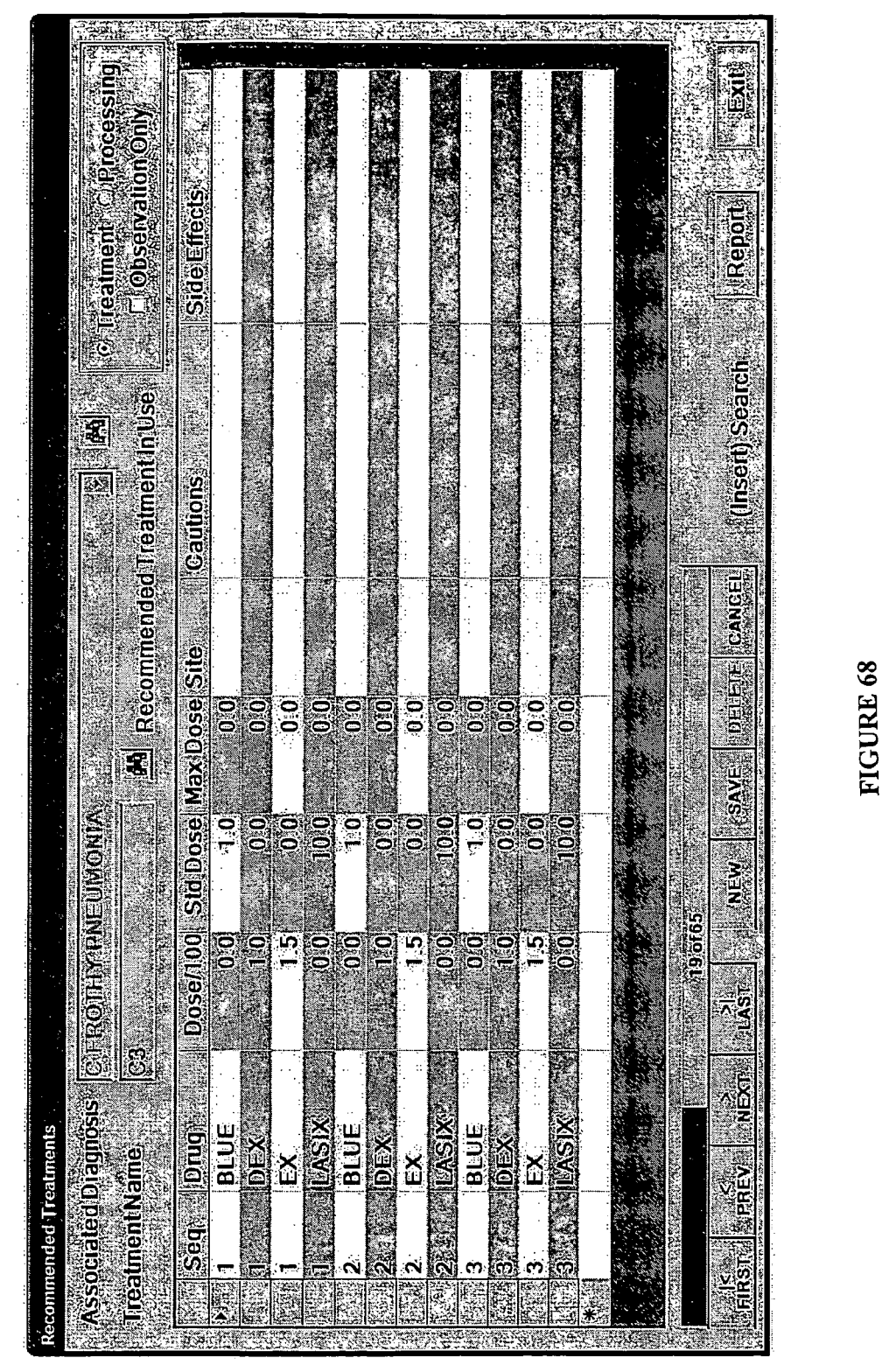

FIG. 68 illustrates a recommended treatment screen that allows a user to enter a particular treatment protocol for a specified diagnosis. As shown, the particular diagnosis provided is frothy pneumonia, and the user has built a treatment protocol by entering in the sequence and types of drugs to be administered. Accordingly, once a particular animal is given a diagnosis, the user can then find out the recommended treatment by entering the diagnosis code. It may be desirable to limit the ability of the user to create or change particular treatments based upon the corresponding diagnosis. For example, to prevent a potential drug overdose, an algorithm may be established in a parameter table which does not allow a user to enter an excess quantity of the particular drug. Thus, according to the screen shown in FIG. 68, a user would be unable to simply enter any type of treatment regimen without receiving an error message indicating that the proposed regimen was unacceptable with system parameters.

Figure 69:
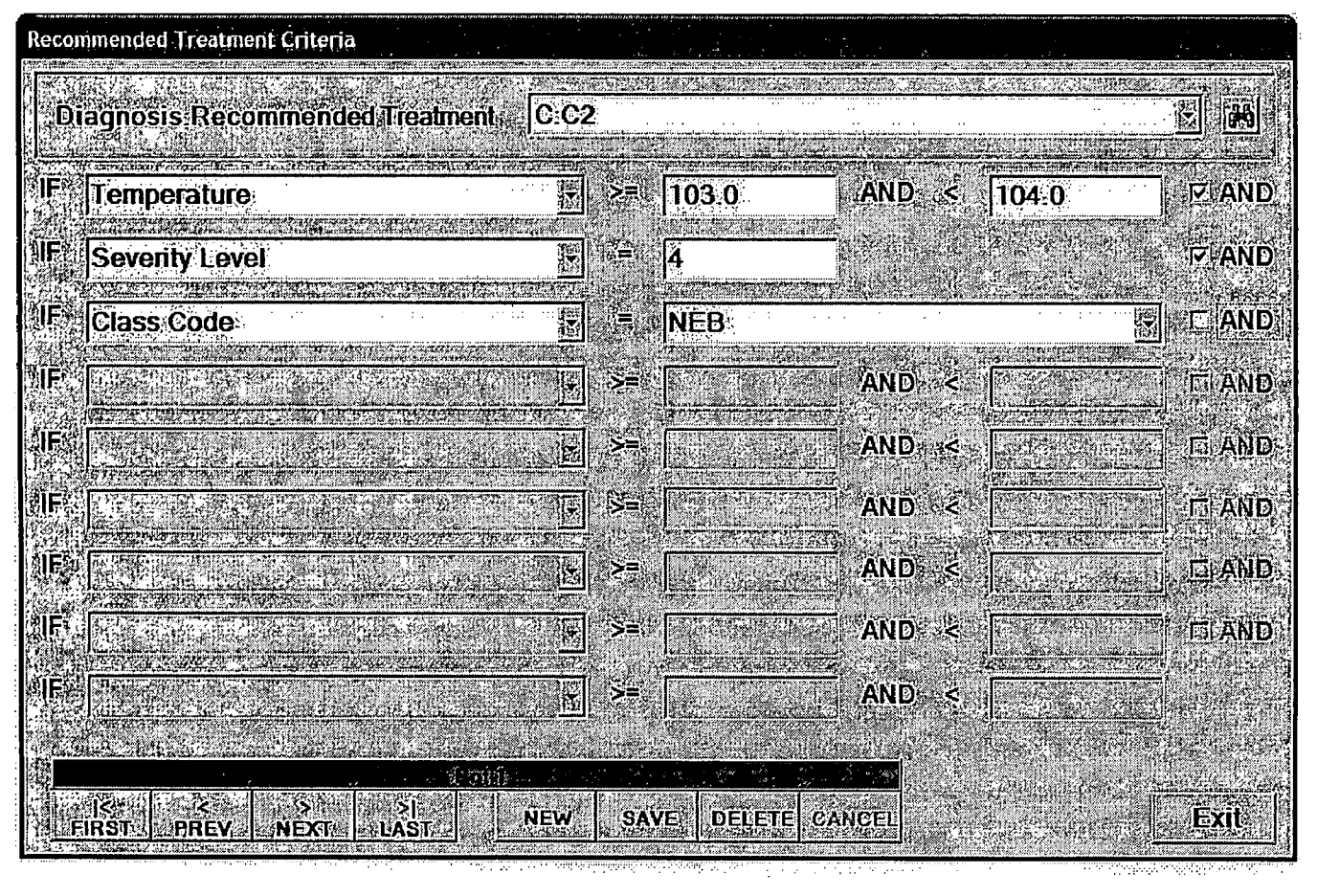

FIG. 69 is another user screen illustrating an example for creating recommended treatments based on selected criteria. In the example of FIG. 69, if the animal has a diagnosis "C", and the animal has the designated temperature range, has the indicated severity level, and has other observed criteria/symptoms, then the recommended treatment is "C2".

Figure 70:
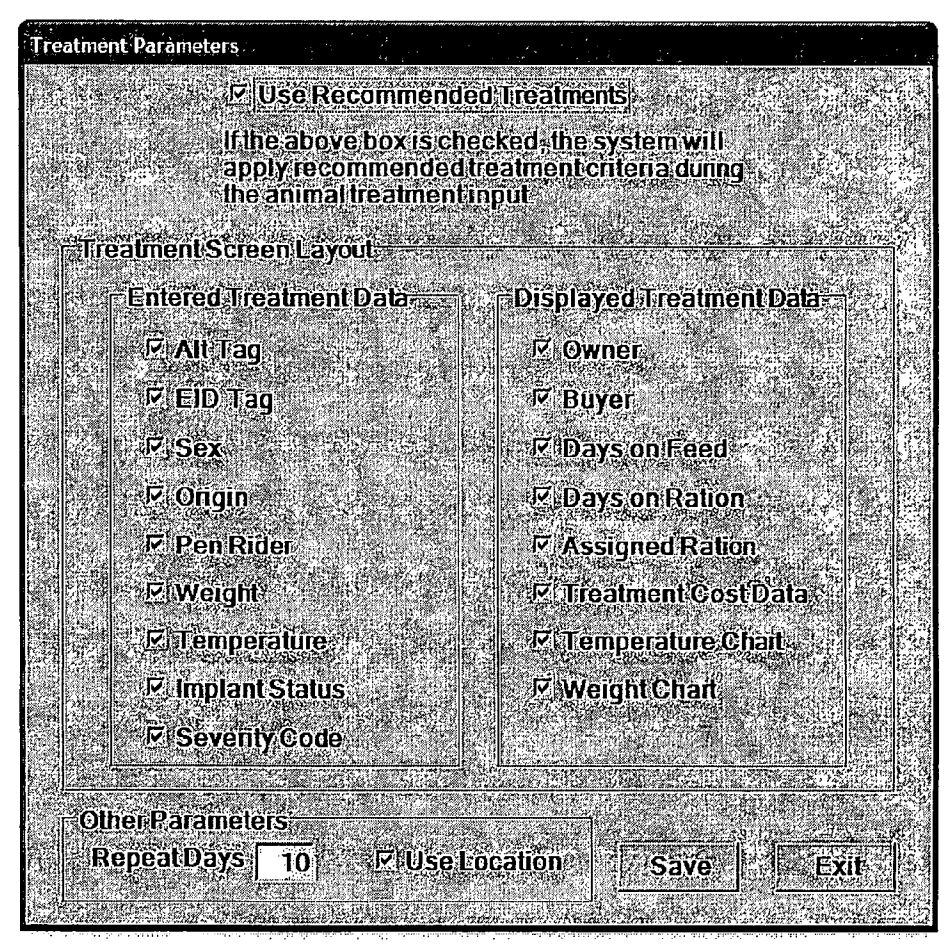

FIG. 70 is a screen allowing a user to view recommended treatments or to disable the display of recommended treatments during animal treatment input. This screen also allows a user to set up the screen layout for the treatment screen. As shown in FIG. 70, the user decided to adopt the recommended treatments by checking the box, and has also chosen to have the treatment screen show all available fields on both the entered treatment data as well as the displayed treatment data.

Figure 71:
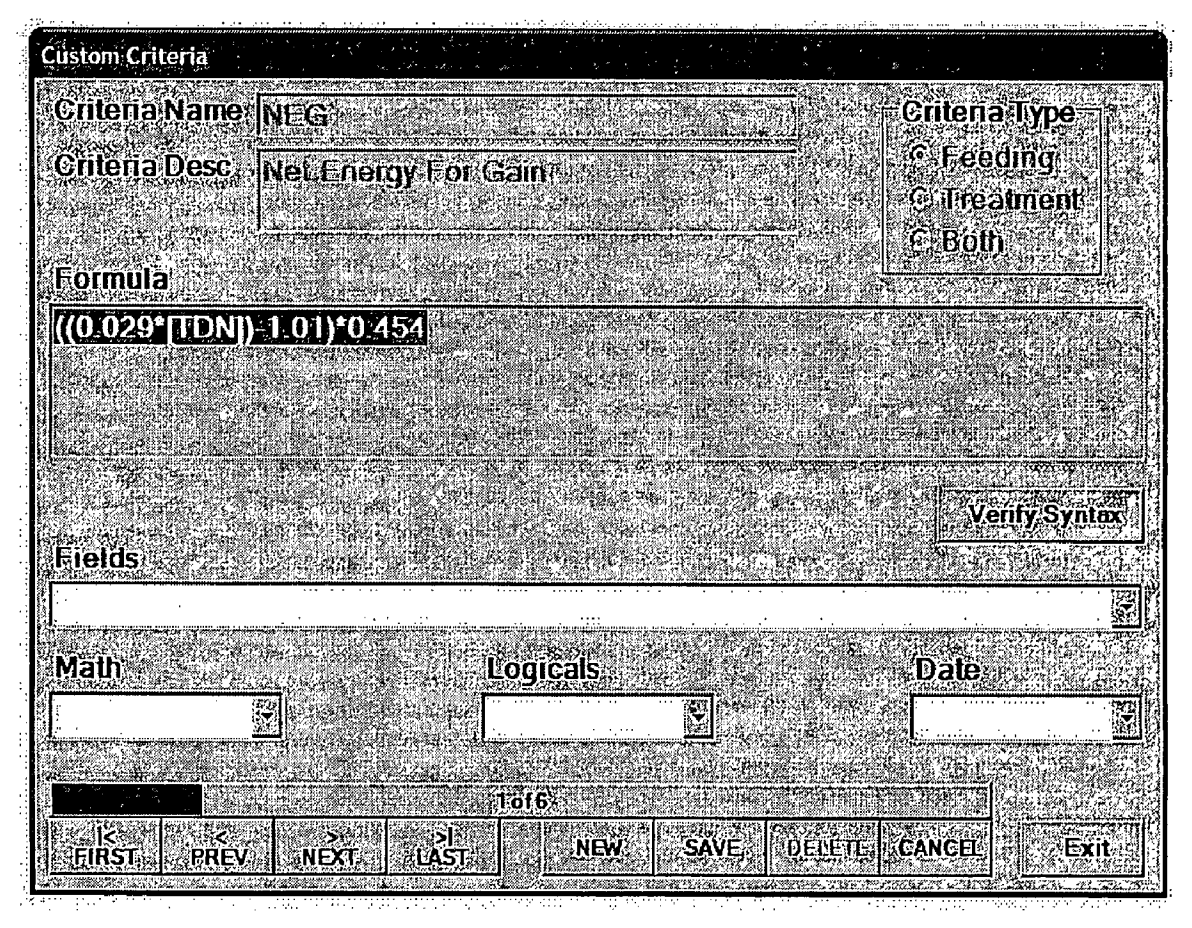

FIG. 71 is a user screen showing another example of data entry for establishing another custom criteria. In this particular figure, the user is developing a feeding criteria described as "Net Energy For Gain", and designated by the criteria name NEG. A formula is established to calculate the criteria, including the variable TDN that corresponds to a designated data field.

Figure 72:
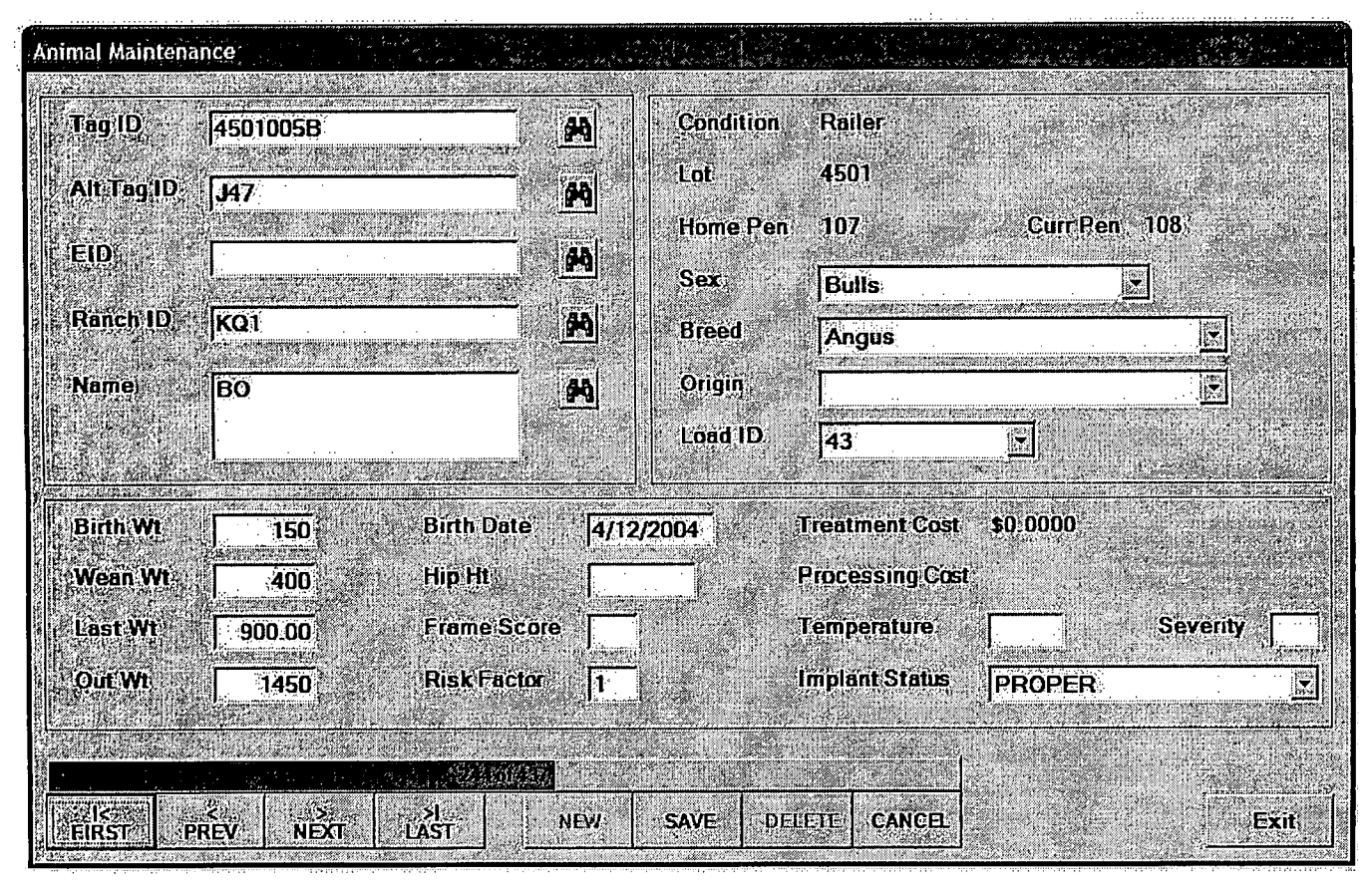

FIG. 72 is a user screen for animal maintenance allowing the user to input data regarding modifications to any of the individual status fields for a particular animal to include tag information and animal condition. For example, it may be necessary to correct data that was initially mis-entered. Any of the open fields shown in the figure can be modified as necessary. Of course, only selected system users would be given the authority to change such data.

Figure 73:
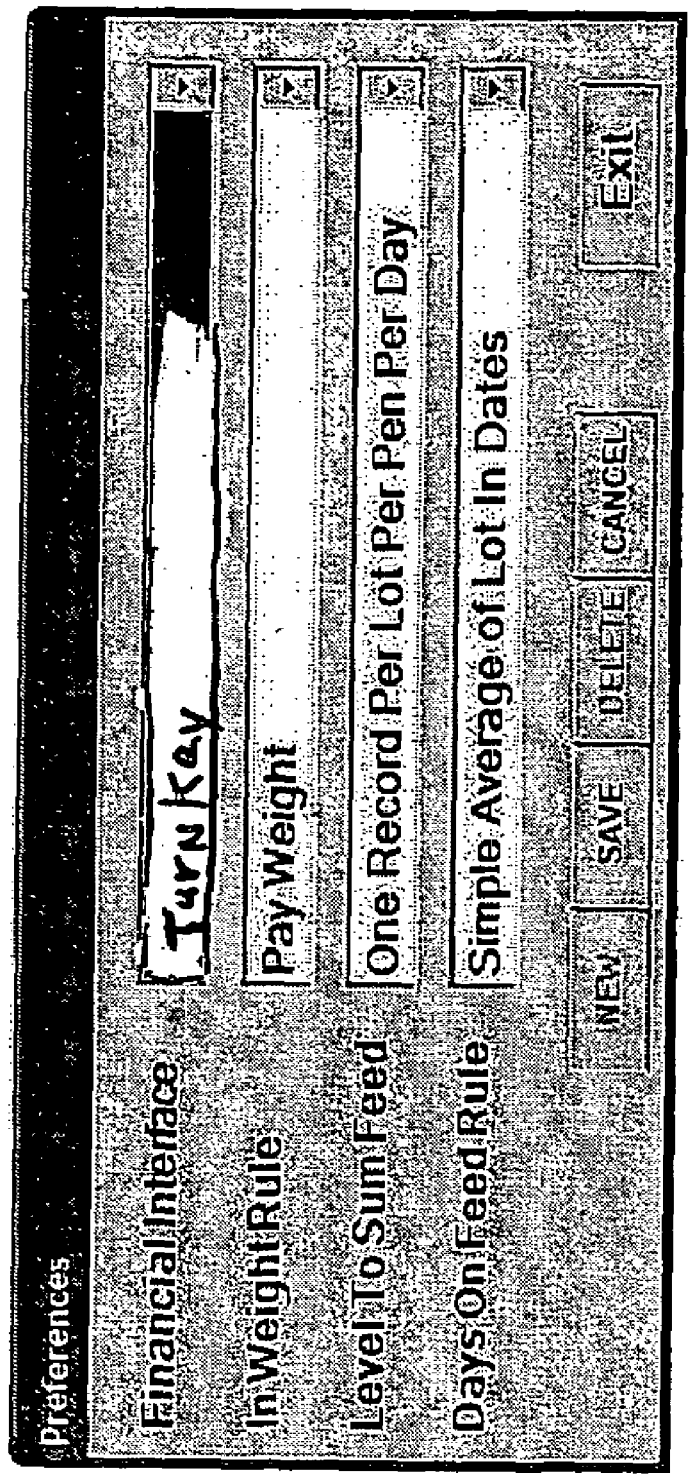
FIG. 73 is a user screen for setting preferences as to how data should be configured for transmission to another entity.

FIG. 73 is a user screen allowing one to set preferences as to how data should be configured for transmission to a financial institution, or for receiving information back from a financial institution. Thus, the screen shown in FIG. 73 allows the user to select how data is exchanged to best interface with other data processing systems. In the example of FIG. 73, the financial interface is with a system called TurnKey. The reporting weight of a particular animal will be by pay weight, the sum feed is based upon one record per lot per pen per day, and the days on feed rule is the simple average of lot in dates.

Figure 74:
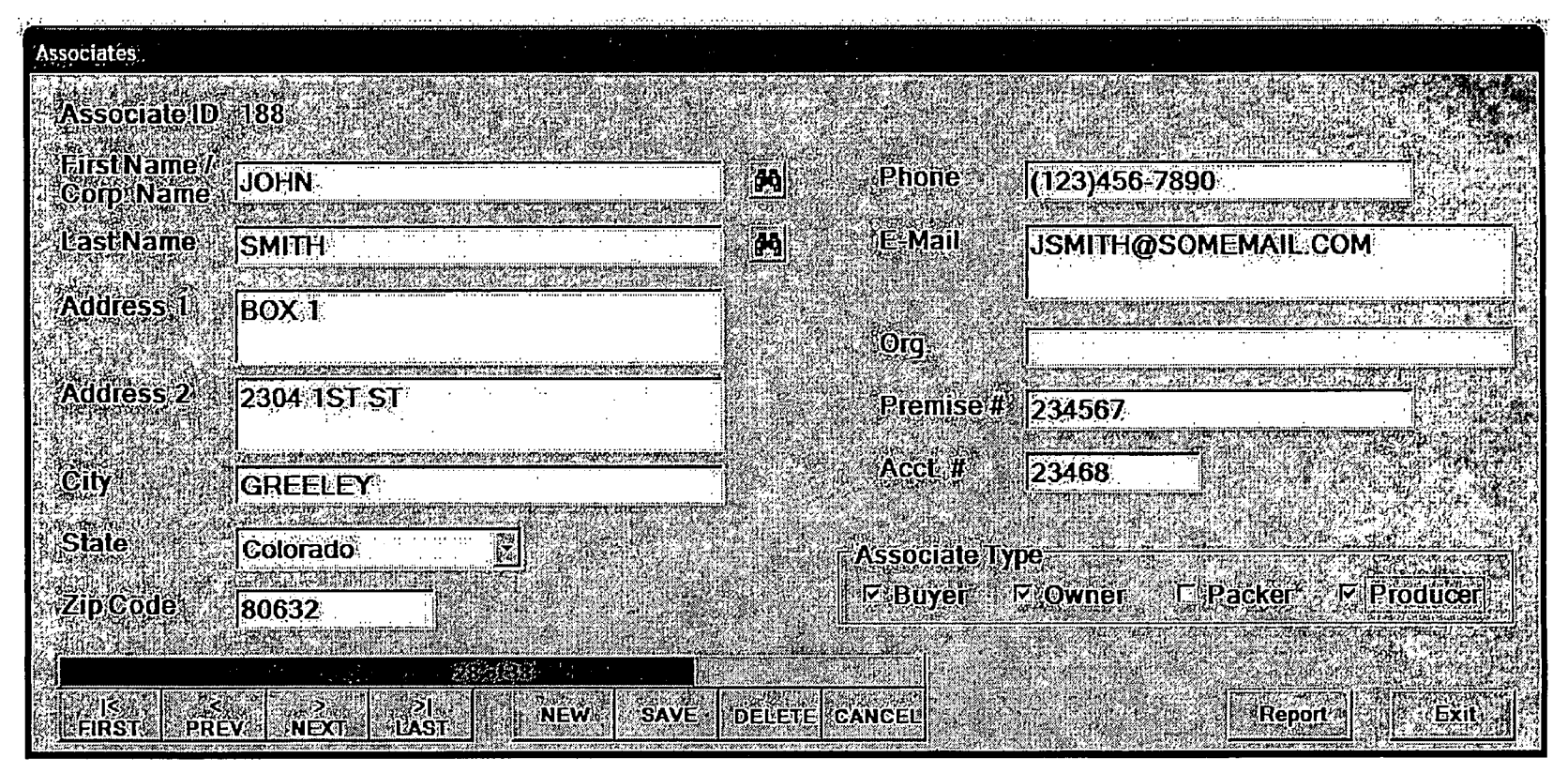

FIG. 74 is a data entry screen for identifying associates within the system. Associates can be defined as buyers, owners, packers, producers (ranchers), etc. Each associate within the system is provided an associate ID which ultimately can determine the degree to which each can access data in the system or modify system data. The Associate screen is periodically updated to identify all associates participating in the data processing system.

FIG. 75 is a data entry screen regarding breed codes that can be used within the data processing system. The user can select from the provided listing of breed codes, or may add additional breed codes as required. These breed codes can be used throughout the system to identify each animal entered into the system by breed.

Figure 76:
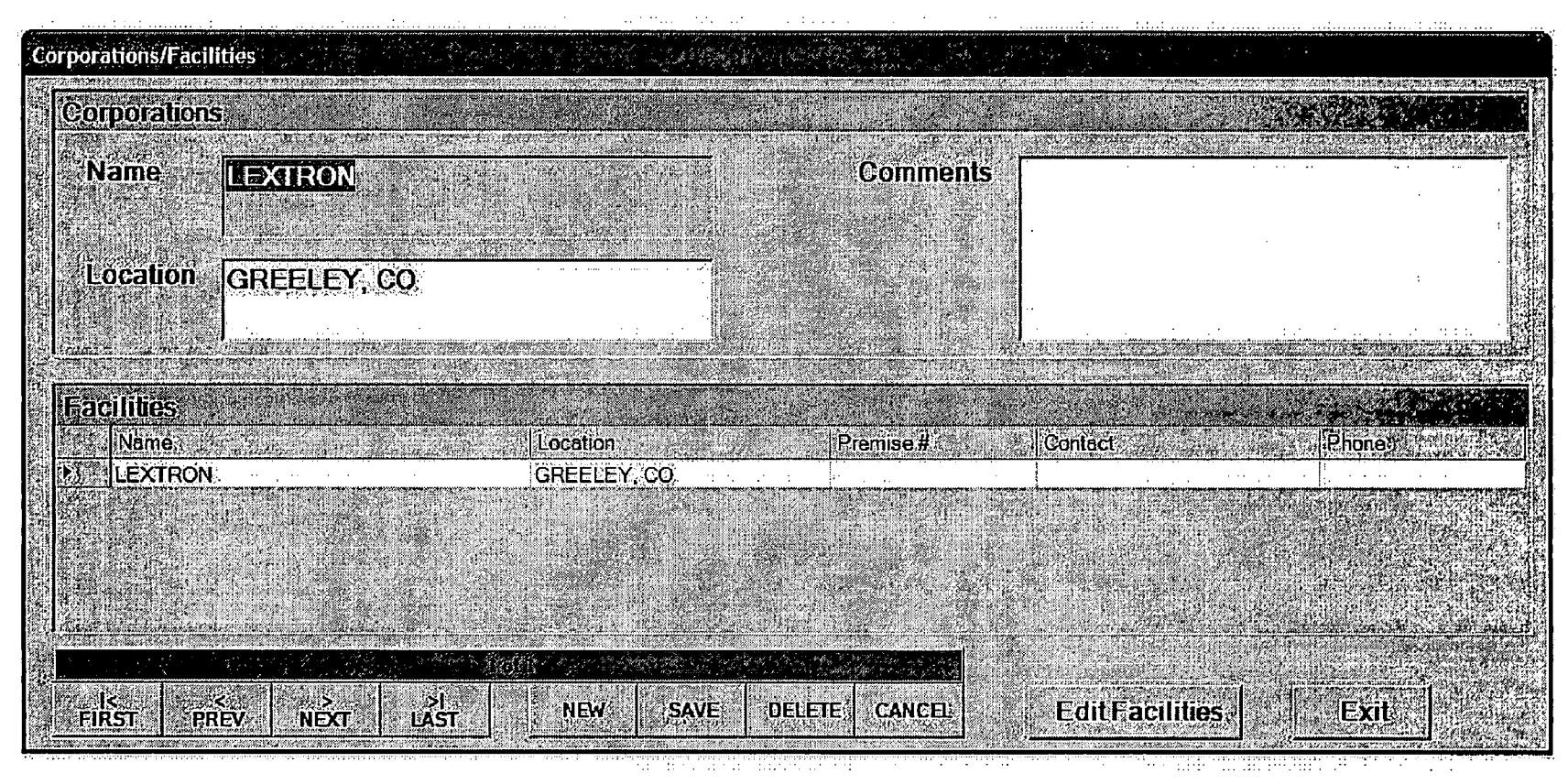

FIG. 76 is a data entry screen for setting up particular facilities within the system for determining what type of system access should be provided, what type of data should be made available to a particular facility, etc.

Figure 77:
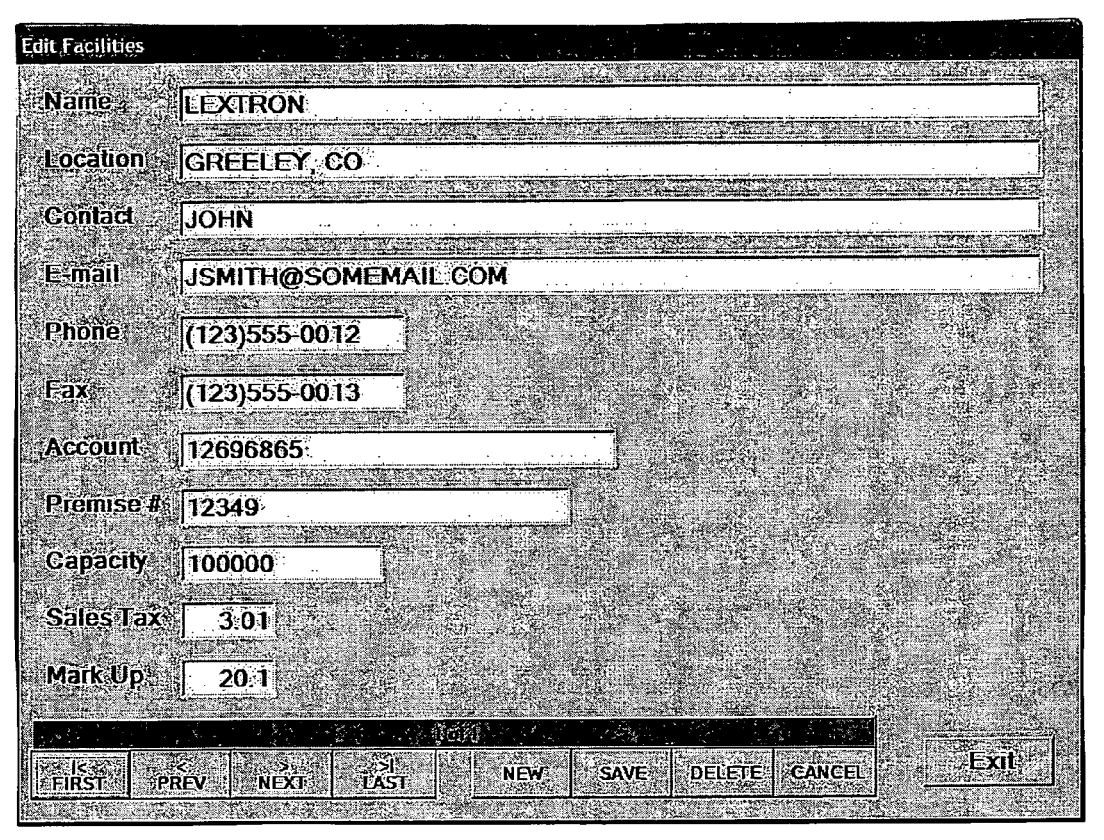

FIG. 77 is another data entry screen that allows one to edit specific data about each facility.

Figure 78:
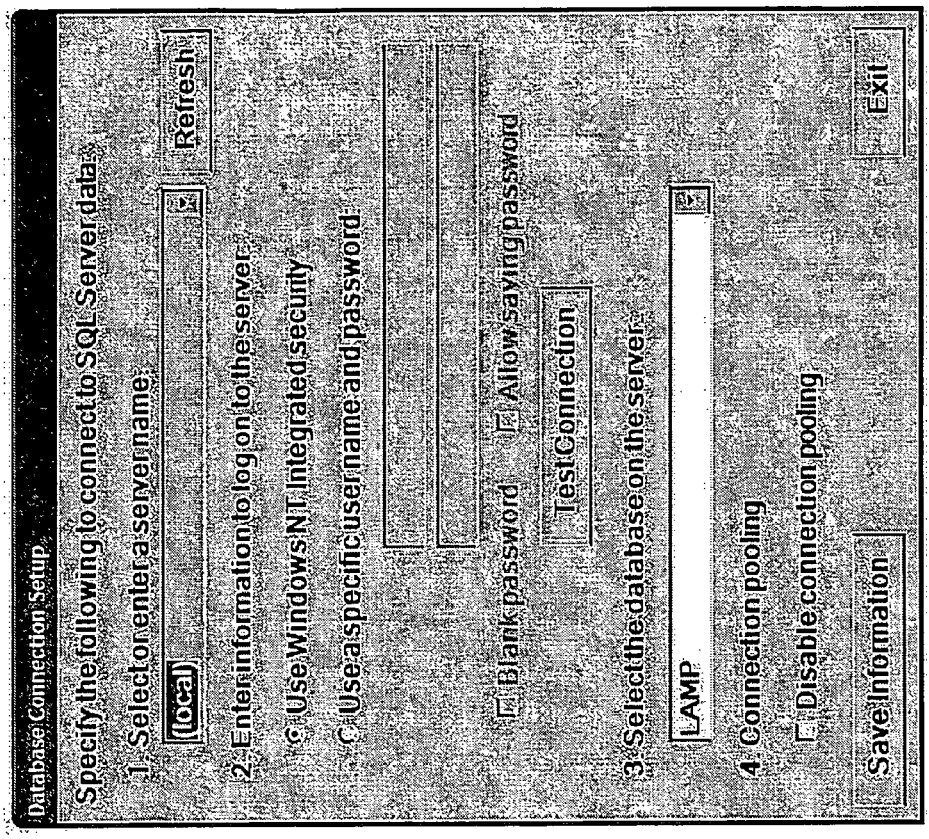
FIG. 78 is a user screen for configuring a desired type of connection to be set up between local or central database servers and a particular facility.

FIG. 78 is a configuration screen allowing the user to determine the necessary or desired type of connection set up between the local or central database servers and a particular facility. As shown in the figure, the user would enter the server name, the manner in which the user would log on to the server, select a particular database(s) on the server which the user wanted to access, and also determine connection pooling.

Figure 79:
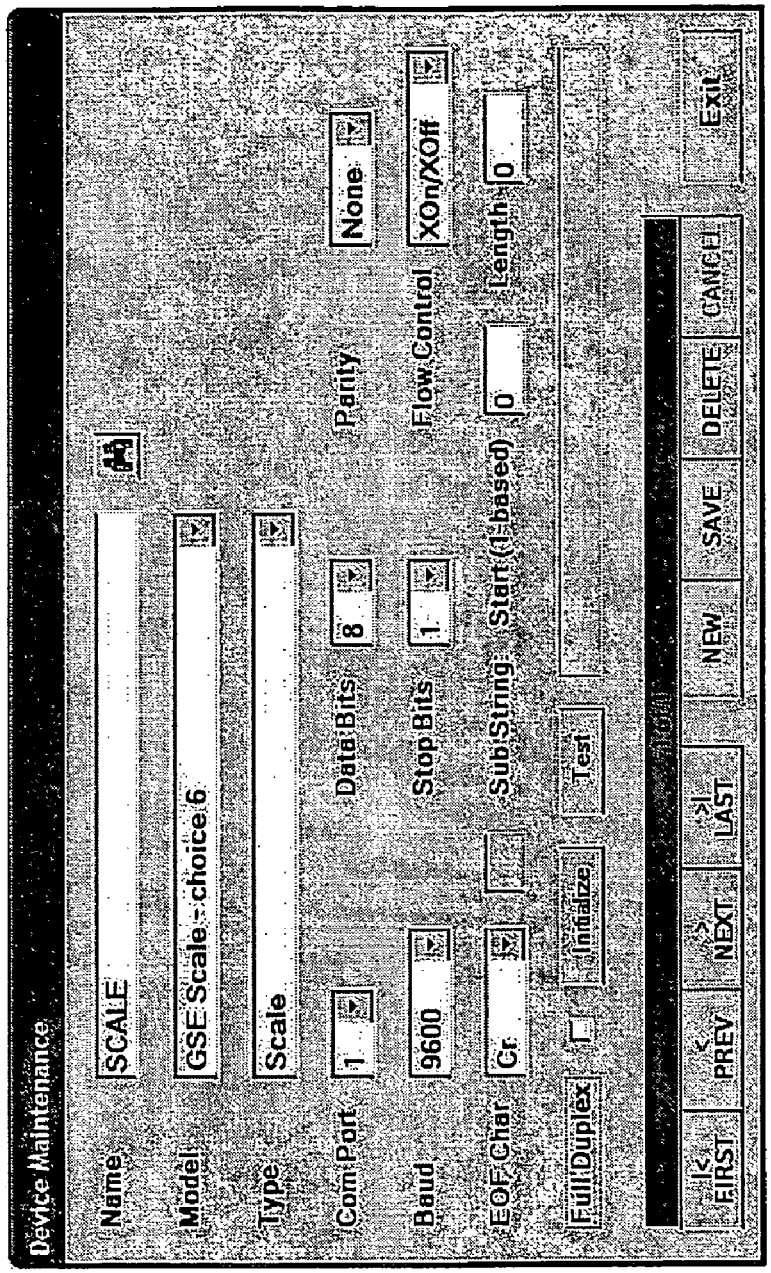
FIG. 79 is a user screen for setting up a device driver that allows a field device such as a scale to download information directly into the database of the data processing system.

FIG. 79 is another user screen that allows the user to set up a device driver that allows a field device such as a scale to download information directly into the data processing system. In the example of FIG. 79, the example field device is a GSE scale having 8 data bits, a baud rate of 9600, and 1 stop bit. The system provides a device driver allowing the driver to receive the data in the specified format, and then to reconfigure the received data so that it may be stored within the corresponding field of the selected database(s).

Figure 80:
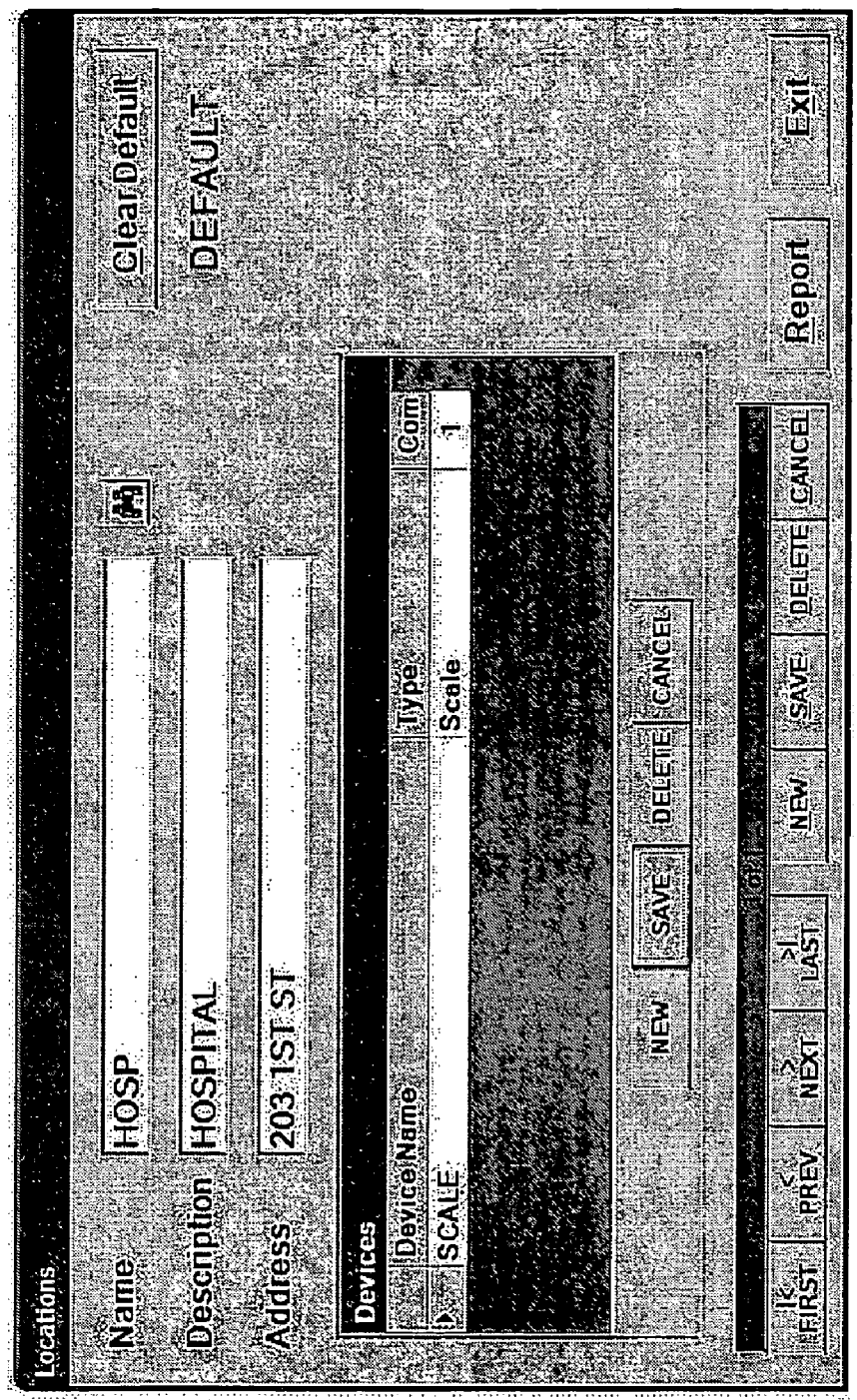
FIG. 80 is another user screen for setting up another field device assigned to a designated location within the facility.

FIG. 80 is another user screen allowing a user to set up field devices assigned to a designated location within the facility. Each field device must be assigned to a particular location so that data generated from the field device can be correctly recorded. For example, there may be many scales that generate data within the system from various locations, and it must be known as to which scale generates data from which location.

Figure 81:
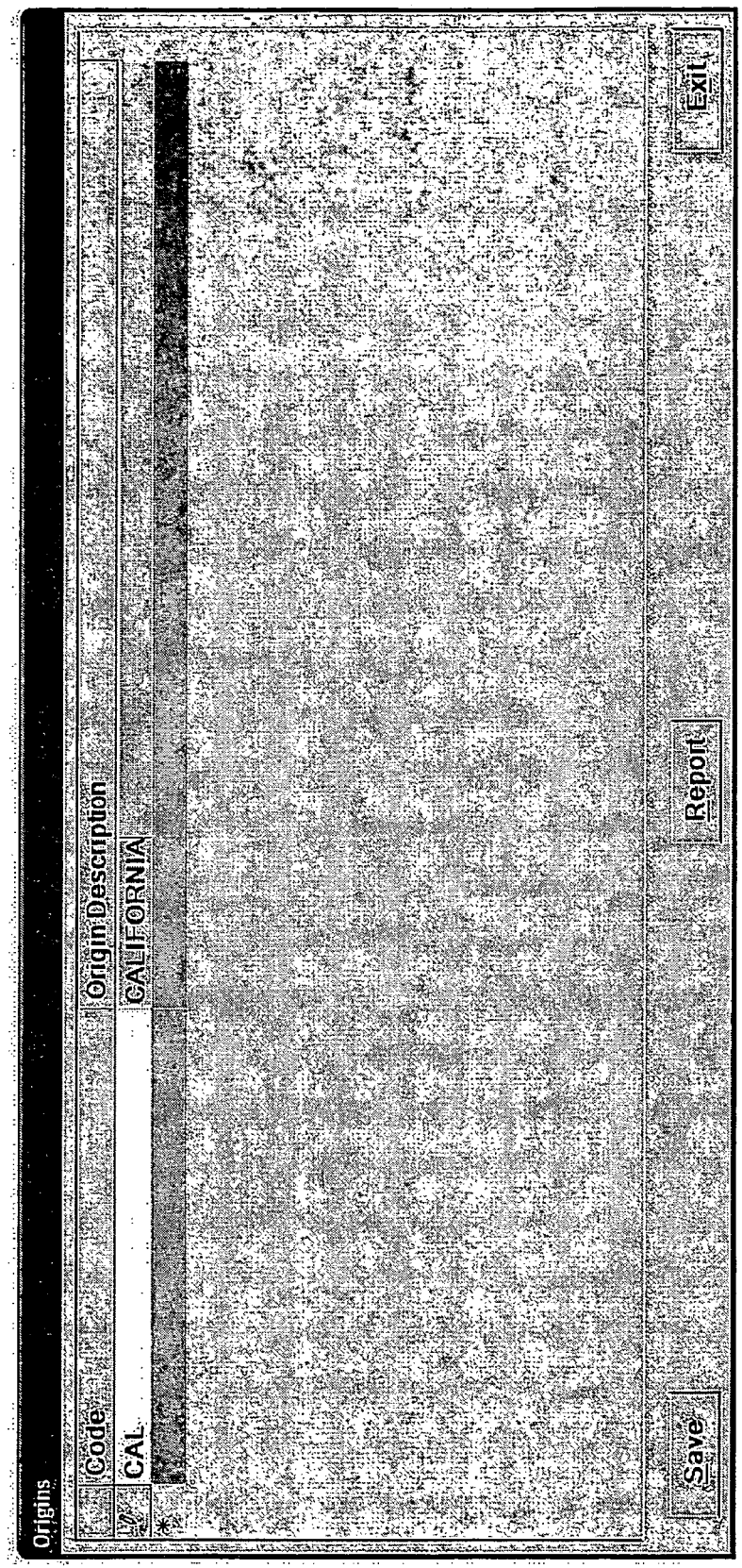
FIG. 81 is a user screen for setup of origin descriptions.

FIG. 81 is a user screen allowing set up of origin descriptions. For example, each animal entered into the system will be designated an origin code as to the location of birth. A user can build various origin descriptions and codes corresponding to exact locations where animals are born.

Figure 82:
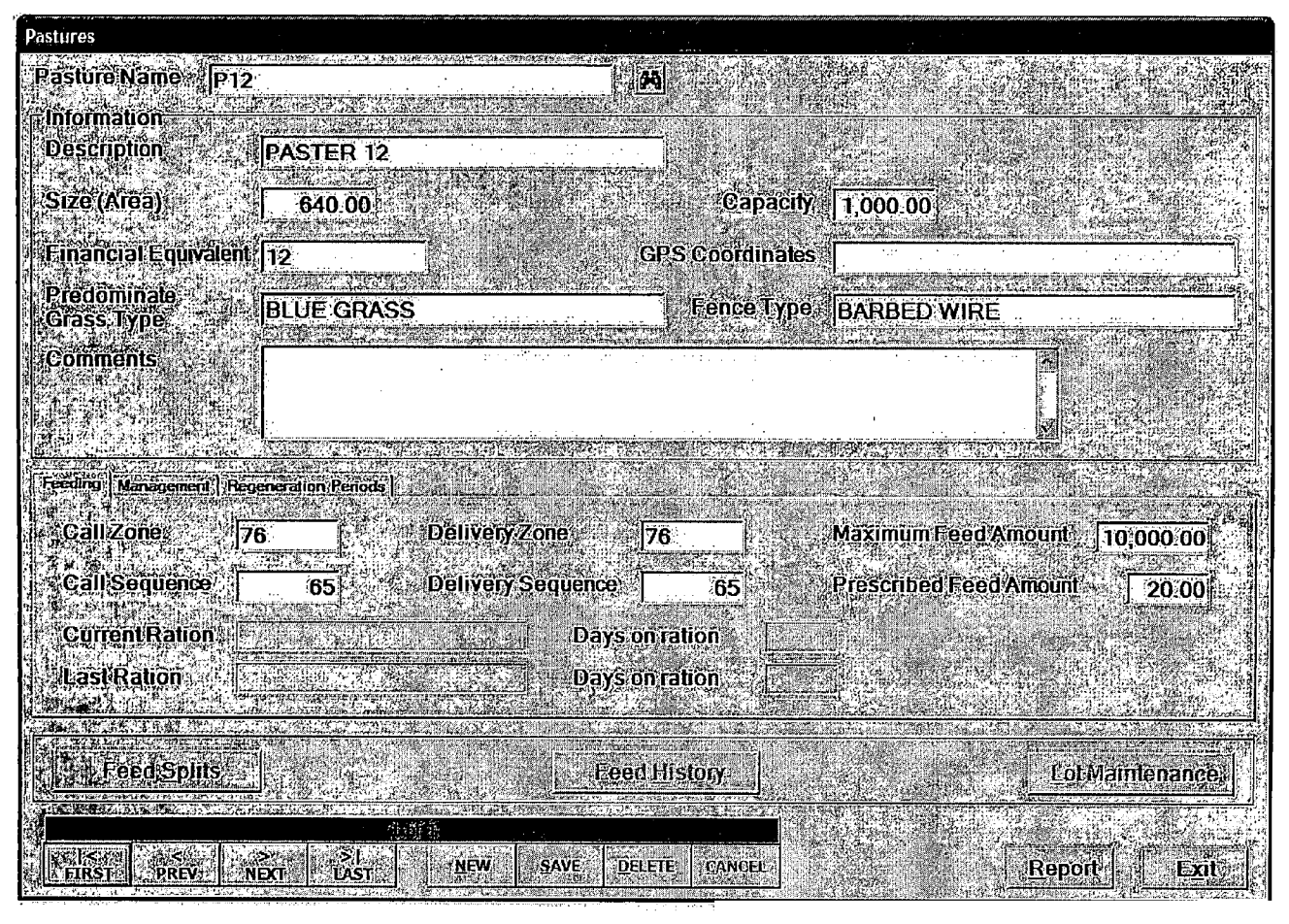

FIG. 82 is another setup screen allowing a user to designate pasture names and/or pasture designations within the system.

Figure 83:
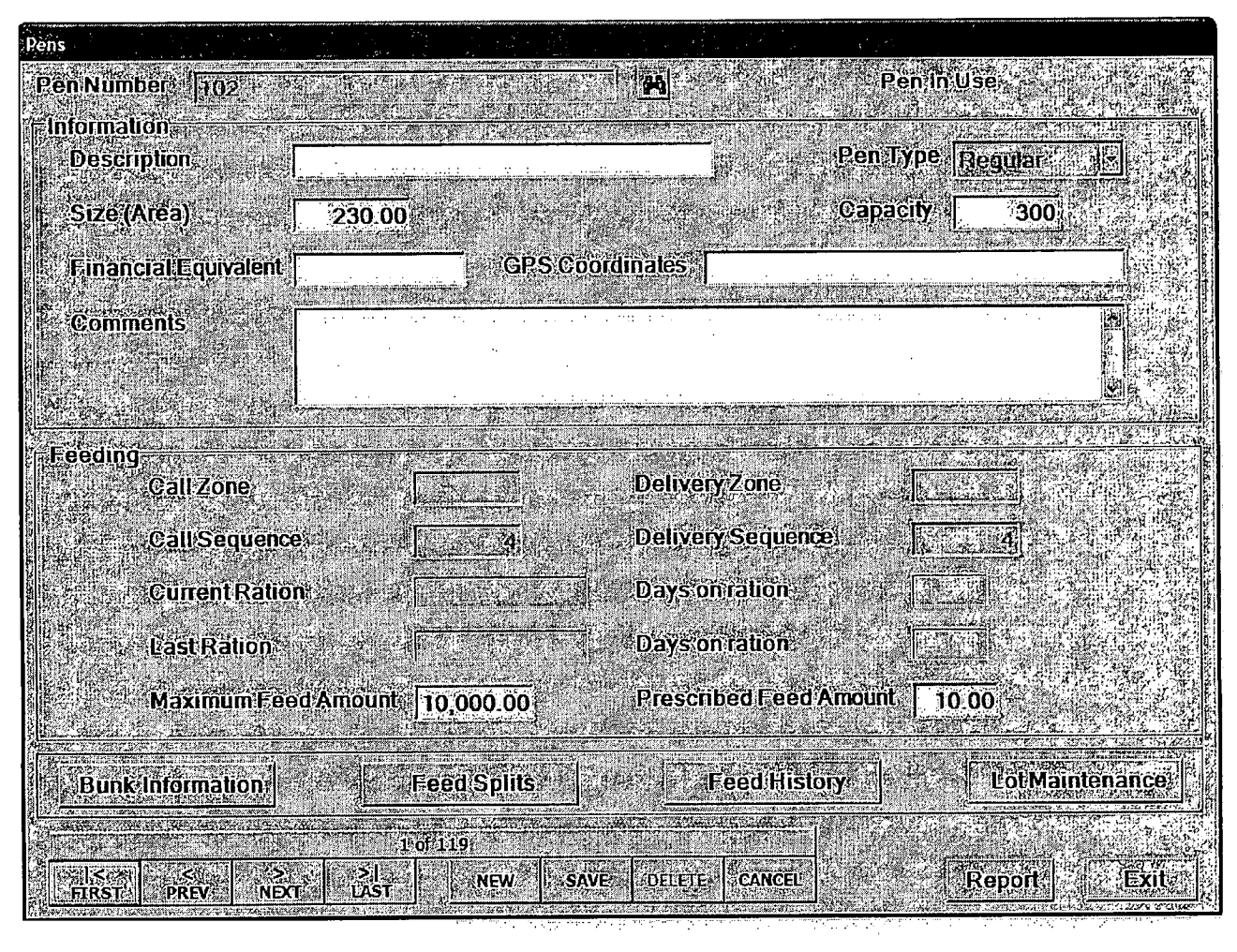

FIG. 83 is another example of a data entry screen allowing a user to set up particular pen numbers and corresponding information about each pen.

Figure 84:
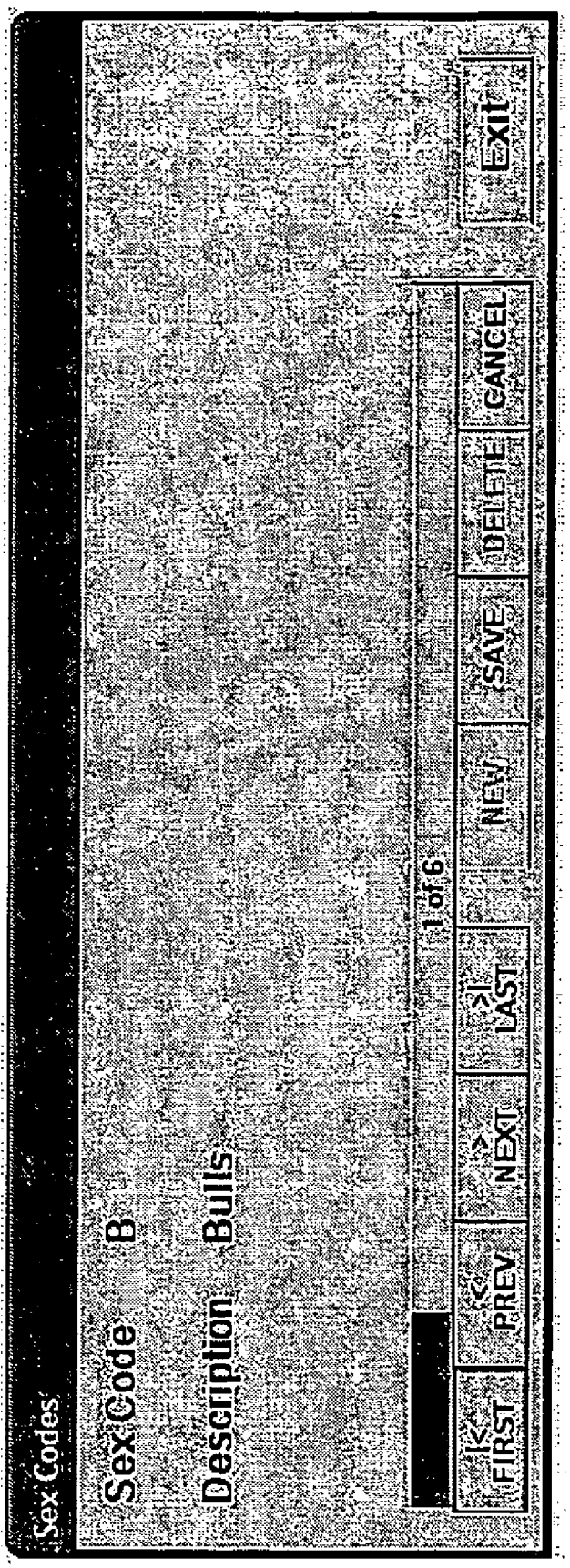
FIG. 84 is a user screen for setup of sex codes and descriptions for each animal.

FIG. 84 is a data entry screen allowing a user to set up sex codes and descriptions for each animal.

Figure 85:
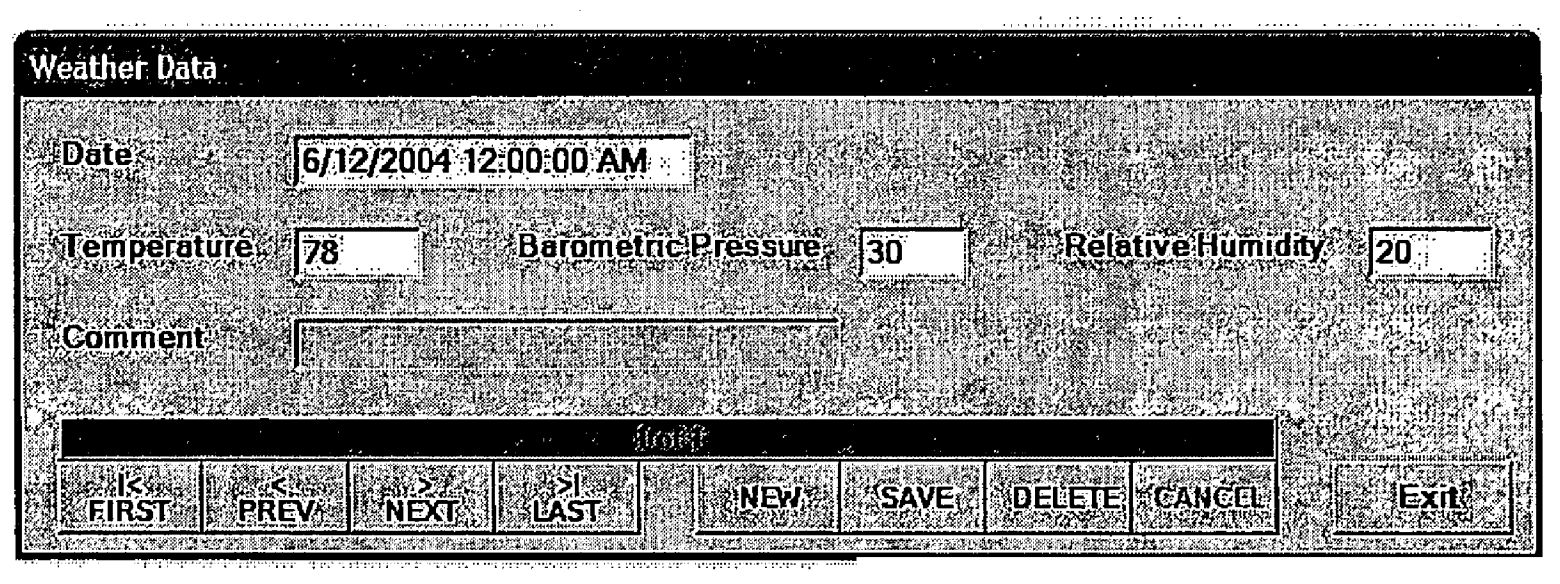

FIG. 85 is a data entry screen allowing a user to establish weather data for a particular date and time. This weather data can be used within various graphs, such as in consumption of feed over time. Increased consumption often corresponds to significant drops in temperature. Therefore, it may be useful for a feedlot to understand changes in consumption as it may relate to changes in weather.

Figure 86:
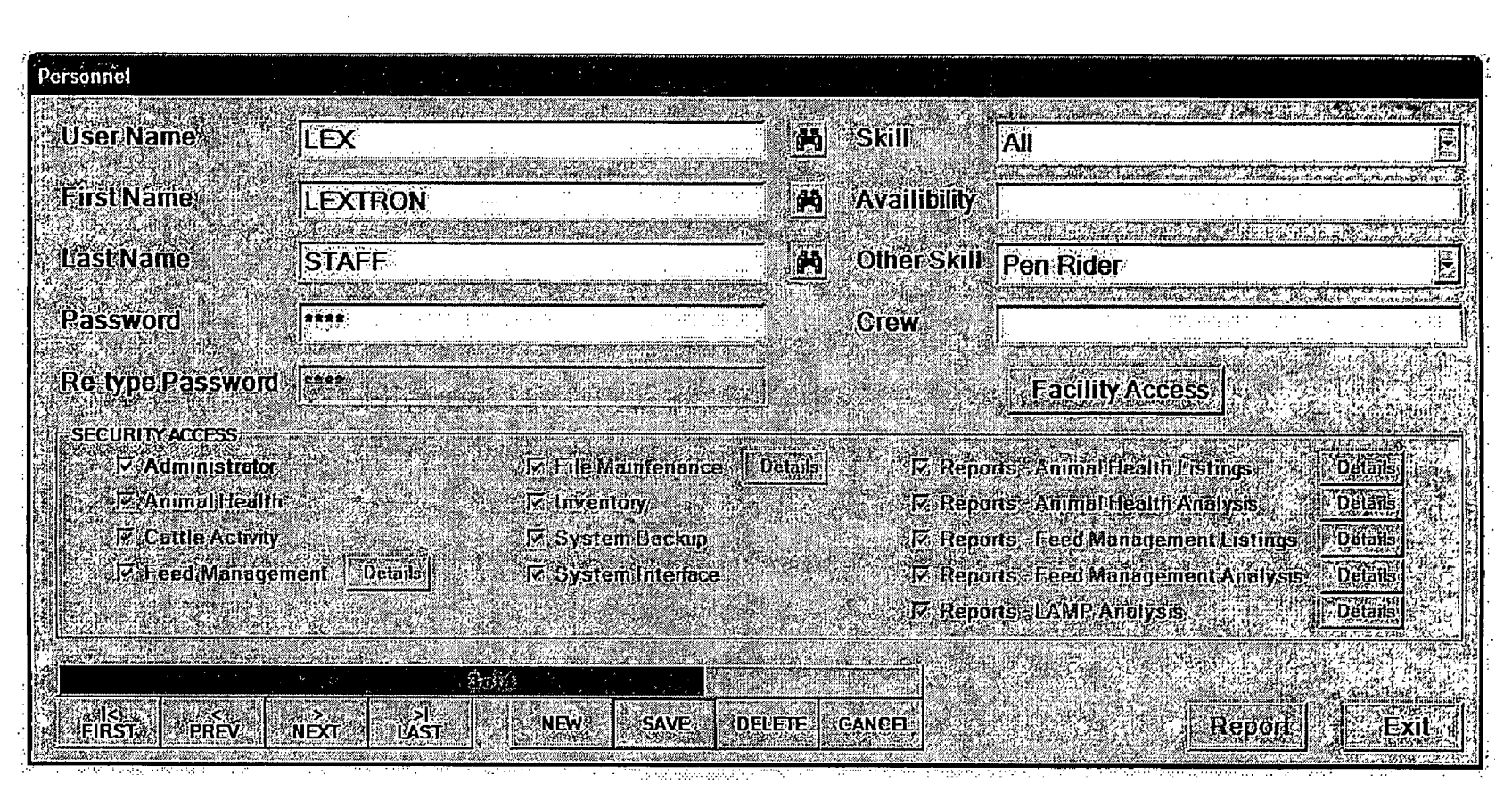

FIG. 86 is a screen allowing an administrator to identify and set up access for each and every user of the system. Each user in the system is assigned their own user name and password for security purposes. As also shown, this screen allows the administrator to designate the type or level of access for each user to include the various system modules and reports.

Figure 87:
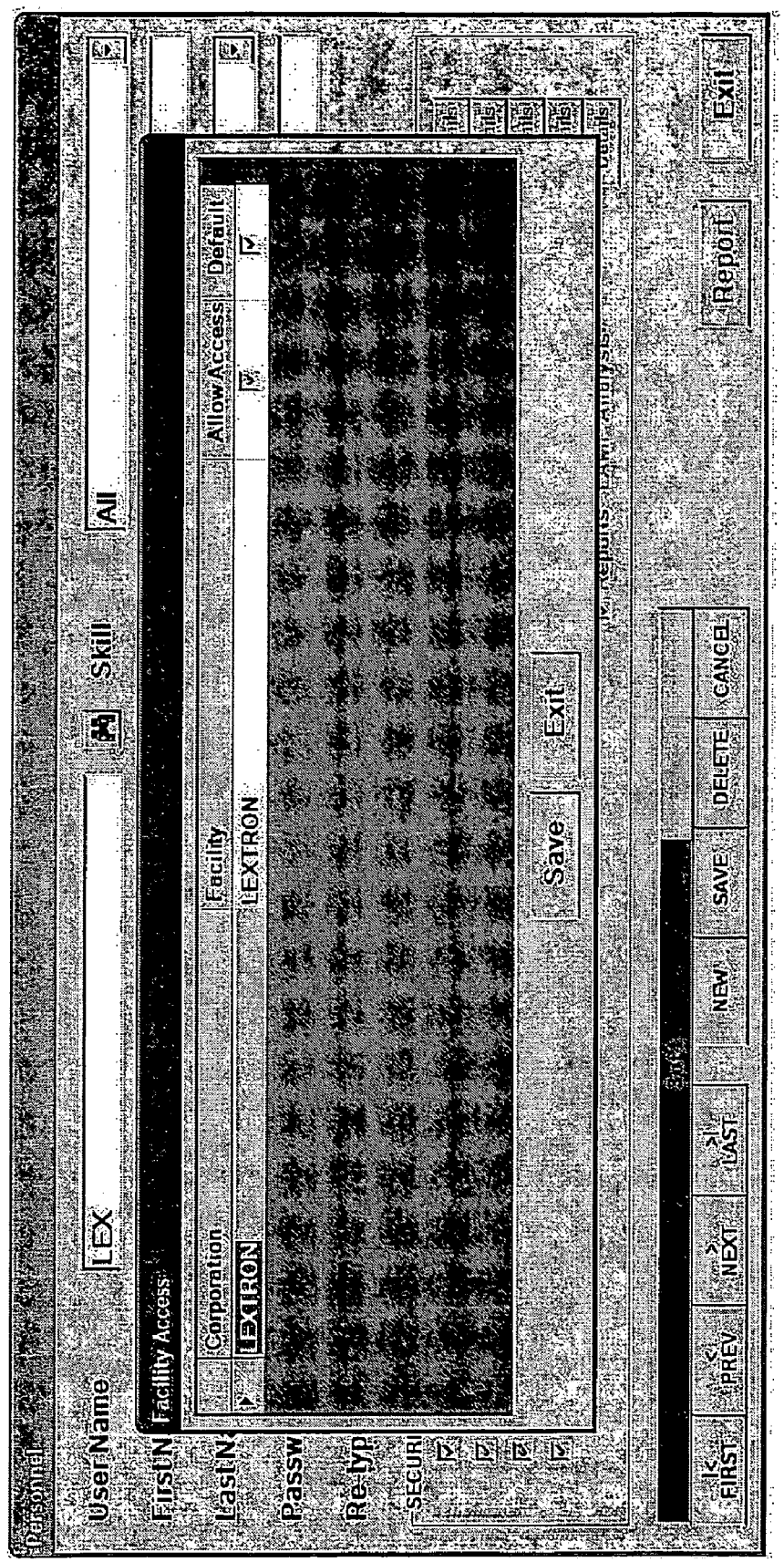
FIG. 87 is another user screen allowing an administrator to choose particular facility access for each user in the system.

FIG. 87 is another administrator screen allowing one to choose the particular facility access for each user in the system. Thus, not all users within the system are allowed to access data from each and every facility; rather, personnel may only be assigned access to particular facilities.

E. Interface Sub-Module

The interface sub-module enables all interface transactions; that is, the exchange of data between the system and sources outside the system. As mentioned above, the sources external to the data processing system may include various financial systems, outside cow/calf systems, packer systems, state and federal unique identification systems, weather systems, and portable treatment devices.

Figure 88:
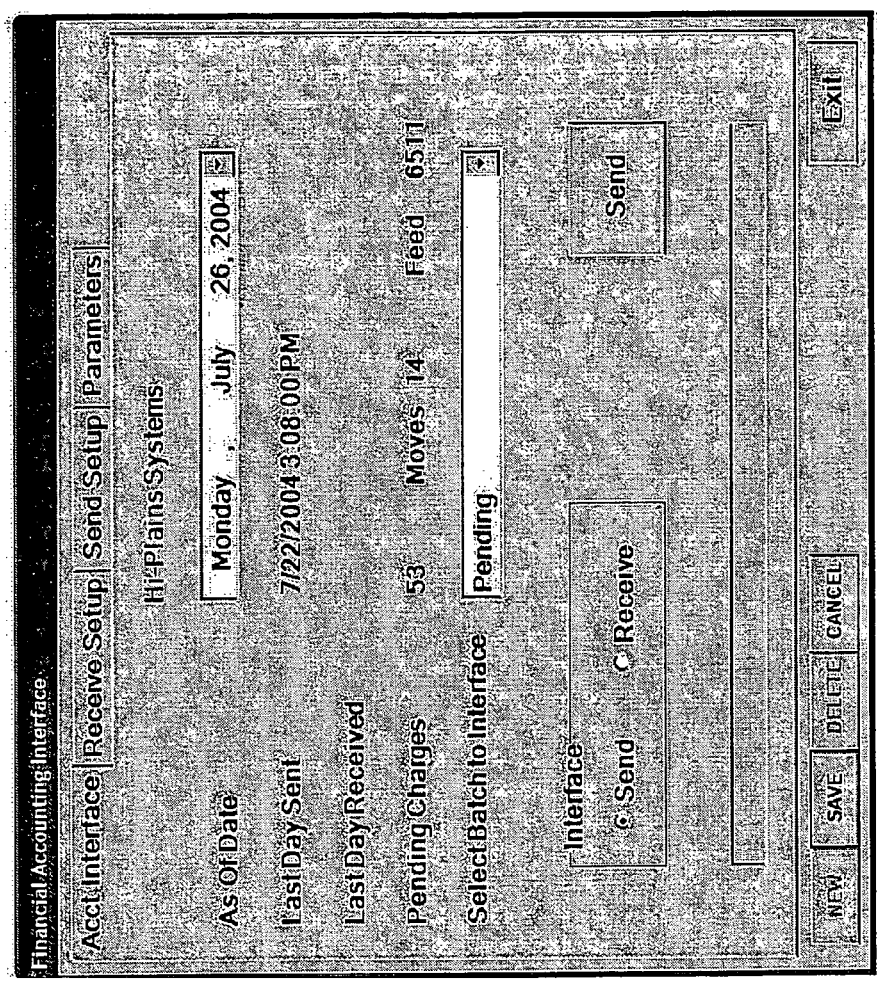
FIG. 88 is a user screen for establishing an interface with a financial accounting system.

FIG. 88 is an example setup screen allowing interface with a financial accounting system.

Figure 89:
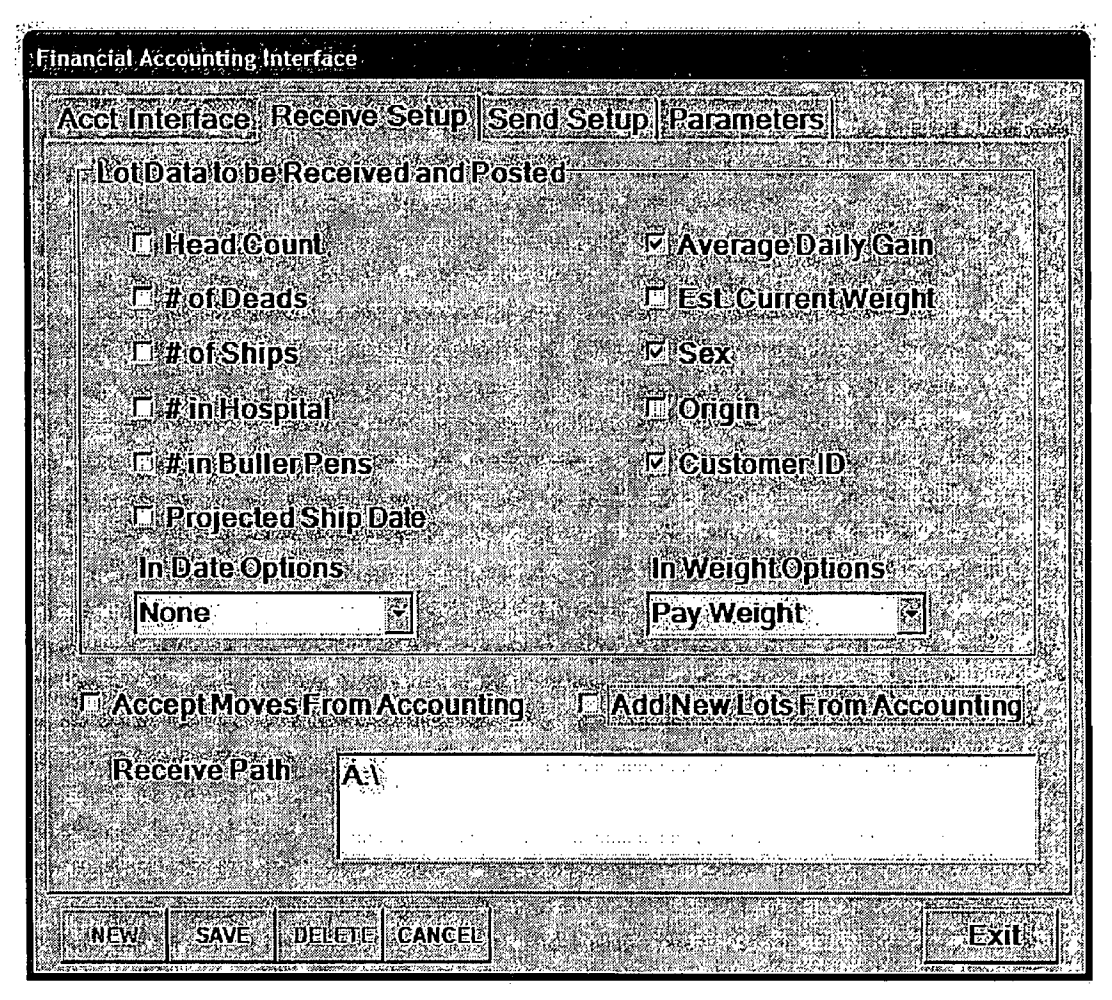

FIG. 89 is another setup screen allowing interface with a financial accounting system specifying a type of data to be received and posted from the financial accounting system.

Figure 90:
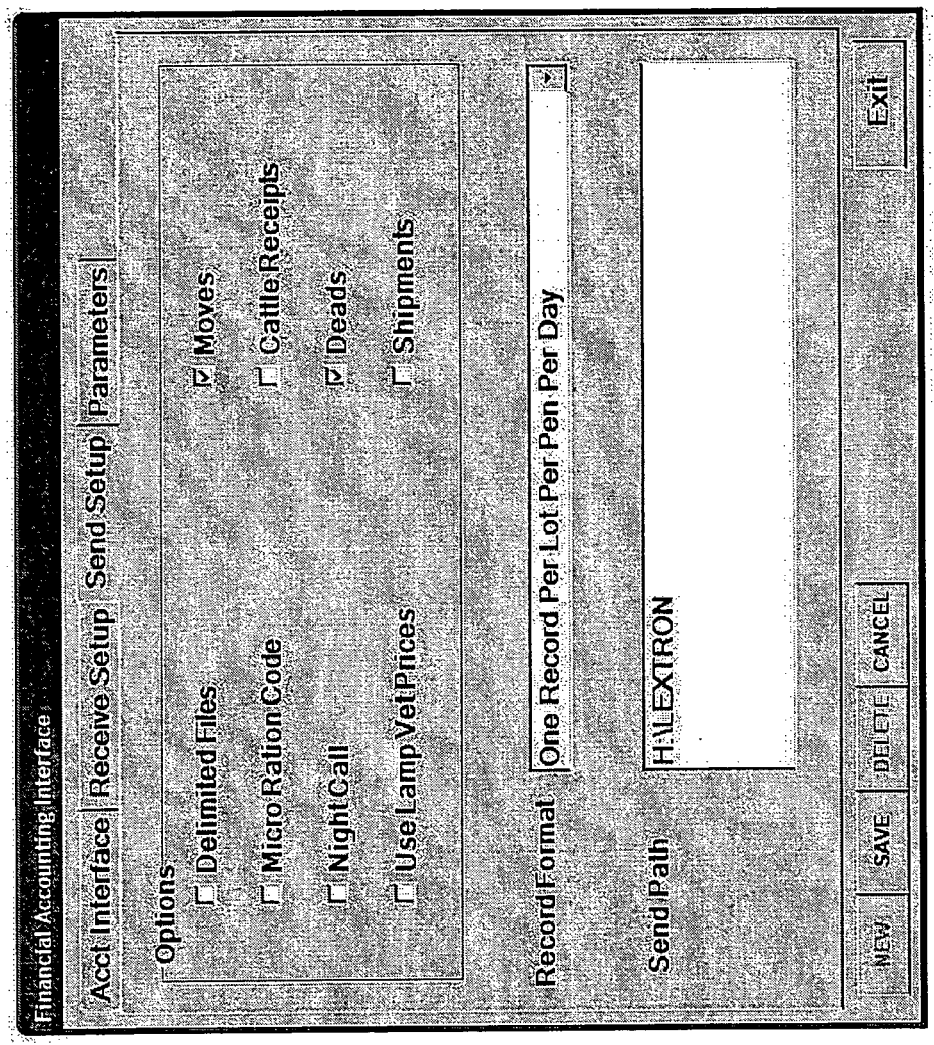
FIG. 90 is a user screen illustrating options for setup an accounting interface.

FIG. 90 is another setup screen illustrating options for setting up a financial accounting interface.

Figure 91:
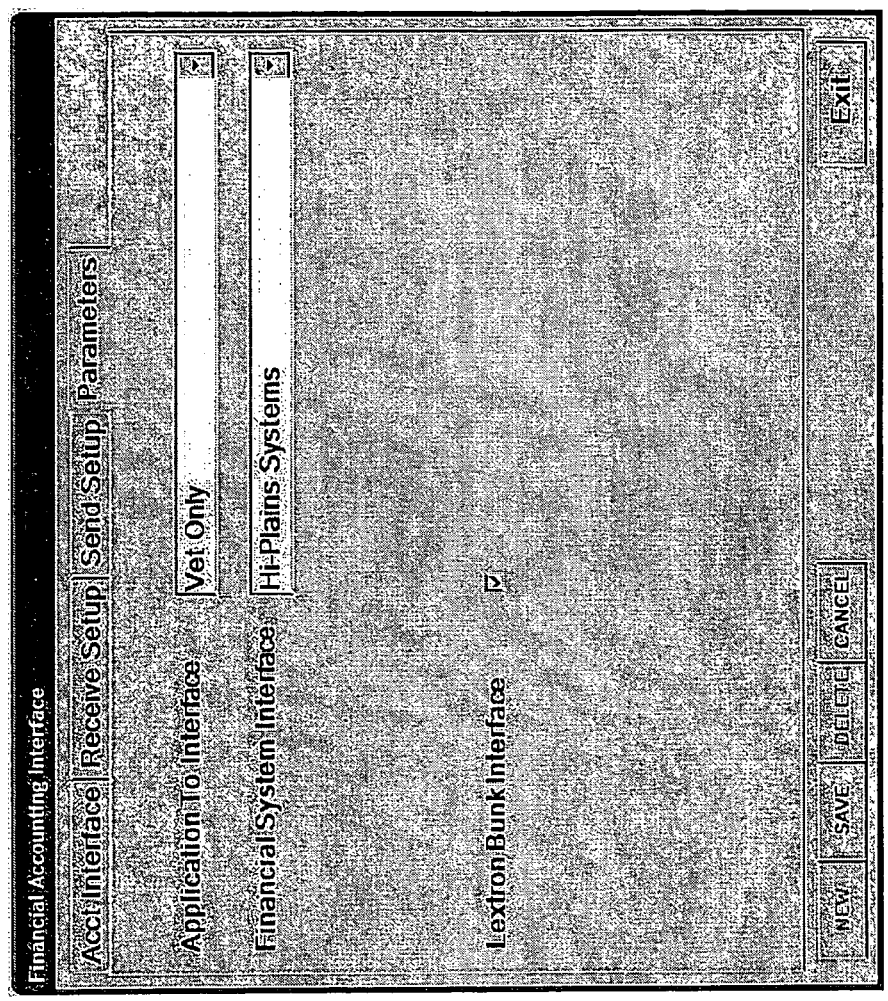
FIG. 91 is a user screen for selecting the particular type of interface and application to the interface.

FIG. 91 is another setup screen allowing interface with a financial institution where the user may select the particular financial system interface and application to the interface.

Figure 92:
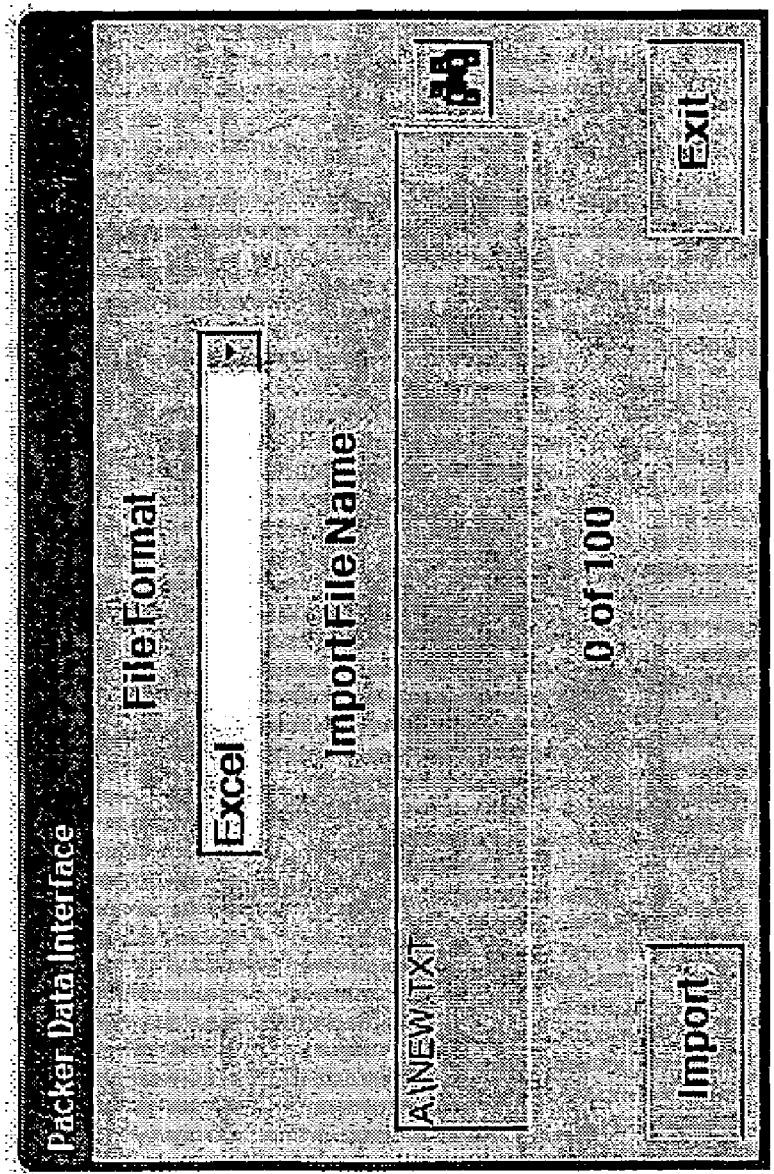
FIG. 92 is a user screen for setup of a packer data interface.

FIG. 92 is another user screen allowing setup for packer data interface. More specifically, this screen allows a user to setup a particular file format corresponding to a particular packer.

F. Reporting Sub-Module

The reporting sub-module of the present data processing system includes a variety of standard reports. The standard reports may be grouped by each sub-module and transaction groups within each sub-module. In addition to the standard reports, it is also contemplated within the present invention to provide custom reports that can be formatted for particular purposes. FIGS. 93-137 are a number of sample reports that can be generated from the data processing system. Each different report is shown as having its own unique report number. The extensive number of sample reports illustrate the vast quantity of diverse data that is managed by the present invention. Each report is generated by selecting the desired data fields from the central database. Implementation of a central database allows a user to easily generate reports by sorting one or more data fields. The reporting sub-module allows a user to designate which data fields are to be generated in the report, and then to modify the report as necessary to add or delete individual data fields.

FIG. 93 is a hospital pen location report providing the tag number for each animal in the particular hospital pen, and also illustrating the home pen, from pen, and lot for each particular animal.

FIG. 94 is another hospital pen report, but data is sorted based upon the particular hospital pen, and the animals in each of the listed hospital pens.

FIG. 95 is a hospital location report showing last treatment dates for particular animals.

FIG. 96 is a hospital movements report sorted by lots showing movement of identified animals for a particular day.

FIG. 97 illustrates another hospital movement report sorted by lot, as well as a hospital/special pen movements summary.

FIG. 98 is another hospital movements report sorted by lot, and also showing a summary of first day pulls to the hospitals. The first day pulls identify those animals that are transported to the hospital on that particular date.

Figure 99:
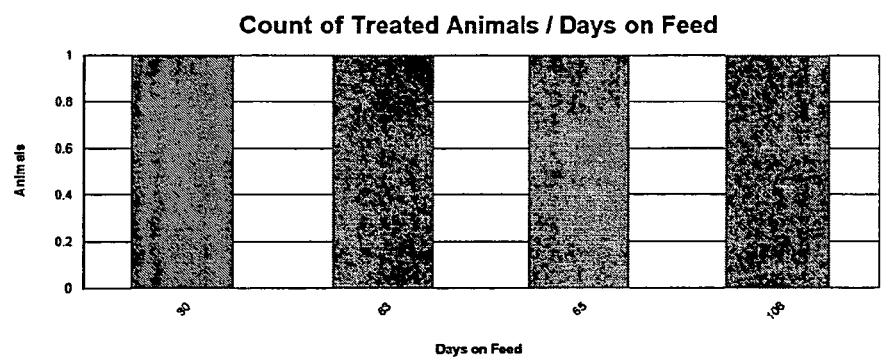

FIG. 99 is a report showing a count of animals treated, average days treated, and average days on feed.

Figure 100:
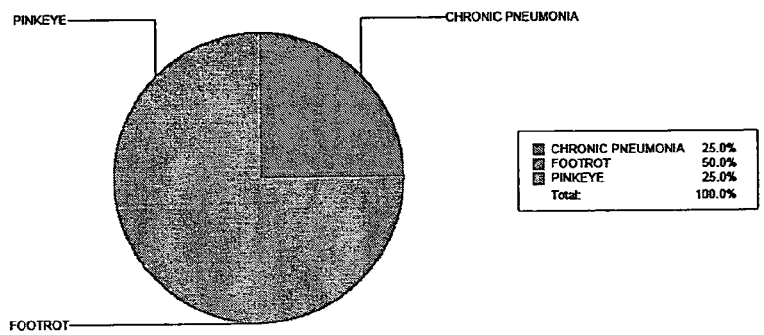

FIG. 100 shows a diagnosis breakdown for selected ailments, the average days treated, and average days on feed.

FIG. 101 shows a report for detailing information on all treatments for a particular lot and pen.

FIG. 102 is a report showing information including the treatment analysis summary and a corresponding cost analysis summary for treatments administered.

FIG. 103 is an overall lot summary report including information regarding head counts, treatment summaries, death summaries, and price summaries.

FIG. 104 is another report showing a lot summary including the dates in, heads in, treatments, and mortality information.

FIG. 105 is a lot comparison report detailing health related deaths and a description of the corresponding ailments for a particular location such as a feedlot.

FIG. 106 illustrates a lot analysis by owner report detailing the location, count, and other information for a particular owner.

FIG. 107 is a pen rider analysis report for a designated pen rider, an identification of the animals and diagnosis corresponding to the pen rider.

FIG. 108 is a lot analysis report detailing information on a particular lot chosen.

FIG. 109 is a detailed treatment history report by listing drugs administered during treatments.

FIG. 110 is a lot summary report detailing additional information on a particular chosen lot.

FIG. 111 illustrates a treatment exceptions report. This report captures information on any changes made to a pre-configured treatment. For example, if a user decides to adjust the dosage or type of drug administered to an animal versus that which is recommended in the preconfigured treatment, this report details all changed data.

FIG. 112 illustrates an inventory variance report detailing information on the actual amount of a drug on-hand versus an estimated on-hand amount based upon prior inventory and usage.

FIG. 113 is a billing report for a designated lot including information on the cost of various drugs administered.

FIG. 114 is another billing report detailing information by individual treatments administered to selected animals.

FIG. 115 is a quality assurance report detailing information on mass treatments and individual treatments for a particular lot.

FIG. 116 is a morbidity report summarizing treatments, diagnosis breakdowns, deads, and movements.

FIG. 117 is a morbidity report detailing information on diseases, treatments, and other information on animals that suffer from the various diagnosed afflictions.

FIG. 118 is another morbidity report providing treatment detail for date by origin reported by lot and pen number.

FIG. 119 is a mortality summary report for a designated period.

FIG. 120 is another mortality report detailing deaths by date range, to include information on treatment history of a particular animal.

FIG. 121 is a death notification slip report detailing information on the death of a particular animal.

FIG. 122 is an active item drug report showing drugs in inventory for a particular location, the recommended dosage, and the unit of measure for administering the dosage.

FIG. 123 is a lot master listing report detailing customer information for cattle retained in a particular location. Specifically, this report provides the sex, average weight, and head count for each owner in each lot and pen.

FIG. 124 is a report showing suggested treatments sorted by diagnosis codes, the detailed information including the recommended drugs, dosages, and units.

FIG. 125 is a scheduled processing report listing particular lot and pen numbers that are scheduled for a particular type of processing on the designated date. The scheduled processing could include any number of cattle management functions to include a scheduled sorting operation, animal health check-ups, and others.

FIG. 126 is a processing history report detailing information on treatments administered to the designated pen and lot numbers.

FIG. 127 is a listing of the active diagnosis codes.

FIG. 128 is a weight gain report showing information on weight gain for a particular lot and pen.

FIG. 129 is a listing of implant status codes.

FIG. 130 is a railer summary report detailing the number of animals railed, average days treated and average days on feed.

FIG. 131 is a railer analysis report detailing reasons for animals being railed.

FIG. 132 is a railer notification slip detailing instructions for the animal being railed.

FIG. 133 is a cattle activity receiving report showing the date, lot number, pen number and number of head received on the date.

FIG. 134 is a cattle activity movement report detailing date information on movement of cattle between various pens and lots.

FIG. 135 is a cattle activity deads report detailing information on cattle that have died at various locations.

FIG. 136 is a cattle activity shipment report detailing information on animals shipped from one location to another location.

FIG. 137 is a pen master listing report sorting the information by pen number.

The particular embodiments described above are intended to explain the best mode presently known in practicing the invention and to enable others skilled in the art to utilize the invention in such or in other embodiments and with various modifications required by their particular application or use of the invention. Therefore, it is intended that the appended claims be construed to include the alternative embodiments to the extent permitted by the prior art. Additionally, although the present invention is discussed particularly with respect to cattle, it shall be understood that the invention is also applicable for management of all livestock.

What is claimed is:

1. A system for managing cattle, said system comprising:
   a data processor;
   data storage associated with said data processor;
   programming instructions residing in said data storage for executing instructions based upon user data input;
   said programming instructions including a plurality of recommended actions for management based upon mathematical relationships applied to a plurality of criteria corresponding to selected animal data;
   a data input device for inputting data into said data processing system;
   means for outputting information reflective of the recommendations said outputting means including at least one of a printed report and a user interface screen prescribing details on the recommended action; and
   wherein data input into said data processing system is stored in a central database of said data storage, and subsequent data inputs made to the system result in providing an updated recommendation action taking into account a change in value of the mathematical relationships based upon subsequent data inputs that differ from initial data inputs.

2. A system, as claimed in claim 1, wherein:
   one recommended action of said plurality of recommended actions includes prescribing a change of ration for the animal.

3. A system, as claimed in claim 1, wherein:
   one recommended action of said plurality of recommended actions includes prescribing a change of location of the animal.

4. A system, as claimed in claim 1, wherein:
   one recommended action of said plurality of recommend actions includes prescribing a treatment for the animal.

5. A system, as claimed in claim 1, wherein:

one recommended action of said plurality of recommended actions includes prescribing a method of administering a ration for the animal.

6. A method of generating a recommended action in a data processing system for cattle management, said method comprising the steps of:

establishing a plurality of criteria corresponding to individual animal data and group animal data;

generating at least one mathematical formula incorporating at least one criteria; and determining a value for the at least one formula corresponding to a recommended management action, said recommended management action including at least one of a change of ration for an animal, a change of location of the animal, a treatment for the animal, and a method of administering the ration to the animal.

7. A method, as claimed in claim 6, wherein:

said criteria include a feeding of the day, a percentage of how much to feed an animal during a particular feeding, a ration code identifying a type of ration, and an amount of ration per head of cattle.

8. A method, as claimed in claim 6, wherein:

said at least one mathematical formula includes a plurality of mathematical formulas.

9. A method, as claimed in claim 6, wherein:

said value of the at least one formula comprises a range of values.

10. A method, as claimed in claim 6, wherein:

said criteria include at least one of a weight of the animal, a breed of the animal, and a sex of the animal, wherein a change of location of the animal is determined by the at least one mathematical formula that sorts cattle according to the criteria.

11. A method, as claimed in claim 6, wherein:

said at least one criteria includes previous drugs administered to an animal and a current diagnosis of the animal for determining the treatment for the animal.

* * * * *

UNITED STATES PATENT AND TRADEMARK OFFICE
CERTIFICATE OF CORRECTION

PATENT NO. : 7,543,549 B2  Page 1 of 1
APPLICATION NO. : 11/228020
DATED : June 9, 2009
INVENTOR(S) : Valencia et al.

It is certified that error appears in the above-identified patent and that said Letters Patent is hereby corrected as shown below:

Column 32, Line 52: please delete "recommendation" and insert --recommended--

Signed and Sealed this

Twenty-sixth Day of January, 2010

David J. Kappos
*Director of the United States Patent and Trademark Office*